(12) United States Patent
Yamamoto

(10) Patent No.: US 10,638,725 B2
(45) Date of Patent: May 5, 2020

(54) ESTIMATION METHOD, INFORMATION PROCESSING APPARATUS, AND NON-TRANSITORY COMPUTER-READABLE STORAGE MEDIUM FOR ESTIMATING MOTION OF ANIMAL

(71) Applicant: FUJITSU LIMITED, Kawasaki-shi, Kanagawa (JP)

(72) Inventor: Kiyoko Yamamoto, Kobe (JP)

(73) Assignee: FUJITSU LIMITED, Kawasaki (JP)

(*) Notice: Subject to any disclaimer, the term of this patent is extended or adjusted under 35 U.S.C. 154(b) by 0 days.

(21) Appl. No.: 16/108,595

(22) Filed: Aug. 22, 2018

(65) Prior Publication Data

US 2018/0352786 A1    Dec. 13, 2018

Related U.S. Application Data

(63) Continuation of application No. PCT/JP2016/056146, filed on Feb. 29, 2016.

(51) Int. Cl.
*A01K 29/00* (2006.01)
*A01K 67/00* (2006.01)
(Continued)

(52) U.S. Cl.
CPC .......... *A01K 29/005* (2013.01); *A01K 11/006* (2013.01); *A01K 29/00* (2013.01);
(Continued)

(58) Field of Classification Search
CPC .... A01K 29/005; A01K 11/006; A01K 67/00; A01K 29/00; A61B 5/1104; A61B 5/112;
(Continued)

(56) References Cited

U.S. PATENT DOCUMENTS

2006/0000420 A1    1/2006  Martin Davies
2006/0106289 A1*   5/2006  Elser ................... A61B 5/0059
                                                                    600/300

(Continued)

FOREIGN PATENT DOCUMENTS

JP    2003-228701 A    8/2003
JP    2008-500046 A    1/2008
(Continued)

OTHER PUBLICATIONS

International Search Report w/English translation and Written Opinion in Japanese dated May 10, 2016, issued in counterpart International Application No. PCT/JP2016/056146 (9 pages).
(Continued)

*Primary Examiner* — Brian Wilson
(74) *Attorney, Agent, or Firm* — Westerman, Hattori, Daniels & Adrian, LLP

(57) ABSTRACT

An estimation method performed by a computer, the method comprising: distinguishing ground-off and landing timings of respective four limbs of an animal based on measurement data acquired by using a motion sensor attached to the animal which has four limbs, and identifying a limb which interlocks with a disorder of a motion waveform upon a motion of the animal, based on the distinguished ground-off and landing timings of each of the four limbs of the animal.

18 Claims, 42 Drawing Sheets

ATTACHING

TRAINING (DATA COLLECTION)

DATA ANALYSIS

(51) Int. Cl.
*A01K 11/00* (2006.01)
*A61B 5/11* (2006.01)

(52) U.S. Cl.
CPC .............. *A01K 67/00* (2013.01); *A61B 5/112* (2013.01); *A61B 5/1104* (2013.01); *A61B 2503/40* (2013.01)

(58) Field of Classification Search
CPC ... A61B 5/7282; A61B 5/6831; A61B 5/1122; A61B 2503/40; A61D 99/00
See application file for complete search history.

(56) References Cited

U.S. PATENT DOCUMENTS

2007/0000216 A1* 1/2007 Kater .................. A01K 29/005 54/1
2007/0130893 A1* 6/2007 Davies ................. A01K 11/008 54/1
2008/0021352 A1 1/2008 Keegan et al.
2016/0030804 A1 2/2016 Mizuochi et al.

FOREIGN PATENT DOCUMENTS

| | | |
|---|---|---|
| JP | 2008-504025 A | 2/2008 |
| JP | 2008-264114 A | 11/2008 |
| JP | 2016-13112 A | 1/2016 |
| WO | 2008/011590 A2 | 1/2008 |

OTHER PUBLICATIONS

Extended Search Report dated Feb. 26, 2019, issued in counterpart EP Application No. 16892475.1 (8 pages).

* cited by examiner

FIG. 12A
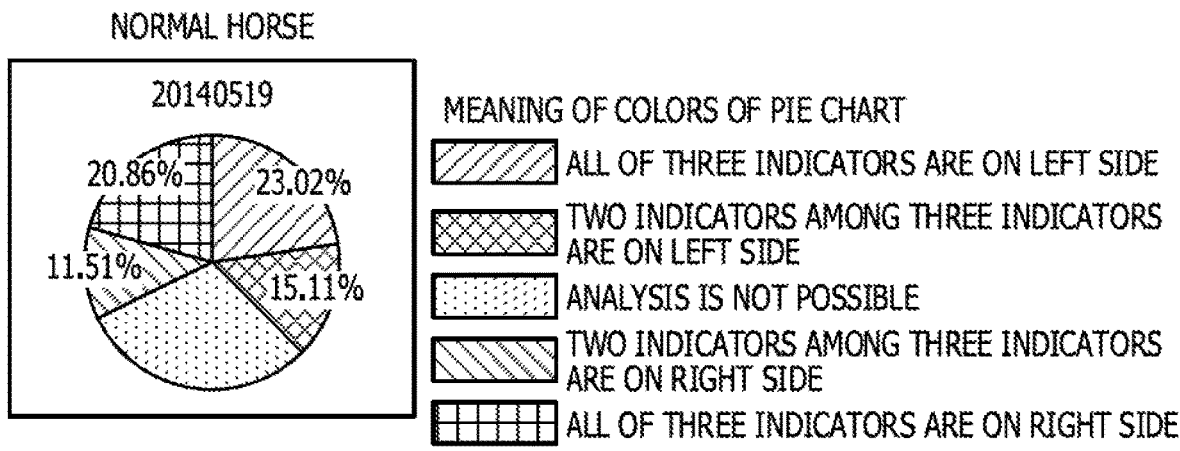
FIG. 12B
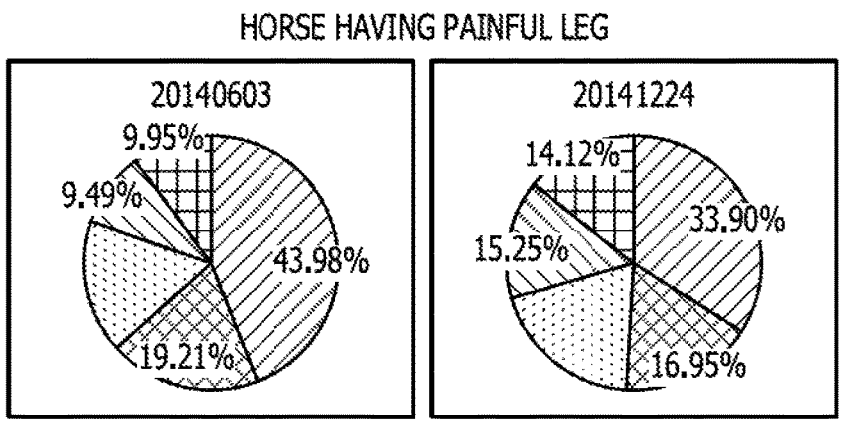
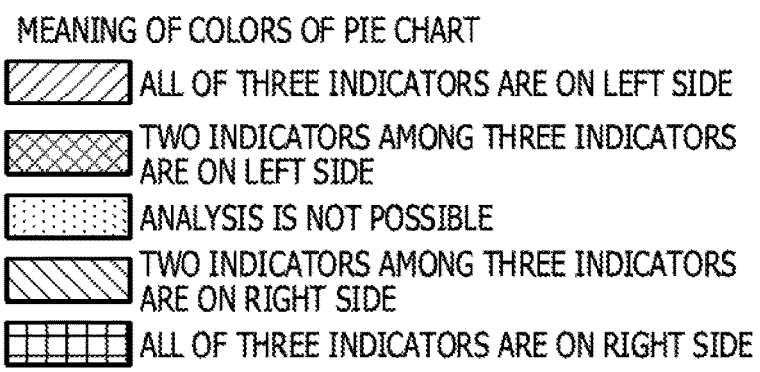

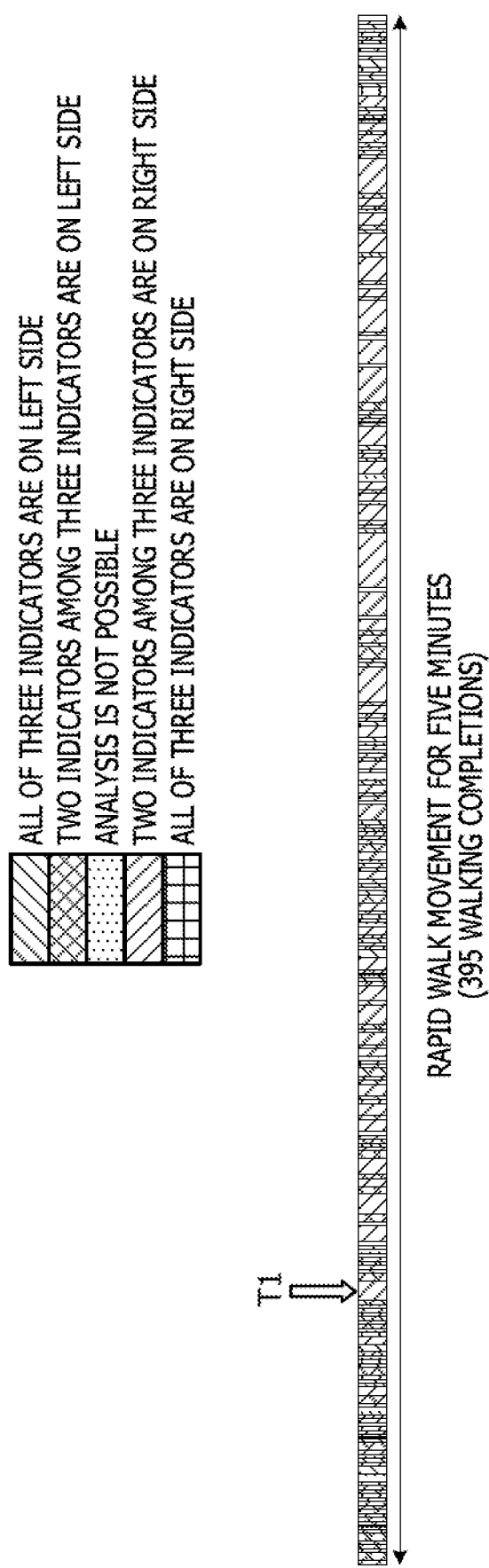

FIG. 15
SOLID LINE: RIGHT LIMB, BROKEN LINE: LEFT LIMB
(1) walk
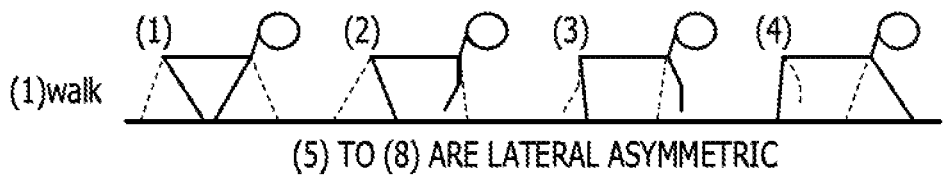
(5) TO (8) ARE LATERAL ASYMMETRIC
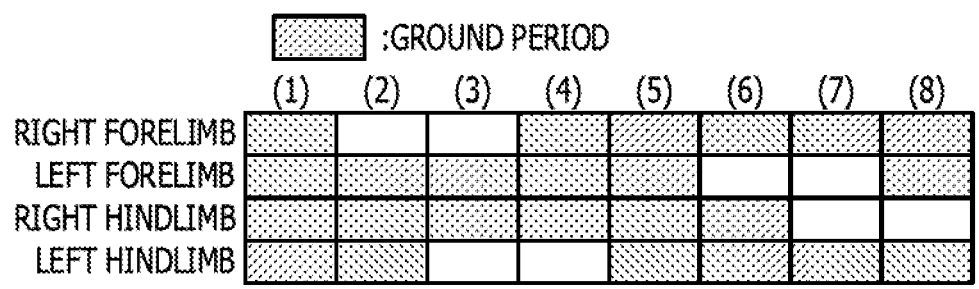
(2) trot
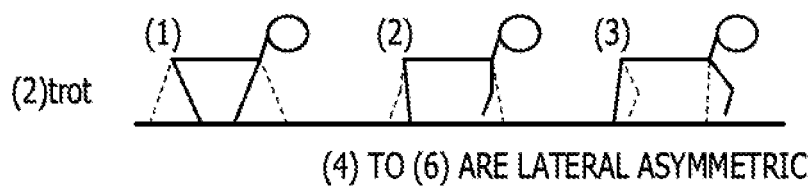
(4) TO (6) ARE LATERAL ASYMMETRIC
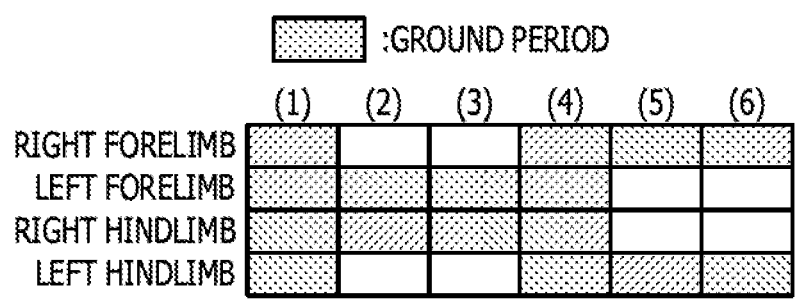

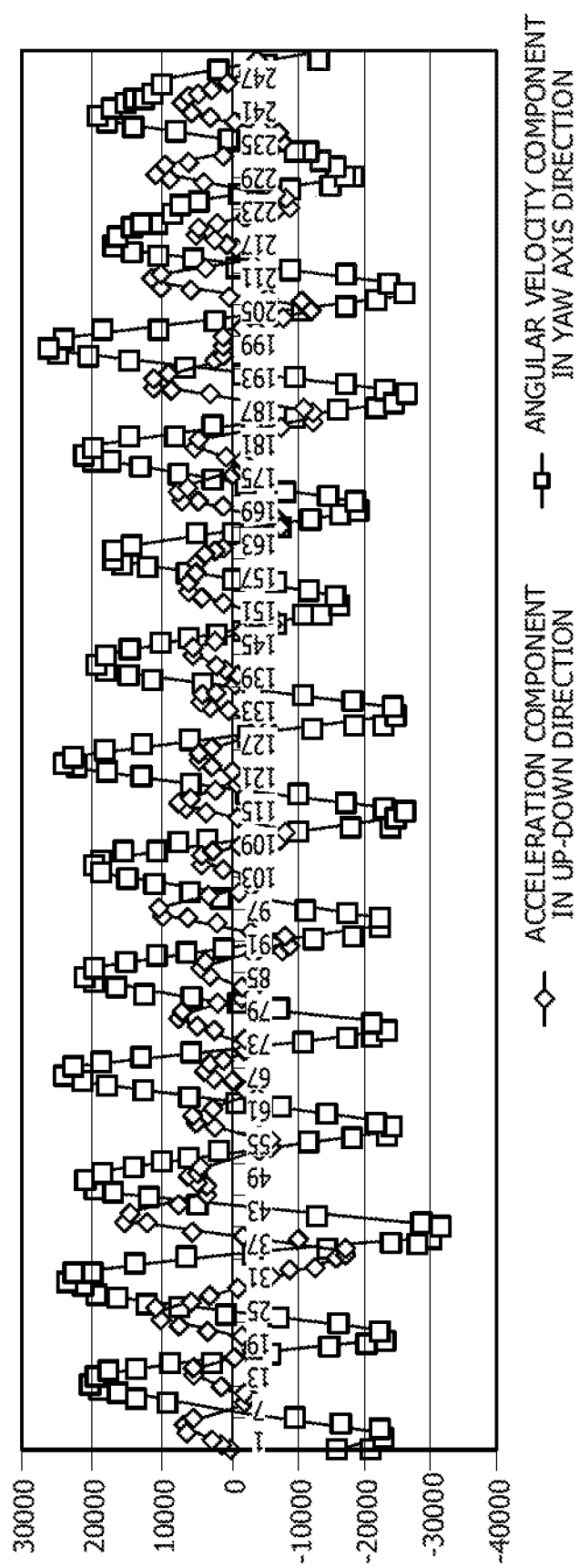

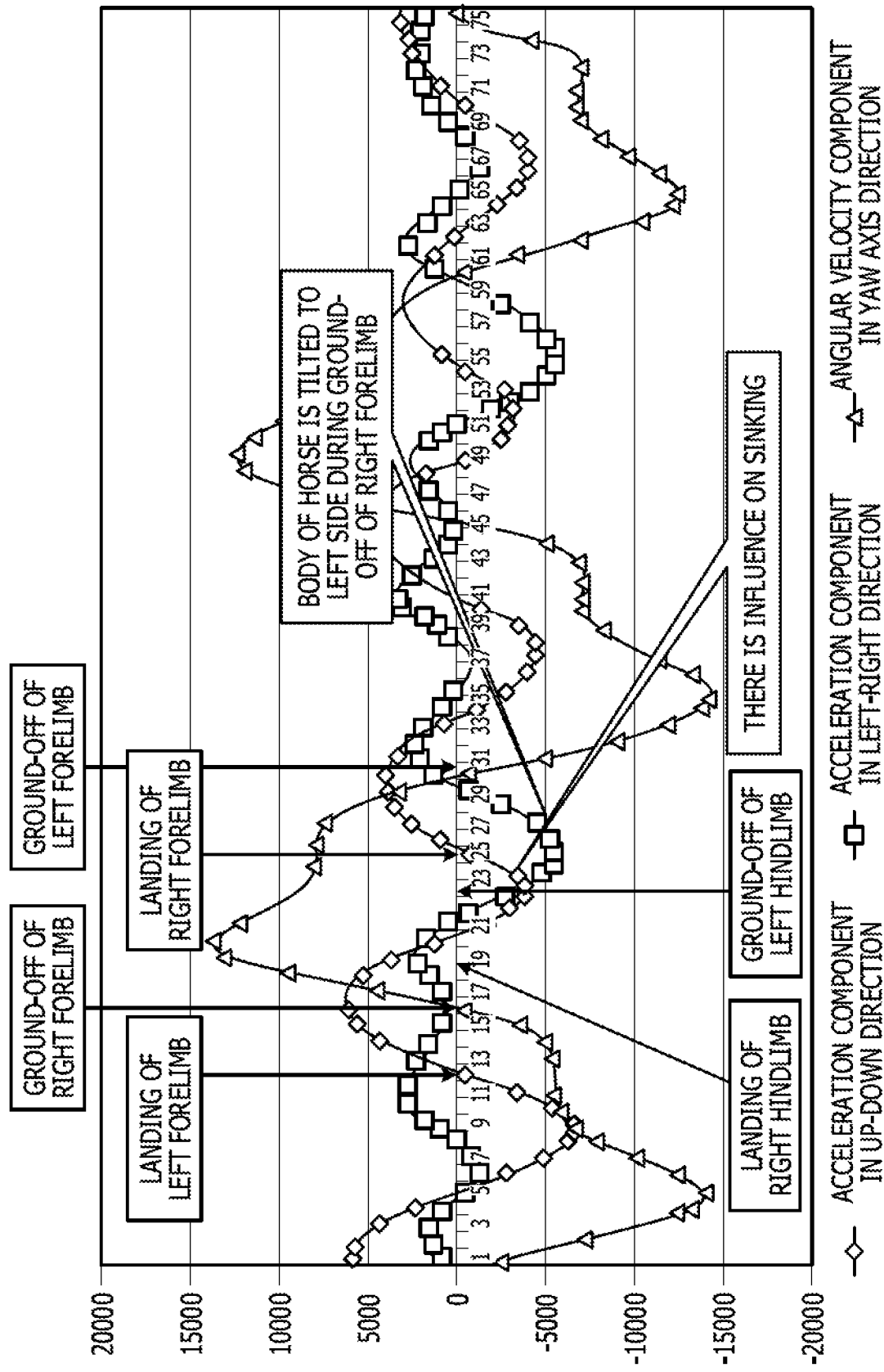

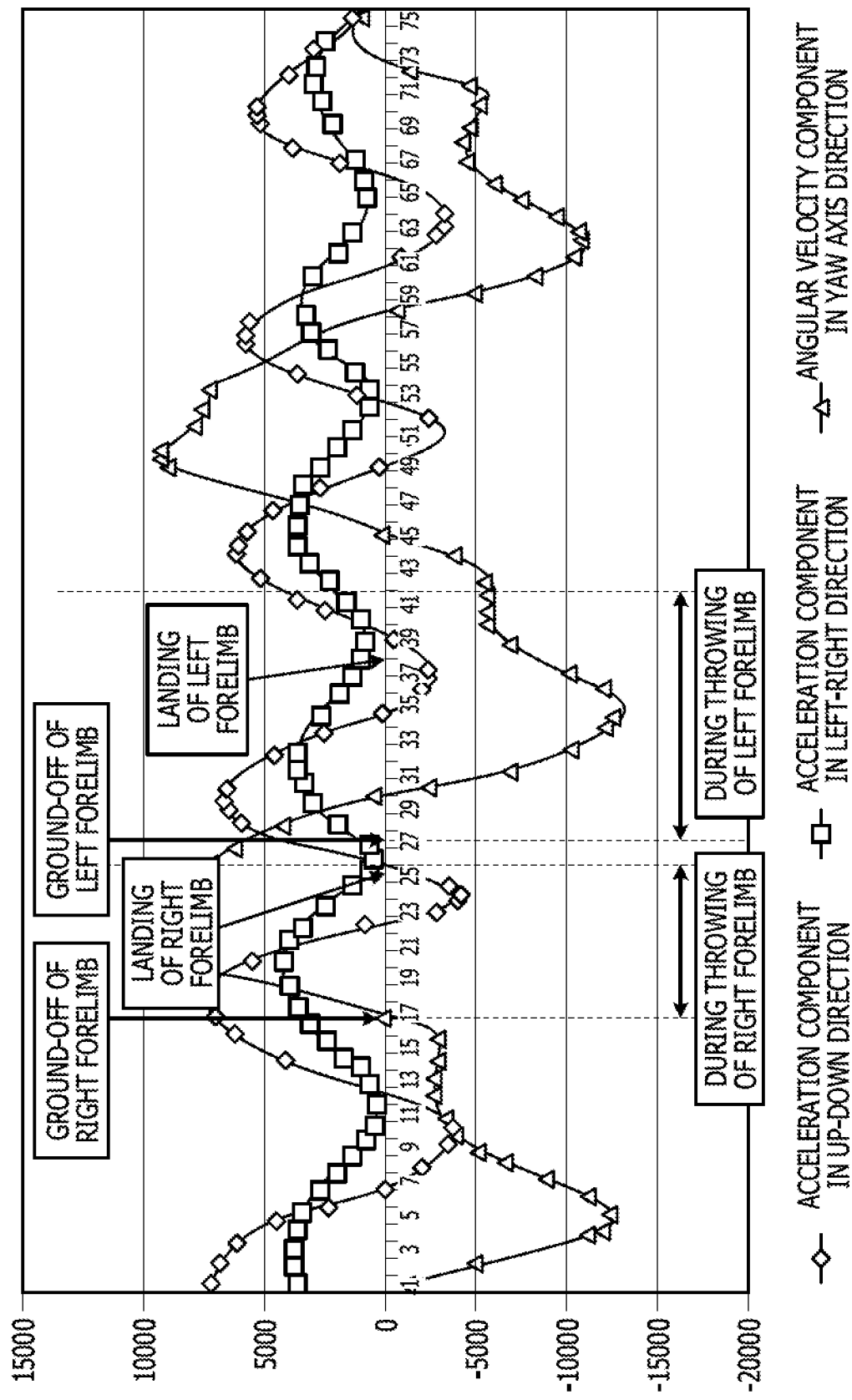

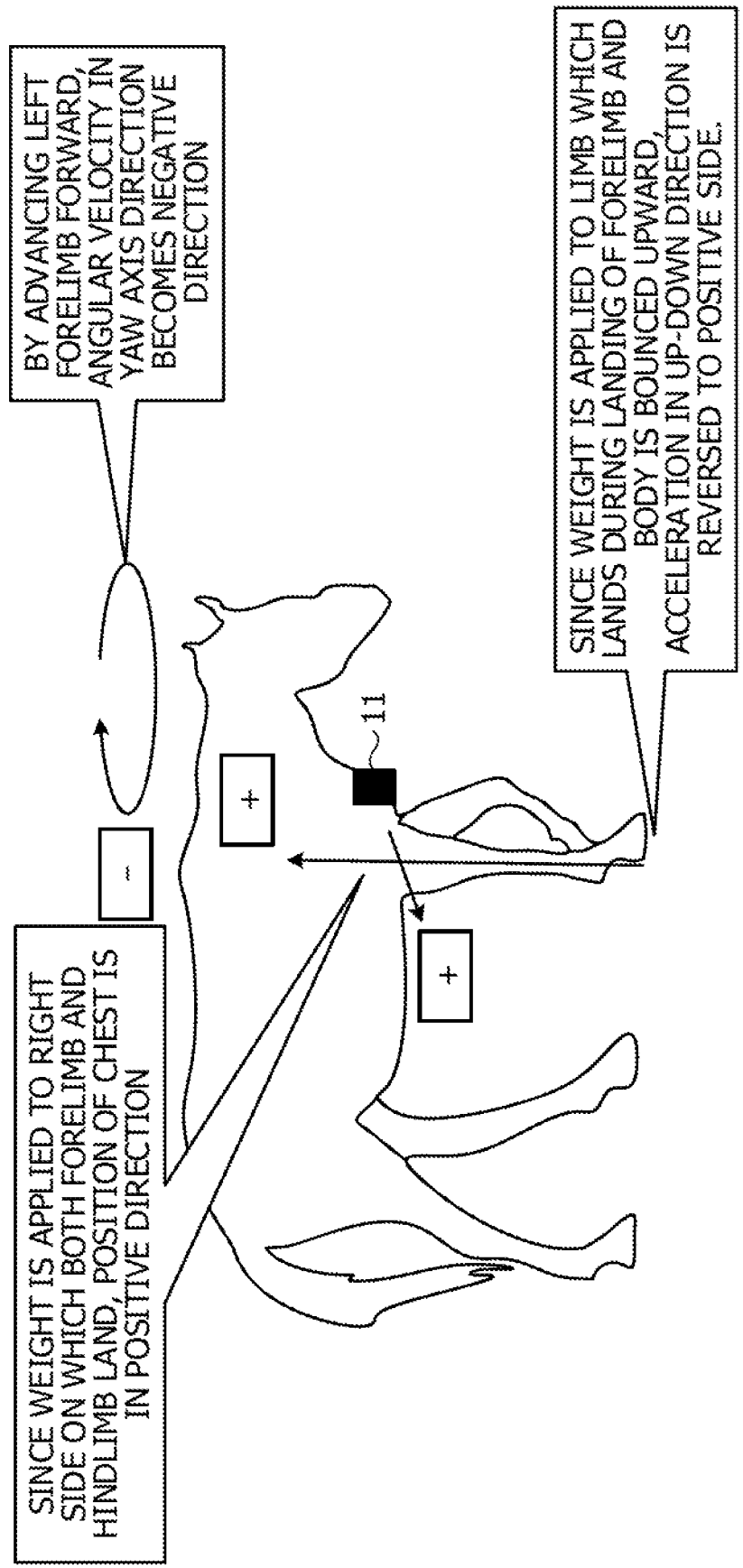

ESTIMATION METHOD, INFORMATION PROCESSING APPARATUS, AND NON-TRANSITORY COMPUTER-READABLE STORAGE MEDIUM FOR ESTIMATING MOTION OF ANIMAL

CROSS-REFERENCE TO RELATED APPLICATION

This application is a continuation application of International Application PCT/JP2016/056146, filed on Feb. 29, 2016 and designated the U.S., the entire contents of which are incorporated herein by reference.

FIELD

The present invention relates to an estimation method, an information processing apparatus, and non-transitory computer-readable storage medium for estimating a motion of an animal.

BACKGROUND

For general horses represented by thoroughbred, health management has the following problems. Generally, training which imposes a load on the mind and body of a horse is performed in order to improve the ability of a horse. However, as horses are also creatures, physical conditions of the horses change day by day. One irregularity of the body condition of a horse is an abnormal gait state which is called lameness. Lameness is known to occur due to the generation of some abnormalities in four limbs of the horse, but in a case where the lameness is minor, there is a case where it is difficult to find the lameness. When the lameness in a minor state and a strong training is performed with respect to the horse having lameness, there is a case where more severe disorders, such as tendinitis, are caused. Therefore, it is desirable for horse health management to find lameness in an early stage and in a minor stage, to refrain from training, and to take treatment.

Examples of the related art include Japanese National Publication of International Patent Application No. 2008-500046.

SUMMARY

According to an aspect of the invention, an estimation method performed by a computer, the method comprising: distinguishing ground-off and landing timings of respective four limbs of an animal based on measurement data acquired by using a motion sensor attached to the animal which has four limbs, and identifying a limb which interlocks with a disorder of a motion waveform upon a motion of the animal, based on the distinguished ground-off and landing timings of each of the four limbs of the animal.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 12A illustrates a diagram illustrating an example of a distribution ratio of the left and right balance.

FIG. 12B illustrates a diagram illustrating an example of the distribution ratio of the left and right balance.

FIG. 13 illustrates a diagram illustrating an example of a transition of evaluation results of the left and right balance for each walking completion for a plurality of times of walking completions.

FIG. 15 illustrates a diagram schematically illustrating a positional relationship of four limbs when the horse moves.

FIG. 18B illustrates a diagram illustrating an example of a motion waveform of acceleration in the up-down direction and a motion waveform of an angular velocity in the yaw axis direction in a case where lameness occurs.

FIG. 19A illustrates a diagram illustrating an example of motion waveforms in a case where lameness occurs.

FIG. 19B illustrates a diagram illustrating another example of motion waveforms in a case where lameness occurs.

FIG. 20 illustrates a view illustrating the movement of the horse when moving in walk.

FIGS. 28A-1 and 28A-2 illustrate a flowchart illustrating an example of a procedure of estimation processing.

FIGS. 28C-1 and 28C-2 illustrate a flowchart illustrating an example of a procedure of estimation processing.

DESCRIPTION OF EMBODIMENT

Figure 1:
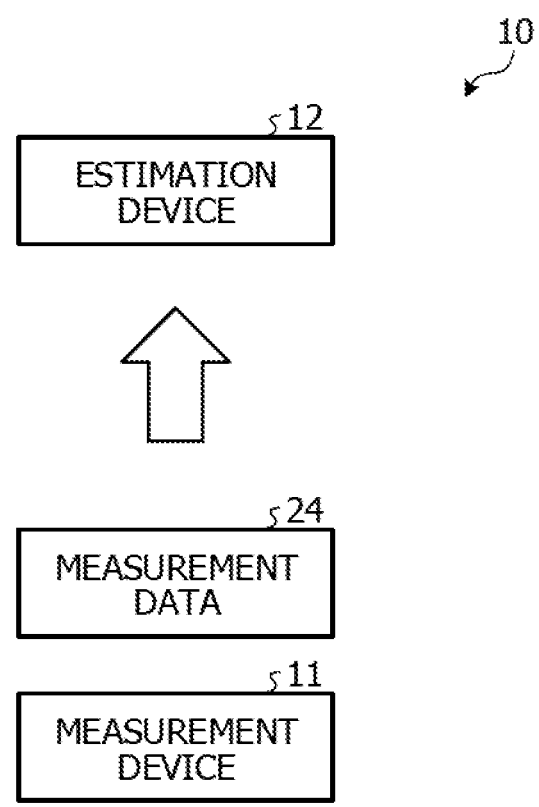
FIG. 1 illustrates a diagram illustrating an example of a schematic configuration of a system.

In the related art, the lameness has been found by experience and intuition of a person who manages a horse. However, as described above, there is a case where it is not possible to distinguish a minor lameness from a healthy state. In addition, in a case where the person who manages a horse is inexperienced, there is also a concern that the person misses a thing that can be found by a person who is experienced. Furthermore, since the person who manages a horse usually manages a plurality of horses at the same time, there is also a concern of missing minor irregularities of each horse. According to this, there is a case where more serious disorders are caused by performing inappropriate training with respect to the horse while missing a minor lameness in the early stage.

Furthermore, in a case where the lameness is detected, more experience and intuition of experts are demanded to identify a limb having a problem which is a target to be treated. Animals are not capable of telling humans which limb is painful. Experts identify a limb having a problem by looking at the steps or by touching the limbs. In a case where the problem is still unknown, the limb having a problem is identified, for example, by using diagnostic anesthesia. In the method using diagnostic anesthesia, anesthesia is applied to a limb which is considered as a limb having a problem, and the limb is determined as a corresponding limb when the horse no longer hurts. However, in the method using diagnostic anesthesia, it is demanded to anesthetize the limbs of the horse, and this imposes a heavy burden on the horse.

In recent years, western countries have introduced a method of identifying a limb having a problem using nuclear scintigraphy. In the method using nuclear scintigraphy, a radioactive isotope is used as a reagent for testing. Therefore, in the method using nuclear scintigraphy, it is demanded to pay attention to the handling of the reagents, excrement or bedding straws of horses at the time of diagnosis are handled as nuclear waste, and thus, building facilities that satisfy safety standards demands a large amount of money and site. Therefore, although a high effect of the method is known, the method has not been introduced in Japan.

In addition, the lameness of horses was described, but lameness occurs in all animals moving on four limbs, such as cattle and dogs, because some abnormalities are generated in four limbs.

In one aspect, an object of the present invention is to provide an estimation program, an estimation method, and an information processing apparatus which are capable of estimating a limb having a problem that causes lameness in a state where the burden on an animal moving on four limbs is small.

Hereinafter, examples of an estimation program, an estimation method, and an information processing apparatus according to the present invention will be described in detail with reference to the drawings. In addition, the disclosed technology is not limited by the examples. Further, the following examples may be appropriately combined with each other within a range that does not cause contradiction.

Example 1

[System Configuration]

First, an example of a system for performing health management according to Example 1 will be described. FIG. 1 illustrates a diagram illustrating an example of a schematic configuration of the system. A system 10 is a system for detecting lameness of animals moving on four limbs, such as horses, cattle, and dogs. Hereinafter, as an animal moving on four limbs, a case of detecting lameness of a horse will be described as an example.

Training which imposes a load on the mind and body of the horse is performed in order to improve the ability of the horse. In particular, it is important for a light breed horse, such as thoroughbred, to perform the training while appropriately performing body condition management and suppressing the occurrence of failures. Therefore, for the light breed horse, it is demanded to find lameness in an early stage and in a minor stage. In the example, the system 10 supports detection of lameness of the horse.

As illustrated in FIG. 1, the system 10 includes a measurement device 11 and an estimation device 12. The measurement device 11 is a device which is attached to the horse and measures the behavior when the horse moves on four limbs. For example, the measurement device 11 has a motion sensor embedded therein and measures the behavior of the horse when moving on four limbs by the motion sensor. The measurement device 11 stores measurement data 24 measured by the motion sensor. The measurement device 11 and the estimation device 12 are capable of exchanging data via wired communication, wireless communication, or a storage medium, such as a flash memory. The measurement data 24 measured by the measurement device 11 is sent to the estimation device 12 via wired communication, wireless communication, or storage medium.

The estimation device 12 is a device which estimates a limb having a problem that causes lameness in a case where lameness occurs based on the measurement data 24. The estimation device 12 is, for example, a computer, such as a personal computer or a server computer. The estimation device 12 may be a portable terminal device, such as a tablet terminal, a smartphone, or a personal digital assistant (PDA). For example, the estimation device 12 is disposed at a management source, such as stables and ranches for managing horses. The estimation device 12 may be implemented as a single computer or may be implemented by a plurality of computers. In addition, in the example, a case where each of the estimation devices 12 is a single computer, will be described as an example. In the example, the estimation device 12 corresponds to the information processing device.

Figure 2:
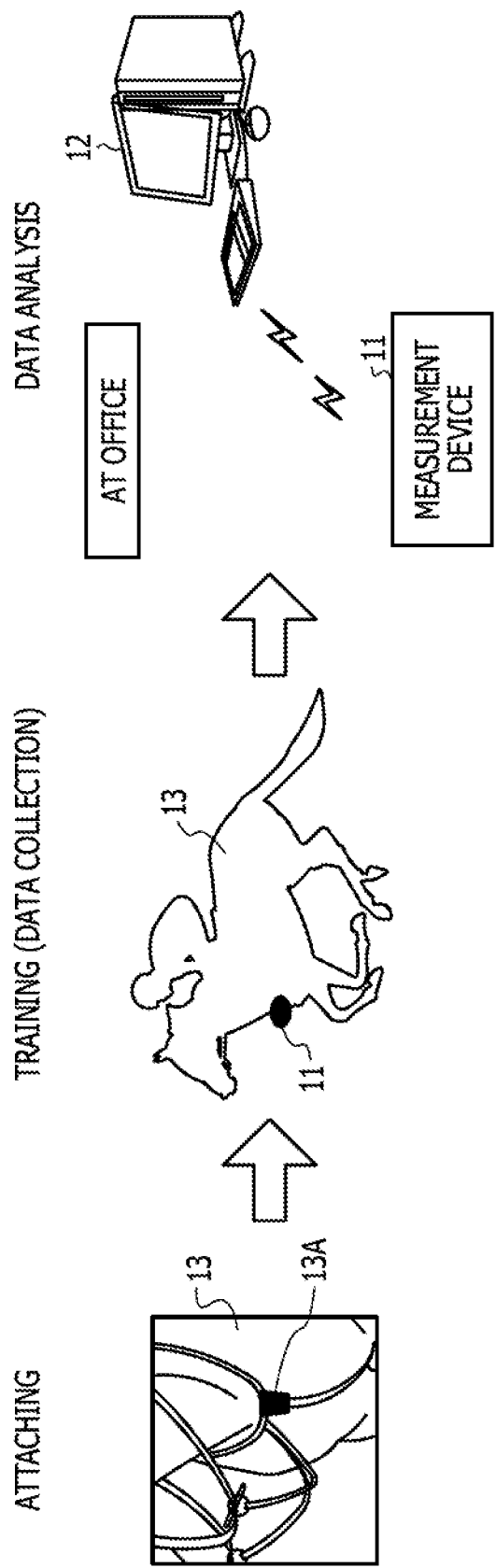
FIG. 2 illustrates a view illustrating an example of a flow of health management of a horse by a system according to Example 1.

Next, an example of a flow of health management of a horse using the system 10 according to Example 1 will be described. FIG. 2 is a view illustrating an example of a flow of health management of a horse by the system according to Example 1. The measurement device 11 is attached in front of the chest of a horse 13 which is a target of health management. For example, the measurement device 11 is stored in a harness 13A attached to the horse 13. In the example of FIG. 2, an example in which the measurement device 11 is attached in front of the chest of the horse 13 using a martingale is illustrated. The horse 13 performs various types of training in a state where the measurement device 11 is attached thereto. The measurement device 11 collects data on the behavior during the training by the motion sensor and stores the measurement data 24.

Here, lameness occurs due to the generation of some abnormalities in the four limbs of the horse, and is in a state of so-called, dragging limbs. Since the horse in which the lameness occurs hides the limb in which the lameness occurs, a left and right balance tends to collapse. In order to detect the left and right balance of the horse, it is considered to attach the motion sensor to the limb of the horse. However, when the motion sensor is attached to the limb of the horse, a burden is applied to the limb due to the weight of the motion sensor or the like, and there is a concern of causing a failure. In addition, it is also considered to attach the motion sensor to the head of the horse. However, in the head, the influence of the movement of the neck, such as shaking the neck, is large, and it is difficult to detect the left and right balance of the horse. Meanwhile, since the chest of the horse moves being interlocked with the forelimb, it is easy to detect the left and right balance of the horse. Here, in the system 10 according to the example, the measurement device 11 is attached in front of the chest of the horse 13 and the movement of the chest of the horse 13 is measured.

After the training, the measurement device 11 is brought to the management office, and the stored measurement data 24 is uploaded to the estimation device 12 via the storage medium or by wired communication or wireless communication. Based on the uploaded measurement data 24, the estimation device i12 evaluates whether or not the lameness occurs, and in a case where the lameness occurs, the limb having a problem that causes the lameness is estimated.

[Configuration of Measurement Device]

Figure 3:
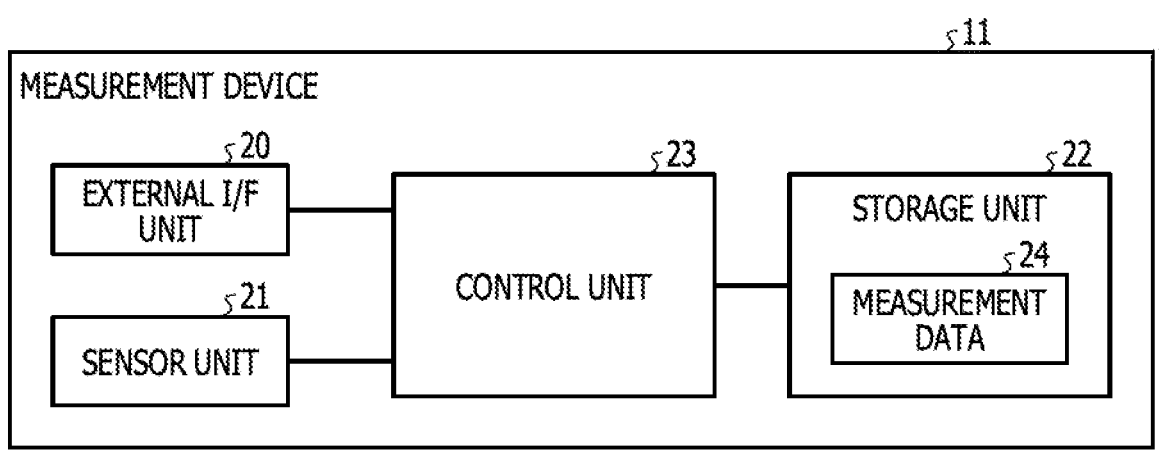
FIG. 3 illustrates a diagram illustrating an example of a functional configuration of a measurement device according to Example 1.

Next, the configuration of each device will be described. First, the configuration of the measurement device 11 will be described. FIG. 3 is a view illustrating an example of a functional configuration of the measurement device according to Example 1. As illustrated in FIG. 3, the measurement device 11 includes an external I/F (interface) unit 20, a sensor unit 21, a storage unit 22, and a control unit 23.

The external I/F unit 20 is, for example, an interface for transmitting and receiving various types of information to and from other devices. In the measurement device 11 according to Example 1, the external I/F unit 20 is a port for inputting and outputting the data to and from the storage medium, such as a flash memory, a communication port for performing wired communication by a cable or the like, or a communication interface for performing wireless communication.

The sensor unit 21 is the motion sensor which detects the behavior. For example, the sensor unit 21 is a six-axis sensor which measures accelerations in three axial directions perpendicular to each other and angular velocities of the three axes. In addition, the sensor unit 21 may be divided into a plurality of sensors. For example, the sensor unit 21 may be configured with a triaxial acceleration sensor for measuring accelerations in three axial directions and a gyro sensor for measuring angular velocity of three axes.

The storage unit 22 is a semiconductor memory, such as a random access memory (RAM), a flash memory, or a non volatile static random access memory (NVSRAM), which can rewrite the data. In addition, the storage unit 22 may be a storage device, such as a hard disk, a solid state drive (SSD), or an optical disk. The storage unit 22 stores an operating system (OS) executed by the control unit 23 or various programs. Furthermore, the storage unit 22 stores various types of information. For example, the storage unit 22 stores the measurement data 24.

The measurement data 24 is data which stores various types of information on the behavior of the horse therein. For example, in the measurement data 24, values of accelerations in three axial directions and angular velocities of three axes which are measured by the sensor unit 21 are stored in association with measurement times.

The control unit 23 is a device which controls the entire measurement device 11. As the control unit 23, it is possible to adopt an electronic circuit, such as a central processing unit (CPU), a micro processing unit (MPU) and the like, or an integrated circuit, such as an application specific integrated circuit (ASIC), a field programmable gate array (FPGA) and the like.

The control unit 23 stores various types of data respectively detected by the sensor unit 21 in the measurement data 24. For example, the control unit 23 measures accelerations in three axial directions and angular velocities of three axes by the sensor unit 21 at a predetermined cycle. Each time the measurement is performed, the control unit 23 associates the values of accelerations in three axial directions and the angular velocities of three axes with the measurement times and stores the association result in the measurement data 24. The measurement time can also be an elapsed time starting from the time when the measurement is started or may be a global time measured by a time stamp or the like. In a case where the measurement time is set as the elapsed time, the measurement data 24 in which the measurement start date and time at which the measurement is started is embedded in a header is stored in the storage unit 22. In addition, hereinafter, a case where the accelerations in three axial directions and angular velocities of three axes are measured in a cycle of 0.05 seconds is assumed, but the measurement cycle is not limited thereto.

[Configuration of Estimation Device]

Figure 4:
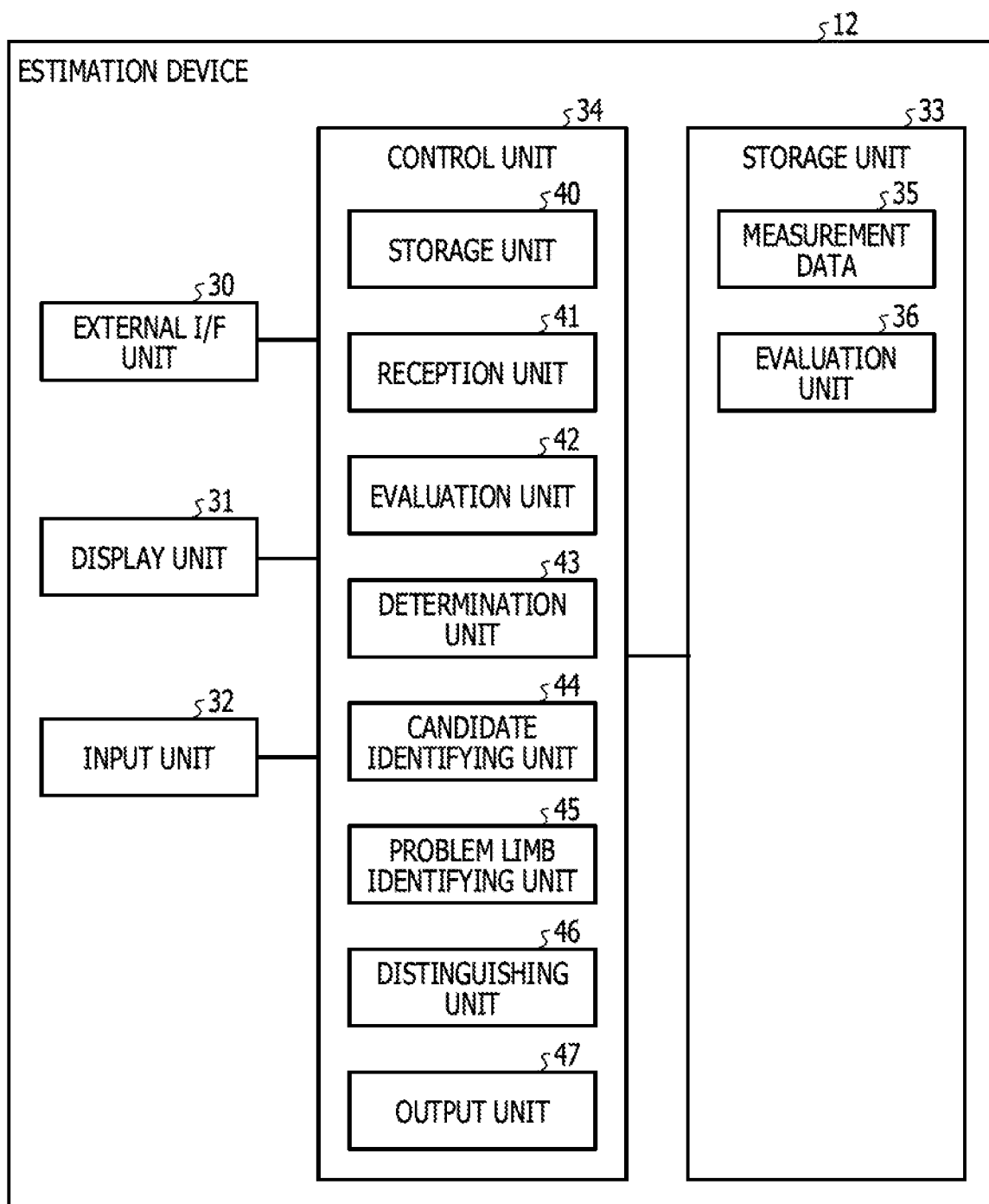
FIG. 4 illustrates a diagram illustrating an example of a functional configuration of an estimation device according to Example 1.

Next, the configuration of the estimation device 12 will be described. FIG. 4 illustrates a diagram illustrating an example of a functional configuration of the estimation device according to Example 1. As illustrated in FIG. 4, the estimation device 12 includes an external I/F unit 30, a display unit 31, an input unit 32, a storage unit 33, and a control unit 34.

The external I/F unit 30 is, for example, an interface for transmitting and receiving various types of information to and from other devices. In the estimation device 12 according to Example 1, the external I/F unit 30 is a port for inputting and outputting the data to and from the storage medium, such as a flash memory, a communication port for performing wired communication by a cable or the like, or a communication interface for performing wireless communication. For example, the external I/F unit 30 receives the measurement data 24 from the measurement device 11 by a storage medium, wired communication, or wireless communication.

The display unit 31 is a display device for displaying various types of information. As the display unit 31, a display device, such as a liquid crystal display (LCD) or a cathode ray tube (CRT), can be employed. The display unit 31 displays various types of information. For example, the display unit 31 displays various screens, such as an operation screen.

The input unit 32 is an input device for inputting various types of information. As the input unit 32, an input device that receives an input of an operation, such as a mouse or a keyboard, can be employed. In addition, the input unit 32 may be various types of buttons provided in the estimation device 12 or a transmission type touch sensor provided on the display unit 31. The input unit 32 receives the input of various types of information. For example, the input unit 32 receives various operation inputs related to evaluation, such as an instruction to start processing. The input unit 32 receives an operation input from a user and inputs operation information indicating the received operation contents to the control unit 34. In addition, in the example of FIG. 4, since the functional configuration is illustrated, the display unit 31 and the input unit 32 are separately provided, but for example, a device in which the display unit 31 and the input unit 32, such as a touch panel, are integrally provided may be configured.

The storage unit 33 is a storage device for storing various types of data. For example, the storage unit 33 is a storage device, such as a hard disk, an SSD, or an optical disk. In addition, the storage unit 33 may be a semiconductor memory, such as RAM, flash memory, or NVSRAM, which can rewrite the data.

The storage unit 33 stores an operating system (OS) executed by the control unit 34 or various programs. Furthermore, the storage unit 33 stores various types of information. For example, the storage unit 33 stores measurement data 35 and evaluation data 36.

The measurement data 35 is data that stores the measurement data 24 acquired from the measurement device 11 therein. The evaluation data 36 is data in which the evaluation result of the measurement data 35 is stored.

The control unit 34 is a device which controls the estimation device 12. As the control unit 34, it is possible to adopt an electronic circuit, such as a CPU, an MPU and the like, or an integrated circuit, such as an ASIC, a FPGA and the like. The control unit 34 has an internal memory for storing programs defining various processing procedures or control data, and executes various types of processing by the programs or control data. The control unit 34 functions as various processing units by operating various programs. For example, the control unit 34 includes a storage unit 40, a reception unit 41, an evaluation unit 42, a determination unit 43, a candidate identifying unit 44, a problem limb identifying unit 45, a distinguishing unit 46, and an output unit 47.

The storage unit 40 stores various types of data. For example, the storage unit 40 stores the measurement data 24 acquired from the measurement device 11 via the external I/F unit 30 as the measurement data 35 in the storage unit 33.

The reception unit 41 receives various types of information. For example, the reception unit 41 receives various operation instructions. For example, the reception unit 41 displays various screens, such as an operation screen, on the display unit 31, and receives an operation instruction, such as an instruction to start processing of the measurement data 35, from the input unit 32.

The evaluation unit 42 performs various evaluations. For example, the evaluation unit 42 evaluates the left and right balance of the movement of the horse for each walking completion based on the measurement data 35. Hereinafter, the evaluation method will be described in detail.

First, the evaluation unit 42 obtains a trajectory of a position in front of the chest of the horse for each walking completion based on the measurement data 35. Here, the accelerations in the three axial directions at each measurement time stored in the measurement data 35 include vibration components caused by the movement on four limbs of the horse and gravity components due to gravity. The vibration component corresponds to one walking completion of the horse, and fluctuates cyclically. Meanwhile, the gravity component is mostly fixed. Therefore, with respect to a change in accelerations in three axial directions, when passing through a low-pass filter (LPF) or a high-pass filter (HPF) with an appropriate cutoff frequency, the vibration component of the horse and the gravity component can be separated from each other. The direction of the gravity component is a vertical direction. In addition, the evaluation unit 42 may separate the gravity component at the accelerations in three axial directions at each measurement time through the low-pass filter, and may set the component of the difference obtained by subtracting the gravity component from the accelerations in the three axial directions at each measurement time as a vibration component caused by the movement of the horse.

Here, the gait when the horse moves is roughly divided into walk, trot, canter, and gallop. Since the velocity of the gait of the horse is high in the order of walk, trot, canter, and gallop, and the vibration when the horse runs is also large, a change in accelerations in three axial directions also increases. In addition, in trot, canter, and gallop, the body of the horse is in a state of floating during one walking completion, and a zero gravity state where there is no acceleration in three axial directions is generated. Therefore, the evaluation unit 42 separates the gravity component using the data in the period during which the change in acceleration in the three axial directions is small.

Figure 5:
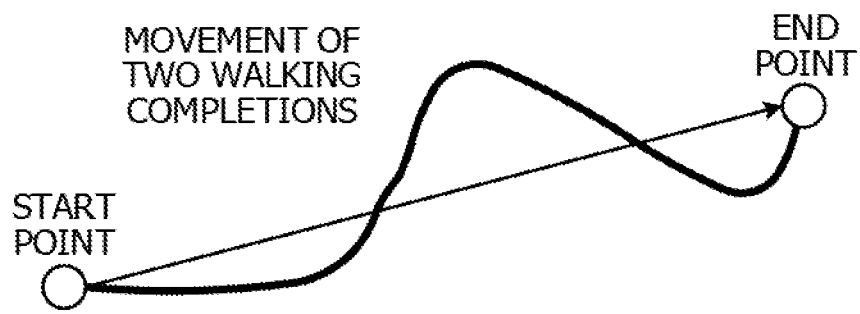
FIG. 5 illustrates a view illustrating an example of a trajectory of a position.
Figure 6:
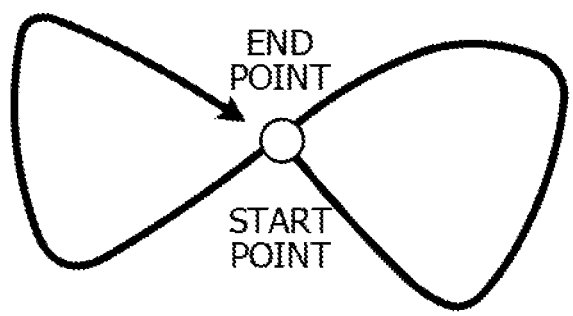
FIG. 6 illustrates a view illustrating an example of a trajectory of a position in front of the chest of the horse on a plane.

In addition, the evaluation unit 42 obtains the trajectory of the position in front of the chest of the horse using the vibration component caused by the movement of the horse and the angular velocities of the three axes among the accelerations in the three axial directions at each measurement time. For example, the evaluation unit 42 calculates the three-dimensional position of each measurement time using the vibration component caused by the movement of the horse in the three axial directions at each measurement time and the angular velocities of three axes. Accordingly, the trajectory of the three-dimensional position is obtained. FIG. 5 is a view illustrating an example of the trajectory of the position. The evaluation unit 42 identifies a plurality of feature points having the same features in the vibration components measured from each position. For example, the evaluation unit 42 identifies a point at which the vibration becomes maximum, a point at which the acceleration in the vertical direction becomes maximum, and the like, as feature points. In the example of FIG. 5, the start point and the end point are identified as feature points. The evaluation unit 42 converts the coordinates on the plane such that the positions between the feature points are the same as the feature points, and obtains the trajectory of the position on the plane. For example, the evaluation unit 42 projects the position between the feature points on a perpendicular plane connecting the feature points, and obtains the trajectory of the position in front of the chest of the horse on the plane when the horse is viewed from the front. In the example of FIG. 5, the coordinates of each position between the start point and the end point are projected on a perpendicular plane connecting the position of the start point and the position of the end point, and obtains the trajectory of the position in front of the chest of the horse on the plane. FIG. 6 is a view illustrating an example of the trajectory of the position in front of the chest of the horse on a plane. In the example of FIG. 6, the start point and the end point of the trajectory are the same position.

In addition, a method for obtaining the trajectory of the position in front of the chest of the horse on the plane is not limited thereto. For example, the evaluation unit 42 obtains the up-down direction of the horse, the left-right direction of the horse, the front-rear direction of the horse using the features of walking of the horse from the accelerations in the three axial directions and the angular velocities of three axes which are stored in the measurement data 35. In addition, the evaluation unit 42 may obtain the trajectory on the plane using the vibration component in the up-down direction of the horse and the vibration component in the left-right direction of the horse. For example, the evaluation unit 42 separates the vibration component in the up-down direction from the vibration component due to the movement of the horse considering the component in the vertical direction as the up-down direction of the horse. In addition, in a case where the moving velocity of the horse is in a steady state, the movement of the horse is large in the left-right direction and small in the front-rear direction. Here, the evaluation unit 42 obtains the direction in which the vibration is the largest as the left-right direction of the horse among the directions perpendicular to the vertical direction, among the vibration components due to the movement of the horse excluding the vibration component in the up-down direction. In addition, the evaluation unit 42 obtains the direction perpendicular to the up-down direction of the horse and the left-right direction of the horse as the front-rear direction of the horse. The evaluation unit 42 may separate the vibration component in the left-right direction of the horse and the vibration component in the front-rear direction of the horse from the vibration component caused by the movement of the horse, and may obtain the trajectory on the plane when the horse is viewed from the front using the vibration component in the left-right direction and the vibration component in the front-rear direction. For example, the evaluation unit 42 obtains the acceleration in the front-rear direction, the acceleration in the left-right direction, and acceleration in the up-down direction, from the accelerations in the three axial directions and the angular velocities of three axes which are stored in the measurement data 35.

Further, the evaluation unit 42 obtains the acceleration in the yaw direction around the up-down direction, from the accelerations in the three axial directions and the angular velocities of the three axes which are stored in the measurement data 35. In addition, the evaluation unit 42 may obtain the acceleration in a pitching direction around the left-right direction and the acceleration in a rolling direction around the front-rear direction. In addition, the evaluation unit 42 may obtain the trajectory on the plane when the horse is viewed from the front, using the acceleration in the left-right direction and the acceleration in the up-down direction. In addition, a method for obtaining the up-down direction, the left-right direction, and the front-rear direction of the horse is not limited thereto. For example, a method described in "Japanese Laid-open Patent Publication No. 2015-84943" disclosed by the present applicant may be used.

Figure 7:
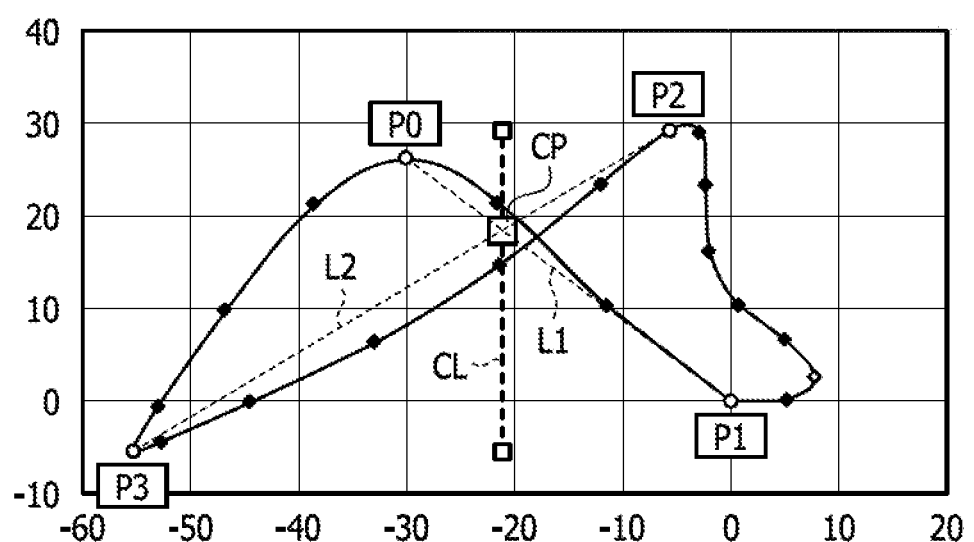
FIG. 7 illustrates a diagram illustrating an example of the trajectory of the position in front of the chest of the horse.

The evaluation unit 42 evaluates the left and right balance of the movement of the horse using the trajectory of the position in front of the chest of the horse on the plane. FIG. 7 illustrates a diagram illustrating an example of the trajectory of the position in front of the chest of the horse. In the example of FIG. 7, the horizontal axis represents the movement amount in the horizontal direction in a unit of mm, and is assumed to be an X axis. The vertical axis represents the movement amount in the up-down direction in a unit of mm, and is assumed to be a Y axis. In the example, since the left and right balance is evaluated from the amount of change in position of the point, either the X axis or the Y axis reference (a point that becomes 0) may be used. In the example of FIG. 7, the trajectory in a case where the gait of the horse is a trot is illustrated. In the trajectory illustrated in FIG. 7, it is assumed that the order of measurement times is point P0→point P1→point P2→point P3. As illustrated in FIG. 7, in general, the trajectory of the position in front of the chest draws a shape of ∞ (a figure of 8 in the horizontal direction) in many cases. It can be considered that this is because, when the horse walks, the head is moved in the shape of figure 8 to keep balance. Meanwhile, in a case where the lameness occurs in the horse, the trajectory collapses from the shape of ∞ in order to hide the limb in which the lameness occurs. Here, the evaluation unit 42 evaluates the left and right balance of the trajectory. Hereinafter, a method for evaluating the left and right balance of the trajectory will be described in detail.

The evaluation unit 42 obtains the point P0 which is a maximum point on the left side, the point P1 which is a minimum point on the right side, the point P2 which is a maximum point on the right side, and the point P3 which is a minimum point on the left side, in the trajectory of the position in front of the chest. For example, the evaluation unit 42 compares the coordinates of the position of each point in the order of the measurement times, and distinguishes the maximum point at which the position of the next point in the up-down direction drops for the first time and the minimum position at which the position of the next point in the up-down direction rises for the first time in order. In addition, in a case where the point determined as the minimum point after the maximum point is on the right side of the maximum point, the evaluation unit 42 identifies the maximum point as the maximum point on the left side, and identifies the minimum point as the minimum point on the right side. In addition, in a case where the point determined as the minimum point after the maximum point is on the left side of the maximum point, the evaluation unit 42 identifies the maximum point as the maximum point on the right side, and identifies the minimum point as the minimum point on the left side. As a method for identifying the maximum points on the left side and on the right side, it may be determined that the maximum point is on the left side when the X coordinate of the maximum point is smaller than the X coordinate of an intersection point CP, and the maximum point is on the right side when the X coordinate of the maximum point is larger than the X coordinate of the intersection point CP. The trajectory of point P0→point P1→point P2→point P3→point P0 illustrated in FIG. 7 corresponds to one walking completion. The evaluation unit 42 repeatedly identifies point P0→point P1→point P2→point P3→point P0 . . . , and obtains the trajectory for each walking completion. In addition, the point which is considered as the start point of the trajectory of one walking completion may be any one of the points P0 to P3.

The evaluation unit 42 evaluates the left and right balance of the trajectory for each walking completion. For example, the evaluation unit 42 obtains a line segment L1 which connects the point P0 and the point P1 to each other and a line segment L2 which connects the point P2 and the point P3 to each other. The evaluation unit 42 obtains the intersection point CP of the line segment L1 and the line segment L2.

For example, the XY coordinates of the point P0 are (P0.X, P0.Y), the XY coordinates of the point P1 are (P1.X, P1.Y), the XY coordinates of the point P2 are (P2.X, P2.Y), and the XY coordinates of the point P3 are (P3.X, P3.Y). In this case, the XY coordinates (intersection point.X, intersection point.Y) of the intersection point CP are obtained from the following.

$A = P1.Y - P0.Y$ $B = P0.X - P1.X$ $U = (P1.Y - P0.Y) \times P0.X - (P1.X - P0.X) \times P0.Y$ $C = P3.Y - P2.Y$ $D = P2.X - P3.X$ $V = (P3.Y - P2.Y) \times P2.X - (P3.X - P2.X) \times P2.Y$ Intersection point.$X = (D \times U - B \times V)/(A \times D - B \times C)$ Intersection point.$Y = (A \times V - C \times U)/(A \times D - B \times C)$ The evaluation unit 42 obtains a perpendicular center line CL of the up-down direction passing through the intersection point CP. In addition, the evaluation unit 42 calculates an indicator 1 indicating the left and right area ratio of the trajectory with respect to the center line CL. Further, the evaluation unit 42 calculates an indicator 2 indicating a ratio of the length of the part at which the line segment L1 and the line segment L2 are on the left side to the length of the part at which the line segment L1 and the line segment L2 are on the right side with respect to the center line CL. Further, the evaluation unit 42 calculates an indicator 3 indicating a ratio of decrease amounts of the point P1 and the point P3 from the intersection point CP. In addition, the indicators 1 to 3 are examples, and any indicator may be used as long as the left and right balance of the trajectory is indicated. Hereinafter, a method for obtaining the indicators 1 to 3 will be described in detail.

Figure 8:
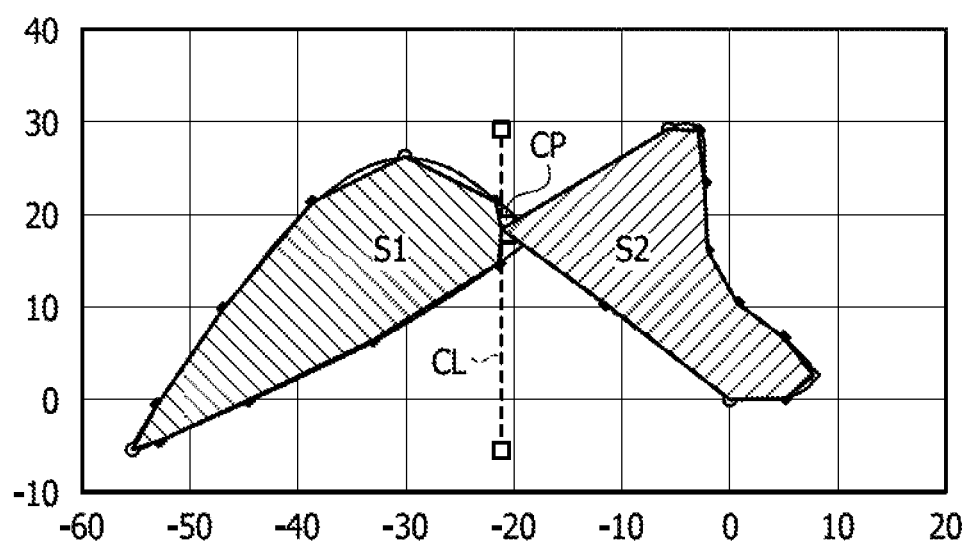
FIG. 8 illustrates a diagram illustrating an example of left and right areas of the trajectory with respect to a center line CL.

FIG. 8 illustrates a diagram illustrating an example of the left and right areas of the trajectory with respect to the center line CL. In the example of FIG. 8, an area S1 on the left side of the trajectory with respect to the center line CL and an area S2 on the right side of the trajectory with respect to the center line CL are illustrated. For example, when the number of points of the trajectory is N, and the coordinates of N points are $(x_j, y_j)$, the area S can be obtained from the following equation (1).

$$S = \frac{1}{2}\left|\sum_{j=1}^{n}(x_j - x_{j+1}) \times (y_j + y_{j+1})\right| \quad (1)$$

The evaluation unit 42 approximates an area of a polygon drawn by the point on the left side of the trajectory and the intersection point CP by substituting the coordinates of the point on the left side of the trajectory and the intersection point CP in the equation (1), as the area S1 on the left side of the trajectory. The evaluation unit 42 approximates an area of a polygon drawn by the point on the right side of the trajectory and the intersection point CP by substituting the coordinates of the point on the right side of the trajectory and the intersection point CP in the equation (1), as the area S2 on the right side of the trajectory. The evaluation unit 42 calculates the area S1 on the left side of the trajectory÷the area S2 on the right side of the trajectory, as the value of indicator 1.

Figure 9:
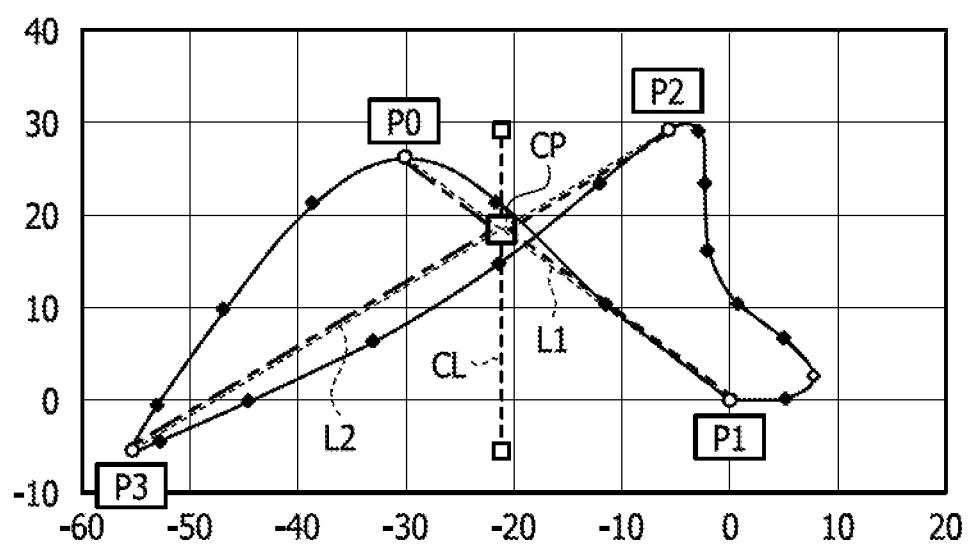
FIG. 9 illustrates a diagram illustrating an example of a part at which a line segment L1 and a line segment L2 are on the left side and a part at which a line segment L1 and a line segment L2 are on the right side with respect to the center line CL.

FIG. 9 illustrates a diagram illustrating an example of the part at which the line segment L1 and the line segment L2 are on the left side and the part at which the line segment L1 and the line segment L2 are on the right side with respect to the center line CL. In the example of FIG. 9, a one-dot chain line is given to the part at which the line segment L1 and the line segment L2 are on the left side with respect to the center line CL. In addition, a broken line is given to the part at which the line segment L1 and the line segment L2 are on the right side with respect to the center line CL. For example, in a case where the XY coordinates of a point A are (A.X, A.Y) and the XY coordinates of a point B are (B.X, B.Y), a line segment length (A, B) which is a length of the line segments between the point A and the point B is expressed by the following equation (2).

Line segment length$(A,B) = [(A.X - B.X)^2 + (A.Y - B.Y)^2]^{1/2}$ (2)

The evaluation unit 42 calculates the left line segment length of the part at which the line segment L1 and the line segment L2 are on the left side with respect to the center line CL from the following expression (3). In addition, the evaluation unit 42 calculates the right line segment length of the part at which the line segment L1 and the line segment L2 are on the right side with respect to the center line CL from the following expression (4).

Left line segment length: Line segment length(P0, intersection point)+Line segment length(P3, intersection point) (3)

Right line segment length: Line segment length(P2, intersection point)+Line segment length(P1, intersection point) (4)

The evaluation unit 42 calculates the left line segment length÷the right line segment length, as the value of the indicator 2.

Figure 10:
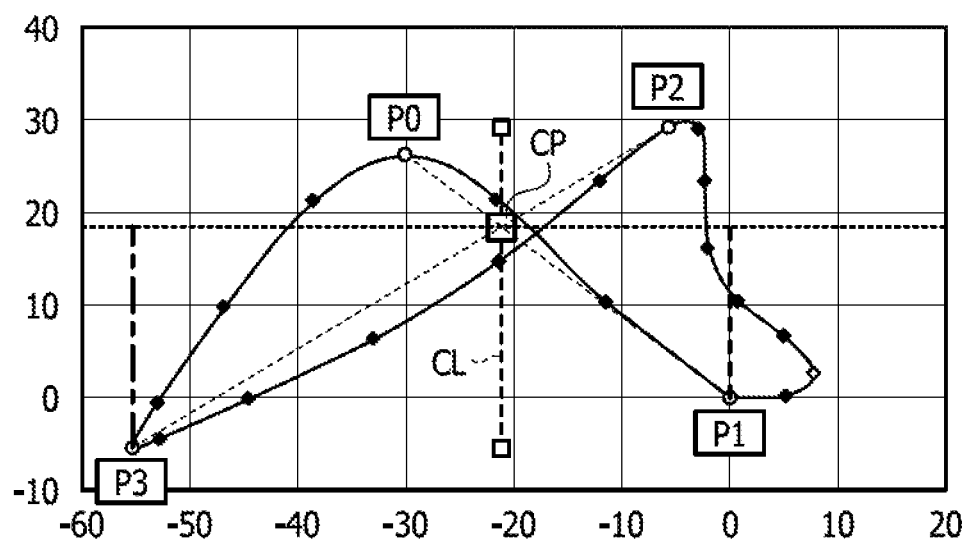
FIG. 10 illustrates a diagram illustrating an example of decrease amounts of a point P1 and a point P3 from an intersection point CP.

FIG. 10 illustrates a diagram illustrating an example of the decrease amounts of the point P1 and the point P3 from the intersection point CP. In the example of FIG. 10, a broken line is given to the part that becomes the decrease amount of the point P1 from the intersection point CP. In addition, a one-dot chain line is given to the part that becomes the decrease amount of the point P3 from the intersection point CP.

The evaluation unit 42 calculates the right decrease amount of the point P1 from the intersection point CP from the following expression (5). The evaluation unit 42 calculates the left decrease amount of the point P3 from the intersection point CP from the following expression (6).

Right decrease amount: |intersection point.$Y$–$P1.Y$| (5)

Left decrease amount: |intersection point.$Y$–$P3.Y$| (6)

The evaluation unit 42 calculates the left decrease amount÷the right decrease amount, as the value of the indicator 3.

The evaluation unit 42 evaluates the left and right balance of the trajectory by using the indicators 1 to 3 for each trajectory of one walking completion. For example, the evaluation unit 42 evaluates whether the balance is left or right by the indicators 1 to 3, respectively. Since the indicators 1 to 3 are ratios on the left side with respect to the right side, it is possible to evaluate that the balance collapses to the right side in a case where the ratio is less than 1, and that the balance collapses to the left side in a case where the ratio is larger than 1. The evaluation unit 42 evaluates the left and right balance of the movement by majority decision on which of the left and right balance is evaluated by the indicators 1 to 3.

Figure 11A:
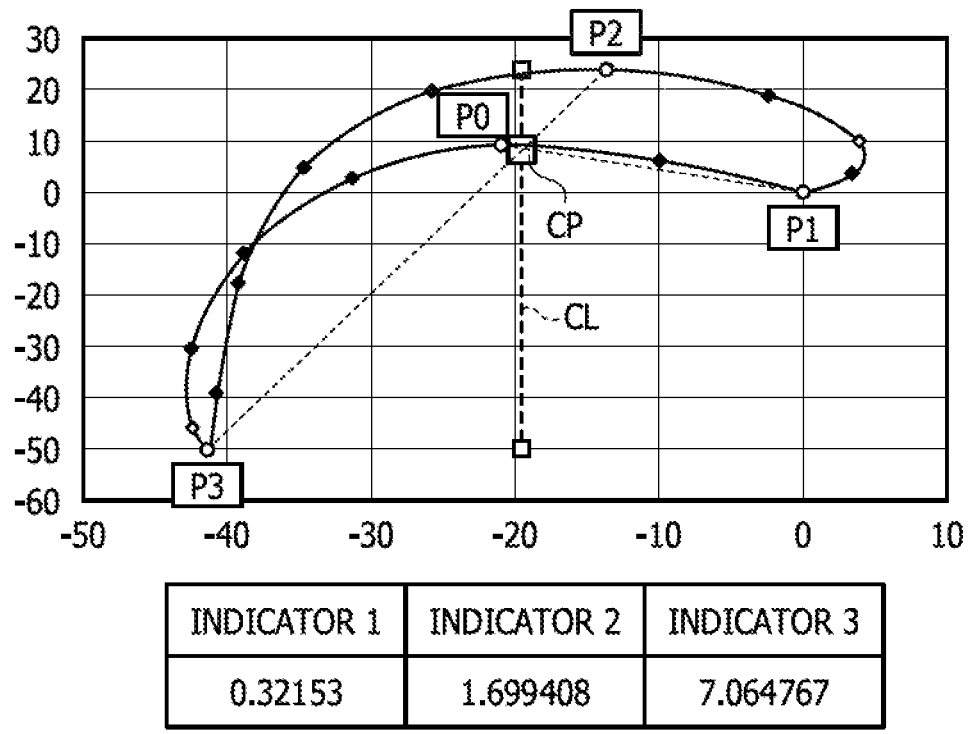
FIG. 11A illustrates a diagram illustrating an example in which it is not possible to appropriately evaluate a left and right balance.
Figure 11B:
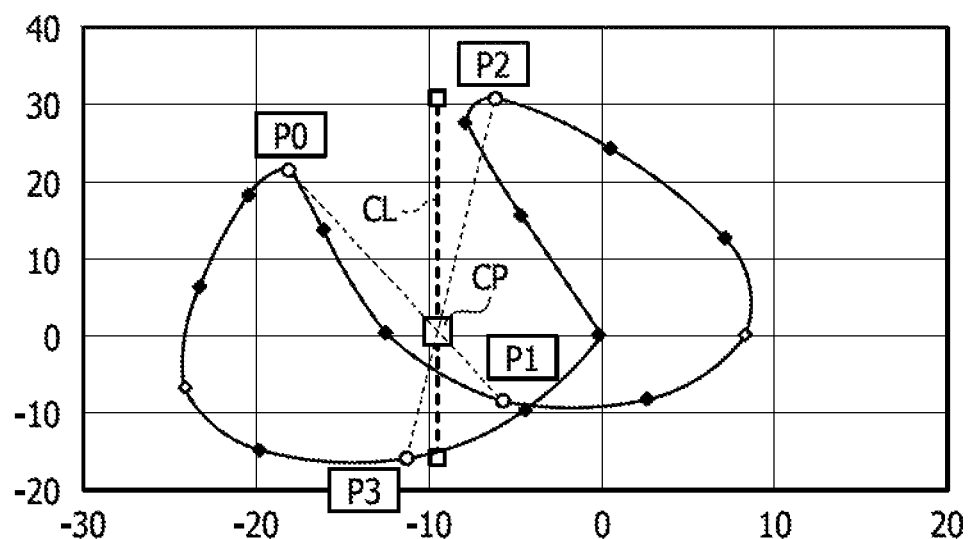
FIG. 11B illustrates a diagram illustrating an example in which it is not possible to appropriately evaluate the left and right balance.
Figure 11C:
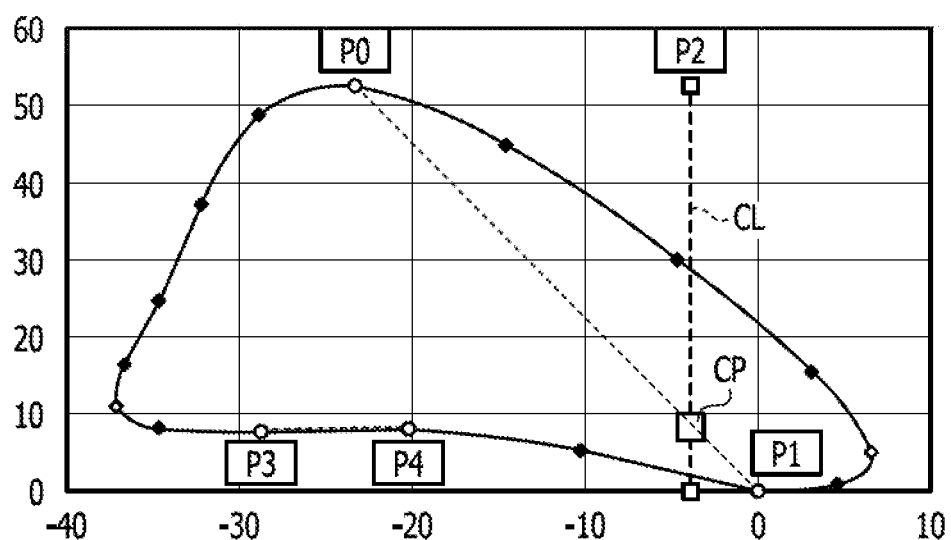
FIG. 11C illustrates a diagram illustrating an example in which it is not possible to appropriately evaluate the left and right balance.

Here, the left and right balance changes due to the change of the road surface or the motion of the horse during the walking, and the trajectory also changes. Therefore, there is a case where each of the indicators 1 to 3 is not capable of appropriately evaluating the left and right balance independently. FIGS. 11A to 11C are diagrams illustrating an example in which it is not possible to appropriately evaluate the left and right balance. In the example of FIG. 11A, only with the indicator 1, since the value is less than 1, it is determined that the balance collapses to the right side. However, in the example of FIG. 11A, the balance actually collapses to the left side, and correct determination is possible by using the indicator 2 and the indicator 3. In the example of FIG. 11B, only with the indicator 2, since the value is less than 1, it is determined that the balance collapses on the right side. However, in the example of FIG. 11B, the balance actually collapses to the left side, and correct determination is possible by using the indicator 1 and the indicator 3. In the example of FIG. 11C, only with the indicator 3, since the value is less than 1, it is determined that the balance collapses to the right side. However, in the example of FIG. 11C, the balance actually collapses to the left side, and correct determination is possible by using the indicator 1 and the indicator 2. In this manner, the evaluation unit 42 can evaluate the left and right balance of the movement with high accuracy by performing a majority decision on the evaluation of the indicators 1 to 3.

The determination unit 43 performs various determinations. For example, the determination unit 43 determines the gait of the horse based on the measurement data 35. For example, the determination unit 43 obtains a value α of the acceleration in the up-down direction and a square β of an absolute value of the acceleration from the measurement data 35, and using α and β, it is determined whether the gait when the horse moves is walk, trot, canter, or gallop. Since details of the determination of the gait are described in "Japanese Laid-open Patent Publication No. 2015-84943" disclosed by the present applicant, a detailed description thereof will be omitted. In addition, the determination unit 43 may determine the gait by using another technology.

FIG. 12A illustrates a diagram illustrating an example of a distribution ratio of the left and right balance. In the example of FIG. 12A, the distribution ratio of the left and right balance in a plurality of times of walking completions of a normal horse in which the lameness does not occur is illustrated by a pie chart. The left and right balance changes due to the change of the road surface or the motion of the horse during the walking. Therefore, the left and right balance changes for each walking completion, but for normal horses, in a case of looking at the plurality of times of walking completions, the left and right balance becomes mostly equivalent. FIG. 12B illustrates a diagram illustrating an example of the distribution ratio of the left and right balance. In the example of FIG. 12B, the distribution ratio of the left and right balance in the plurality of times of walking completions of the horse in which the lameness occurs is illustrated by a pie chart. Two examples are illustrated in FIG. 12B. In a case where an abnormality is generated in a limb, the horse walks while hiding the limb such that the weight is not applied to the limb having an abnormality. Therefore, in a case of looking at the plurality of times of walking completions, the left and right balance collapses, and the ratio of determination that there is a balance on the side of the limb which is not hidden (limb in which an abnormality is not generated) increases. In the example of FIG. 12B, since there is a large ratio of determination that there is the balance on the left side, it is presumed that an abnormality is generated in the right limb when the horse is viewed from the front.

FIG. 13 illustrates a diagram illustrating an example of a transition of evaluation results of the left and right balance for each walking completion for the plurality of times of walking completions. In the example of FIG. 13, the evaluation results of the left and right balance are illustrated in order of measurement times for each walking completion with respect to 395 walking completions when training of 5-minute rapid walk (trot) is performed. In the example of FIG. 13, a pattern is changed in accordance with the evaluation result for each walking completion. In the example of FIG. 13, at the beginning of the training, the evaluation in which the balance is on the left side and the evaluation in which the balance is on the right side exist together, and no abnormality is seen. However, in the example of FIG. 13, after time T1, the evaluation in which the balance is on the left side frequently occurs. From the result, it is presumed that the lameness occurs due to the abnormality generated in the right limb when the horse is viewed from the front after time T1.

The candidate identifying unit 44 identifies a candidate for a limb having a problem based on the result of evaluating the left and right balance during the movement by the evaluation unit 42. For example, the candidate identifying unit 44 determines whether or not there is a tilt in the left and right balance as a result of evaluating the left and right balance during the movement by the evaluation unit 42. For example, the candidate identifying unit 44 determines that there is a tilt in the left and right balance in a case where the ratio of the result of evaluating the left and right balance has a difference of a predetermined value or more. For example, in the candidate identifying unit 44, in a case where the ratio of evaluation that there is a balance on one of the right and left side is larger than the ratio of evaluation that there is a balance on the other one of the right and left side by a predetermined value (for example, 20%) or more, it is determined that there is a tilt on one side. In the example of FIG. 12B, it is determined that there is a tilt on the left side since the ratio of evaluation that there is a balance on the left side is larger than the ratio of evaluation that there is a balance on the right side by 20% or more. In addition, the candidate identifying unit 44 may evaluate the left and right balance from all of the distribution ratios of the left and right balance as illustrated in FIG. 12A. In addition, the candidate identifying unit 44 may evaluate the evaluation result of the left and right balance for each one walking completion arranged in the order of the measurement times illustrated in FIG. 13 from the distribution ratio of the left and right balance from the beginning for each predetermined step (for example, 20 steps).

In a case where the candidate identifying unit 44 determines that there is a tilt in the left and right balance, the candidate identifying unit 44 identifies the candidate for a limb having a problem in which the lameness occurs. In a case where there is a tilt on the right side, the candidate identifying unit 44 identifies the left forelimb and the right hindlimb as candidates for a limb having a problem, and in a case where there is a tilt on the left side, the candidate identifying unit 44 identifies the right forelimb and the left hindlimb as candidates for a limb having a problem.

Here, the lameness is found in walk and trot, and in particular, the lameness is likely to be found in trot. This is because, in a case where the horse is running in canter or gallop, the horse concentrates on running and the lameness is unlikely to occur even when some abnormalities are generated in the four limbs. Therefore, the candidate identifying unit 44 identifies the candidate for a limb having a problem from the result of evaluating the left and right balance when the horse moves in the gait of walk or trot.

The problem limb identifying unit 45 identifies a limb having a problem among the limbs which are considered as the candidates for a limb having a problem identified by the candidate identifying unit 44.

Here, there is a case where a horse performs a nutation movement in a case where there are some abnormalities in four limbs and the lameness occurs. The nutation movement is a movement in which a horse moves the head up and down when the pain is felt in a limb. In a case of lameness of forelimbs, the horse performs the nutation movement that shakes the head upward. In a case of lameness of hindlimbs, the horse performs the nutation movement that shakes the head upward.

Here, in a case where the upward nutation movement is detected when moving the forelimb and the hindlimb which are considered as the candidates for a limb having a problem from the measurement data 35, the problem limb identifying unit 45 identifies the forelimb considered as the candidate for a limb having a problem as a limb having a problem. In addition, in a case where the downward nutation movement is detected when moving the forelimb and the hindlimb which are considered as the candidates for a limb having a problem, the problem limb identifying unit 45 identifies the hindlimb considered as a candidate for a limb having a problem as a limb having a problem. The problem limb identifying unit 45 determines whether or not acceleration equal to or greater than a predetermined value which is considered as a nutation movement in the upward direction or in the downward direction is generated, in the measurement data 35 during the movement of the forelimb and the hindlimb which are considered as the candidates for a limb having a problem. The problem limb identifying unit 45 determines that the upward nutation movement has occurred in a case where the acceleration equal to or greater than a predetermined value is generated in the upward direction, and determines that the downward nutation movement has occurred in a case where the acceleration equal to or greater than a predetermined value is generated in the downward direction. In addition, the problem limb identifying unit 45 may detect the nutation movement from the upward or downward moving velocity. For example, the problem limb identifying unit 45 may determine that the upward nutation movement has occurred in a case where the moving velocity equal to or greater than a predetermined value which is considered as the nutation movement is generated in the upward direction, and may determine that the downward nutation movement has occurred in a case where the moving velocity equal to or greater than a predetermined value which is considered as the nutation movement is generated in the downward direction.

The problem limb identifying unit 45 identifies the forelimb which is considered as the candidate for a limb having a problem as a limb having a problem in a case where the upward nutation movement is detected, and identifies the hindlimb which is considered as the candidate for a limb having a problem as a limb having a problem in a case where the downward nutation movement is detected.

In addition, in a case where the horse has some abnormalities in the hindlimbs and the lameness occurs, there is a case where the left and right balance is reversed in the gait of trot and the gait of walk. Meanwhile, in a case where the horse has some abnormalities in the forelimbs and the lameness occurs, the left and right balance is not reversed in the gait of trot and the gait of walk.

Here, the problem limb identifying unit 45 evaluates whether the gait of trot and the gait of walk of the evaluation data 36 are deviated to either the left side or the right side respectively. For example, the problem limb identifying unit 45 determines that there is a tilt in the left and right balance in the gait of trot by the candidate identifying unit 44, and determines whether or not there is a difference of a predetermined value or more in the ratio of the result of evaluating the left and right balance of the gait of walk in a case where the nutation movement is not detected. The problem limb identifying unit 45 determines that there is a tilt in the left and right balance in a case where there is a difference of a predetermined value or more in the ratio of the result of evaluating the balance. The problem limb identifying unit 45 identifies the hindlimb considered as the candidate for a limb having a problem as a limb having a problem in a case where the left and right balance is reversed in the gait of trot and the gait of walk. In addition, the problem limb identifying unit 45 identifies the forelimb considered as the candidate for a limb having a problem as a limb having a problem in a case where the left and right balance is not reversed in the gait of trot and the gait of walk.

Incidentally, when the lameness occurs in the horse, an asymmetric motion waveform when the horse moves in the gait of walk and trot appears. Therefore, it is possible to obtain a limb having a problem from the motion waveform when the horse moves in the gait of walk and trot. For example, in the candidate identifying unit 44, in a case where there is no tilt in the left and right balance and it is not possible to identify the candidate for a limb having a problem by the candidate identifying unit 44, based on the measurement data 35, any of the motion waveforms in the up-down direction, in the left-right direction, in the yaw axis direction, and in the front-rear direction when the horse moves in a gait of trot are obtained. For example, the candidate identifying unit 44 obtains the acceleration in the up-down direction, the acceleration in the left-right direction, and the acceleration in the front-rear direction, from the accelerations in the three axial directions and the angular velocities of three axes which are stored in the measurement data 35. Further, the evaluation unit 42 obtains the acceleration in the yaw axis direction, from the accelerations in the three axial directions and the angular velocities of the three axes which are stored in the measurement data 35. The candidate identifying unit 44 obtains the motion waveforms indicating changes in acceleration in the up-down direction, acceleration in the left-right direction, acceleration in the yaw axis direction, and acceleration in the front-rear direction when the horse moves in the gait of trot. In addition, the candidate identifying unit 44 obtains the motion waveforms indicating changes in velocity in the up-down direction, velocity in the left-right direction, velocity in the yaw axis direction, and velocity in the front-rear direction, from the acceleration in the up-down direction, the acceleration in the left-right direction, the acceleration in the yaw axis direction, and the acceleration in the front-rear direction when the horse moves in the gait of trot.

Figure 14:
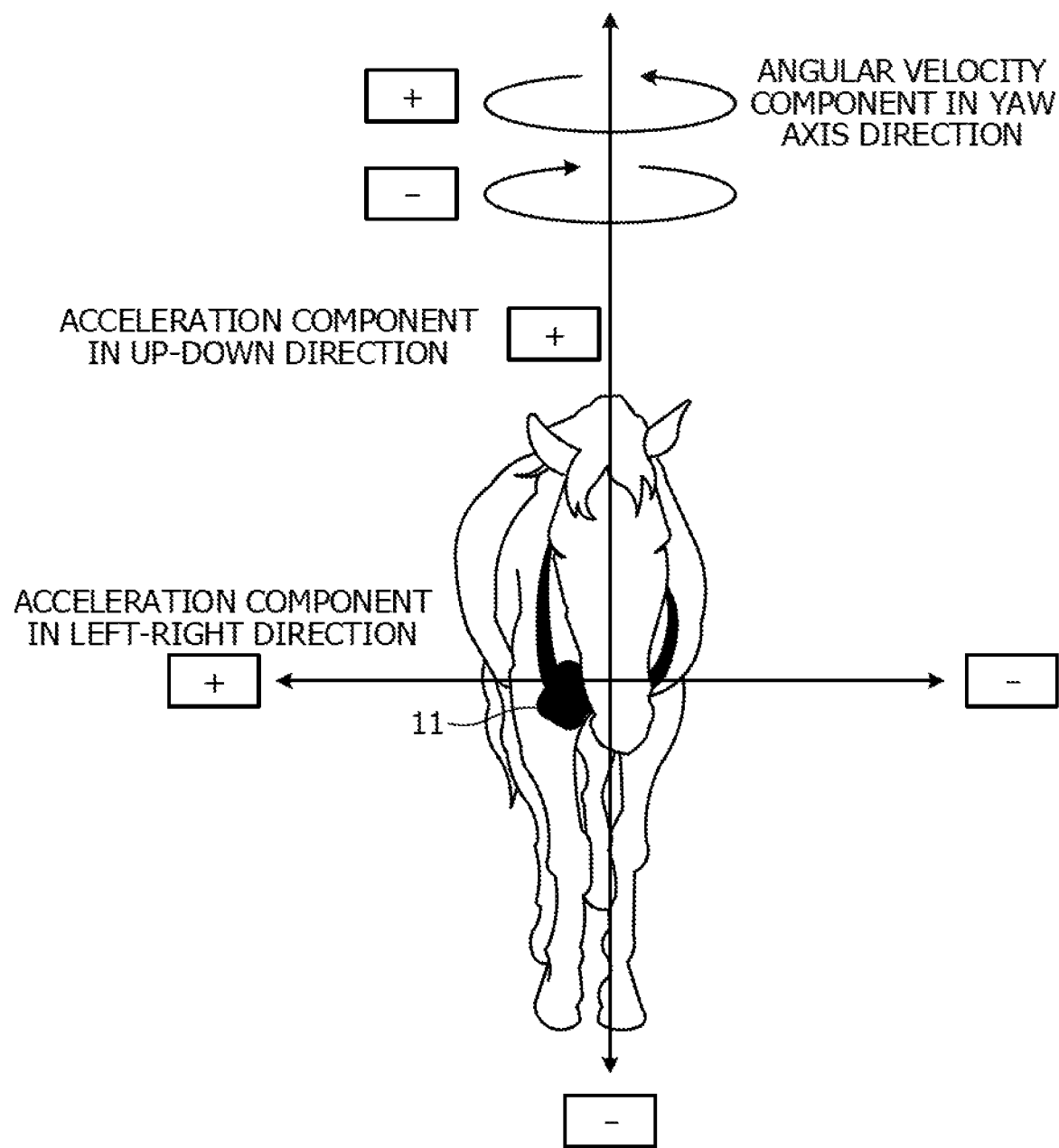
FIG. 14 illustrates a view illustrating a direction with respect to the horse.

FIG. 14 is a view illustrating a direction with respect to the horse. The measurement device 11 is attached in front of the chest of the horse. In the example, as illustrated in FIG. 14, the upward direction with respect to the horse is positive in the up-down direction, and the downward direction with respect to the horse is negative in the up-down direction. Further, in the example, the rightward direction with respect to the traveling direction of the horse is positive in the left-right direction and the leftward direction with respect to the traveling direction of the horse is negative in the left-right direction. In addition, in the example, the rightward turning direction with respect to the upward axis of the up-down direction of the horse is positive in the yaw axis direction and the leftward turning direction with respect to the upward axis in the up-down direction of the horse is negative as the yaw axis direction.

FIG. 15 illustrates a diagram schematically illustrating a positional relationship of four limbs when the horse moves. FIG. 15 illustrates the positional relationship of four limbs of the horse of (1) walk and (2) trot. FIG. 15 schematically illustrates the positional relationship of four limbs of the horse of each gait on the left side of the drawing, and illustrates the presence or absence of grounding of each limb (right forelimb, left forelimb, right hindlimb, and left hindlimb) in periods indicated by "1" to "8" of each gait on the right side of each schematic diagram. In addition, in FIG. 15, although the four limbs are also seen to be in contact with the ground in the period indicated by "1" or "4" in trot, when confirming the actual data in detail, switching of limbs is quickly performed in the periods, and the time when the body of the horse is floating exists.

At the time of the trot, as illustrated in (2) of FIG. 15, the horse trots and moves the right forelimb and the left hindlimb, and the left forelimb and the right hindlimb in pair.

Figure 16:
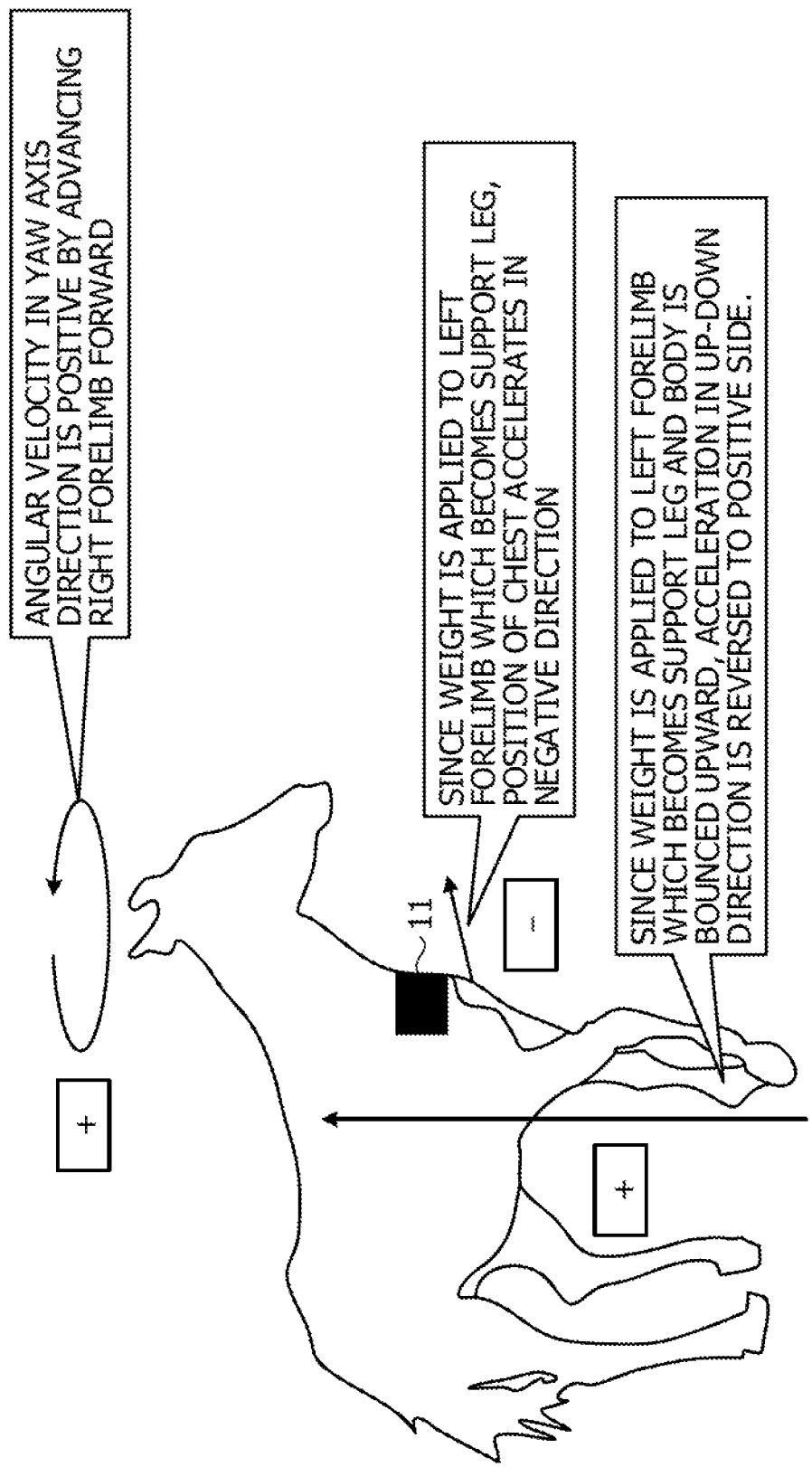
FIG. 16 illustrates a view illustrating the movement of the horse when moving in trot.

FIG. 16 is a view illustrating the movement of the horse when moving in trot. As illustrated in FIG. 16, in a case where the measurement device 11 is attached in front of the chest of the horse, the sign of the angular velocity of the yaw axis is reversed at the timing when the forelimb swing leg of the horse is advanced forward. In addition, since the weight is applied to the left forelimb which is a support leg, the position of the chest is accelerated in the negative direction of the left-right direction. In addition, since the weight is put on the forelimb support leg and the body is bounced upward, the acceleration in the up-down direction becomes a waveform of a positive sign. Further, at a landing timing of the forelimb support leg, the sign of the acceleration in the up-down direction of the horse is reversed to the positive.

Figure 17:
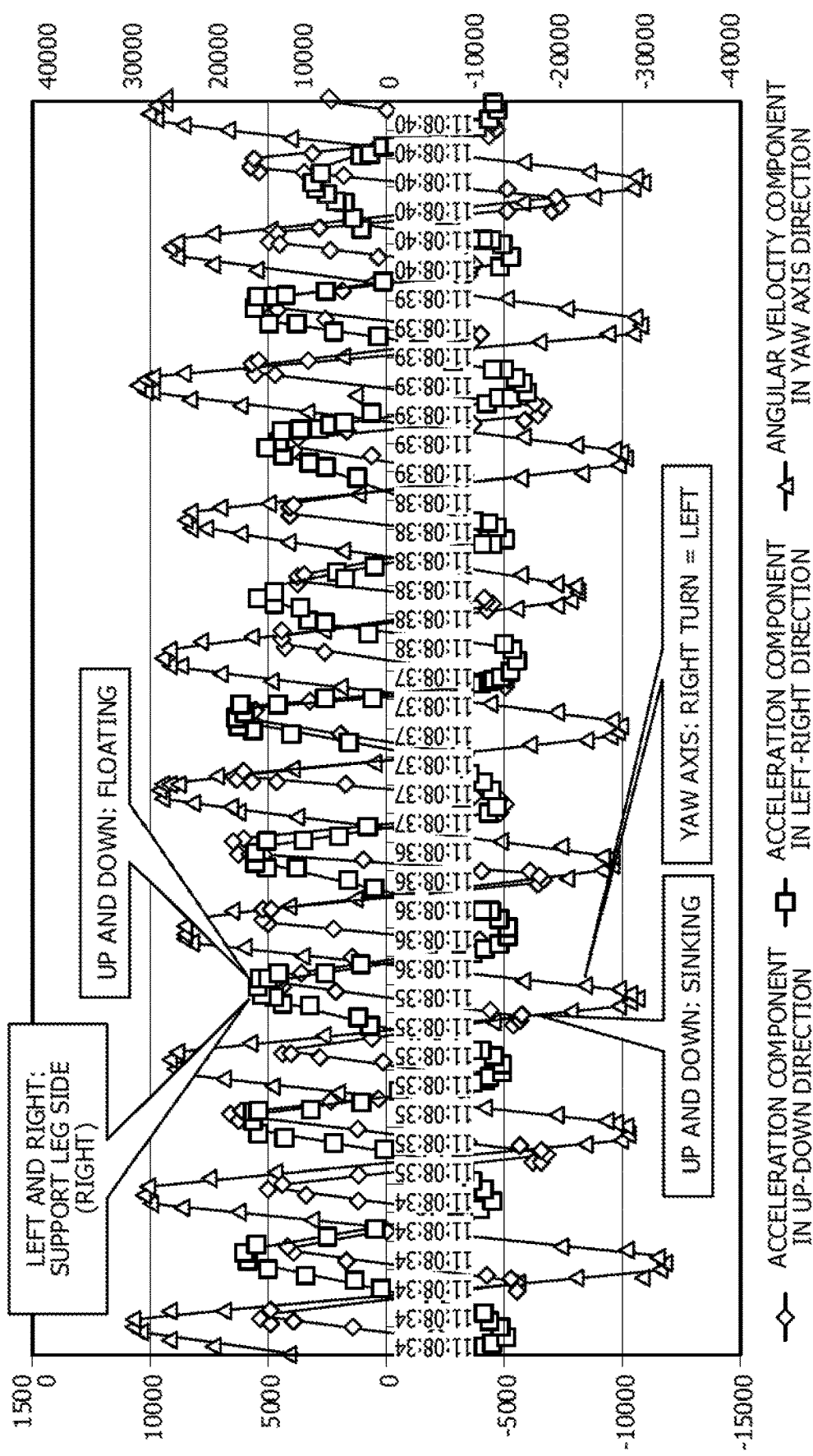
FIG. 17 illustrates a diagram illustrating an example of a motion waveform indicating a change in acceleration in an up-down direction, acceleration in a left-right direction, and acceleration in a yaw axis direction when moving in trot.

FIG. 17 illustrates a diagram illustrating an example of a motion waveform indicating a change in acceleration in the up-down direction, acceleration in the left-right direction, and acceleration in the yaw axis direction when moving in trot. In a case of the trot, the horse applies the weight to the support leg (the body sinks first) at the same time when advancing the swing leg forward, and then the body is bounced upward. At this time, the body of the horse is tilted toward the support leg side. Therefore, the acceleration in the up-down direction, the acceleration in the left-right direction, and the acceleration in the yaw axis direction draw the motion waveform illustrated in FIG. 17.

When the lameness occurs, the horse hides the limb in which the lameness occurs, and thus, the left and right balance tends to collapse. For example, when the swing leg hurts, the horse reduces the velocity of advancing the limb. Therefore, the wavelength of the acceleration or the velocity becomes small. In addition, the horse tries to make the swing leg land quickly when the support leg hurts. Therefore, the amplitude of the acceleration or the velocity becomes small. Accordingly, for example, the motion waveform of the angular velocity of the yaw axis or the acceleration becomes asymmetric. In addition, the horse tries not to apply the weight to the leg when the support leg hurts. Therefore, the motion waveform of the velocity or the acceleration in the up-down direction, the motion waveform of the velocity or the acceleration in the left-right direction, the velocity or the acceleration in the yaw axis direction become asymmetric in a case where the side which does not hurt is the support leg and in a case where the side which huts is the support leg.

Therefore, it is possible to obtain a limb having a problem from the motion waveform when the horse moves. For example, as described above, at the time of the trot, the horse trots and moves the right forelimb and the left hindlimb, and the left forelimb and the right hindlimb in pair. Therefore, for example, when the lameness occurs in the horse, lateral asymmetry appears regularly in the motion waveform at the time of the trot. In a case where asymmetry appears regularly in the motion waveform, the candidates for a limb having a problem are narrowed down to the right forelimb and the left hindlimb, or the left forelimb and the right hindlimb.

Here, as a result of evaluating the left and right balance at the time of the movement by the evaluation unit 42, the candidate identifying unit 44 determines the presence of absence of the lameness from the symmetry of the motion waveform in any of the up-down direction, the left-right direction, and the yaw axis direction when the horse moves in the gait of trot in a case where there is no tilt in the left and right balance. For example, the symmetry of the motion waveform may be evaluated by the amplitude (peak value) of the waveform, may be evaluated by the wavelength of the waveform, or may be evaluated by the area of the waveform.

Figure 18A:
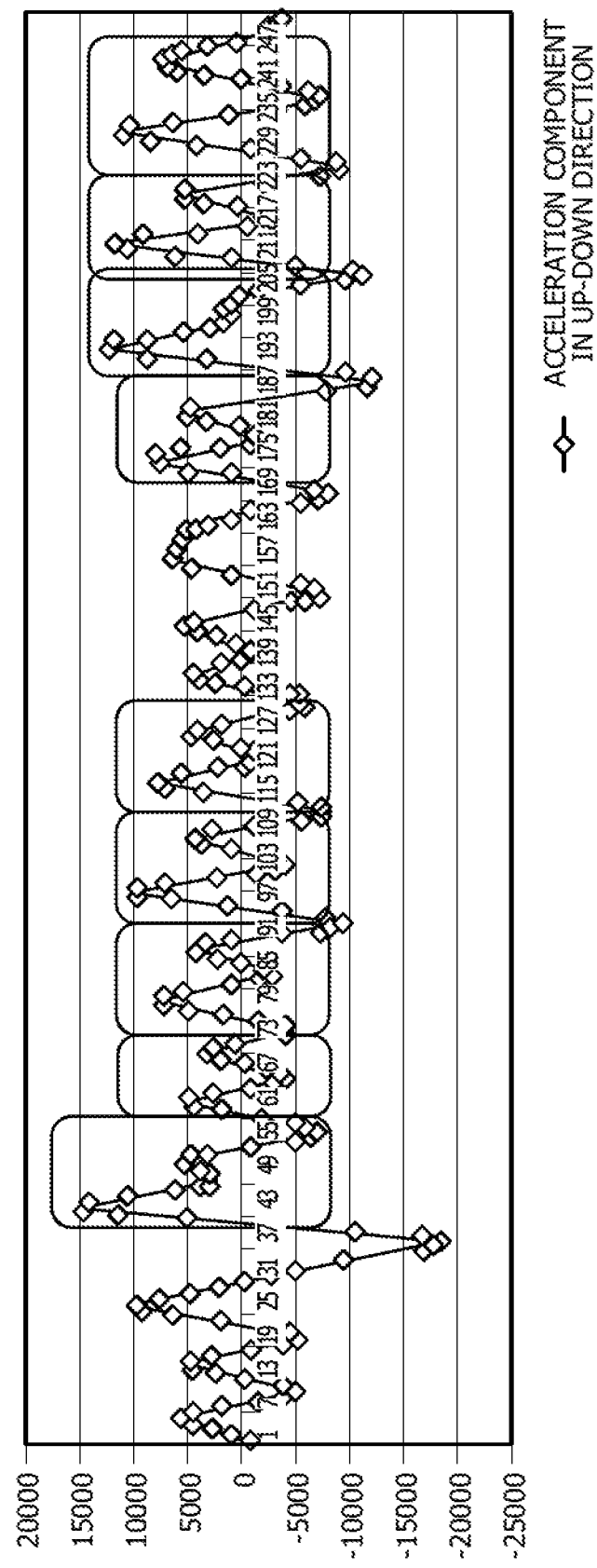
FIG. 18A illustrates a diagram illustrating an example of a motion waveform of acceleration in the up-down direction when lameness occurs.

FIG. 18A illustrates a diagram illustrating an example of the motion waveform of the acceleration in the up-down direction when the lameness occurs. When the lameness occurs, the horse hides the limb in which the lameness occurs, and thus, the motion waveform when moving the limb in which the lameness occurs becomes small. Therefore, as illustrated in FIG. 18A, the rhythm of high mountain and low mountain appears repeatedly in the motion waveform of the acceleration in the up-down direction. FIG. 18B illustrates a diagram illustrating an example of the motion waveform of the acceleration in the up-down direction and the motion waveform of the angular velocity in the yaw axis direction in a case where the lameness occurs. FIG. 18B illustrates a diagram in which the motion waveform of the acceleration in the up-down direction illustrated in FIG. 18A and the motion waveform of angular velocity in the yaw axis direction overlap each other. In a case where the horse advances the right forelimb forward, the angular velocity in the yaw axis direction turns toward the positive side, and in a case where the horse advances the left forelimb forward, the angular velocity in the yaw axis direction turns toward the negative side. From this, it is possible to determine which of the right forelimb and the left forelimb is advanced when a small motion waveform is generated in the up-down direction by the angular velocity in the yaw axis direction. In a case of a right turn (turning toward the positive side in the yaw axis direction in FIG. 18B) in the yaw axis direction when the motion waveform smaller than a predetermined ratio (for example, 80%) in the up-down direction is generated, the candidate identifying unit 44 identifies the left forelimb and the right hindlimb as the candidates for a limb having a problem. In addition, in a case of the left turn (turning toward the positive side in the yaw axis direction in FIG. 18B) in the yaw axis direction when the motion waveform smaller than a predetermined ratio in the up-down direction is generated, the candidate identifying unit 44 identifies the right forelimb and the left hindlimb as the candidates for a limb having a problem. In addition, the candidates for a limb having a problem may be identified from the evaluation in the plurality of steps. For example, the candidate identifying unit 44 may identify the candidate for a limb having a problem in a case where the same limb is considered as a candidate at a predetermined ratio (for example, 80%) or more in the plurality of steps.

In a case where the candidate for a limb having a problem is identified in the gait of trot, the problem limb identifying unit 45 reads out the data at the time of the gait of walk from the measurement data 35 and obtains the motion waveform when the horse moves in the gait of walk. For example, the problem limb identifying unit 45 obtains the motion waveform in any of the up-down direction, the left-right direction, and the yaw axis direction when the horse moves in the gait of walk. In addition, the problem limb identifying unit 45 identifies the limb having a problem from the symmetry of the motion waveform in the gait of walk. For example, the problem limb identifying unit 45 obtains the motion waveform in any of the up-down direction, the left-right direction, and the yaw axis direction when the horse moves in the gait of walk. The problem limb identifying unit 45 determines whether or not an asymmetric motion waveform appears in the obtained motion waveform. For example, the symmetry of the motion waveform may be evaluated by the amplitude of the waveform, may be evaluated by the wavelength of the waveform, or may be evaluated by the area of the waveform. In a case where the asymmetric motion waveform appears, the problem limb identifying unit 45 determines whether or not an asymmetric disorder is interlocked with any limb identified as the candidate for a limb having a problem. The problem limb identifying unit 45 identifies an interlocking limb as a limb having a problem in a case where the disorder is interlocked with any limb identified as the candidate for a limb having a problem.

FIG. 19A illustrates a diagram illustrating an example of the motion waveforms in a case where the lameness occurs. FIG. 19A illustrates ground-off and landing timings of the right forelimb and the left forelimb. A method for obtaining the ground-off and landing timings of each of the limbs of the horse in the walk will be described later. In the example of FIG. 19A, the acceleration in the left-right direction becomes asymmetric, the motion waveform on the left side (the negative side in FIG. 19A) is larger than that on the right side (positive side in FIG. 19A), and the body of the horse is tilted to the left side during the ground-off of the right forelimb. In this case, the horse feels pain at the ground-off timing of the right forelimb or the landing timing of the right hindlimb.

The problem limb identifying unit 45 first determines that the horse feels pain at the landing timing of the right forelimb or at the ground-off timing of the right hindlimb in a case where a large motion waveform is generated on the left side in the motion waveform of the acceleration in the left-right direction. In addition, the problem limb identifying unit 45 first determines that the horse feels pain at the ground-off timing of the left forelimb or at the landing timing of the left hindlimb in a case where a large motion waveform is generated on the right side in the motion waveform of the acceleration in the left-right direction. In the example of FIG. 19A, the left forelimb and the right hindlimb are first determined as the candidates for a limb having a problem.

In the example of FIG. 19A, the problem limb identifying unit 45 determines that the sinking (acceleration in the negative direction) after the landing of the right hindlimb has a smaller amplitude and a shorter waveform compared to the immediately previous floating (acceleration in the positive direction) or the sinking one step before, from the motion waveform of the acceleration in the up-down direction. Accordingly, it is determined that there was a pain at the time of landing and there was a movement to avoid the load.

FIG. 19B illustrates a diagram illustrating another example of the motion waveforms in a case where the lameness occurs. FIG. 19B illustrates the ground-off and landing timings of the right forelimb and the left forelimb. In the example of FIG. 19B, the period from the ground-off to the landing of the right forelimb (hereinafter, described as throwing) is different from the time during the throwing of the left forelimb. In addition, the peak of the angular velocity of the yaw axis during the throwing of the right forelimb is smaller than the peak during the throwing of the left forelimb. From this, the example in FIG. 19B is "a state where the right limb is difficult to be advanced forward". In the "state where the right limb is difficult to be advanced forward", a case where there is a problem in the right forelimb itself which is being thrown and a case where there is a problem in other limbs to which the load is applied by raising the right forelimb, are considered, but the asymmetry is not seen in the acceleration component in the up-down direction and the acceleration component in the left-right direction. From this, the example in FIG. 19B is determined as a right forelimb lameness (there is a pain at the time of ground-off).

The problem limb identifying unit 45 determines "a state where the right limb is difficult to be advanced forward" in a case where the peak of the angular velocity of the yaw axis during the right forelimb throwing is smaller than the peak during the left forelimb throwing. In addition, the problem limb identifying unit 45 identifies the right forelimb as a limb having a problem in a case where the asymmetry is not seen in the acceleration component in the up-down direction and the acceleration component in the left-right direction. In addition, the problem limb identifying unit 45 determines "a state where the left limb is difficult to be advanced forward" in a case where the peak of the angular velocity of the yaw axis during the left forelimb throwing is smaller than the peak during the right forelimb throwing. In addition, the problem limb identifying unit 45 identifies the left forelimb as a limb having a problem in a case where the asymmetry is not seen in the acceleration component in the up-down direction and the acceleration component in the left-right direction.

In addition, it is possible to obtain a limb having a problem from the motion waveform when the horse moves in the gait of walk. The horse moves each limb separately as illustrated in (1) of FIG. 15 at the time of the walk.

FIG. 20 is a view illustrating the movement of the horse when moving in walk. As illustrated in FIG. 20, in a case where the measurement device 11 is attached in front of the chest of the horse, the sign of the angular velocity of the yaw axis is reversed at the timing when the forelimb of the horse is advanced forward. For example, the angular velocity of the yaw axis is reversed to the negative side at the timing when the left forelimb is advanced forward. In addition, at the timing of landing of the forelimbs, since the weight is put on the landing limb and the body stretches upward, the acceleration in the up-down direction is reversed to the positive side. In addition, at the timing when the left forelimb is advanced forward, the position of the chest is accelerated in the positive direction of the left-right direction.

Figure 21:
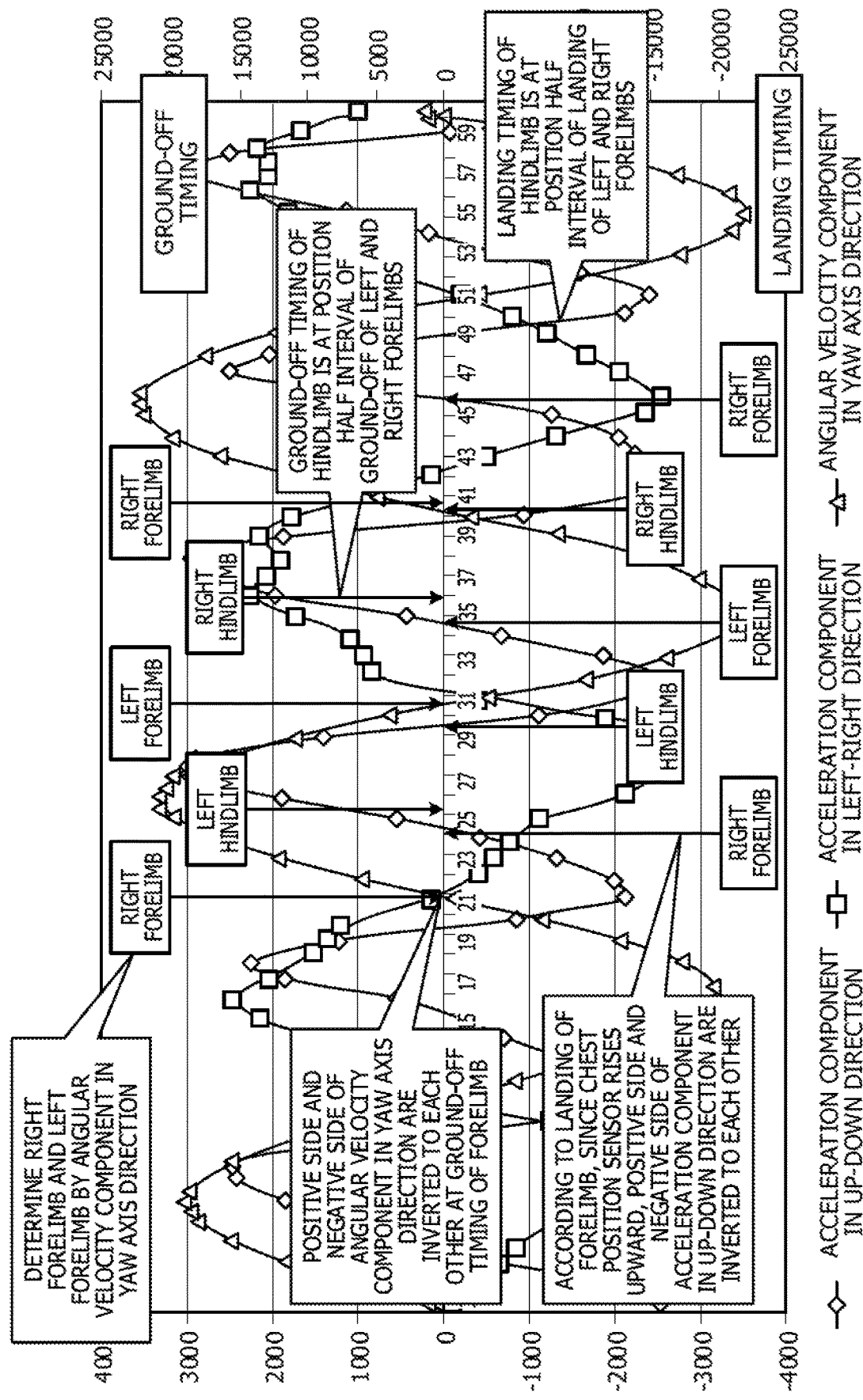
FIG. 21 illustrates a diagram illustrating an example of motion waveforms indicating a change in acceleration in the up-down direction, acceleration in the left-right direction, and acceleration in the yaw axis direction when moving in walk.

FIG. 21 illustrates a diagram illustrating an example of the motion waveforms indicating a change in acceleration in the up-down direction, acceleration in the left-right direction, and acceleration in the yaw axis direction when moving in trot. In the horse, the sign of the angular velocity of the yaw axis is reversed at the timing when the forelimb advances forward, the right forelimb advances forward in a case where the acceleration in the yaw axis direction increases in the left turn direction, and the left forelimb advances forward in a case where the acceleration in the yaw axis direction increases in the right turn direction. In addition, since the horse puts the weight on the landing limb and moves the body stretching upward at the landing timing of the forelimb, the acceleration in the up-down direction is reversed from the negative side to the positive side and the acceleration in the up-down direction becomes a waveform having a positive sign. Further, in the horse, the yaw axis direction turns leftward at the landing timing of the right forelimb, and the yaw axis direction turns rightward at the landing timing of the left forelimb. In addition, the horse has the ground-off timing of the left and right hindlimbs at a position half the ground-off timing of the left and right forelimbs. Further, the horse has the landing timing of the left and right hindlimbs at a position half the landing timing of the left and right forelimbs.

The distinguishing unit 46 distinguishes the ground-off and landing timings of each of the four limbs of the horse from the motion waveform when the horse moves in the gait of walk. For example, the distinguishing unit 46 distinguishes the ground-off and landing timings of each of the four limbs of the horse from the motion waveforms in the up-down direction and in the yaw axis direction when the horse moves in the gait of walk. For example, the distinguishing unit 46 distinguishes the point of time at which the positive side and negative side of the acceleration in the yaw axis direction are reversed, as the ground-off timing of the right forelimb when the acceleration in the yaw axis direction increases in the left turn direction from the point of time and the ground-off timing of the left forelimb when the acceleration in the yaw axis direction increases in the right turn direction from the point of time. In addition, for example, the distinguishing unit 46 distinguishes the point of time at which the acceleration in the up-down direction is reversed from the negative side to the positive side, as the landing timing of the right forelimb when the yaw axis direction is the left turn direction at the point of time and the landing timing of the left forelimb when the yaw axis direction is the right turn direction at the point of time. Further, for example, the distinguishing unit 46 distinguishes an intermediate timing between the ground-off timing of the right forelimb and the ground-off timing of the left forelimb as the ground-off timing of the left hindlimb. The distinguishing unit 46 distinguishes an intermediate timing between the ground-off timing of the left forelimb and the ground-off timing of the right forelimb as the ground-off timing of the right hindlimb. The distinguishing unit 46 distinguishes an intermediate timing between the landing timing of the right forelimb and the landing timing of the left forelimb as the landing timing of the left hindlimb. The distinguishing unit 46 distinguishes an intermediate timing between the landing timing of the left forelimb and the landing timing of the right forelimb as the landing timing of the right hindlimb. In FIG. 21, the ground-off timings of each of the limbs (right forelimb, left forelimb, right hindlimb, and left hindlimb) are illustrated on the upper side, and the landing timings of each of the limbs are illustrated on the lower side.

The problem limb identifying unit 45 identifies the limb interlocked with the disorder of the motion waveform based on the ground-off and landing timings of each of the four limbs of the horse distinguished by the distinguishing unit 46. For example, the problem limb identifying unit 45 identifies a limb having an abnormality based on the motion waveforms in at least one of the left-right direction, the front-rear direction, the up-down direction, and the yaw axis direction.

Figure 22:
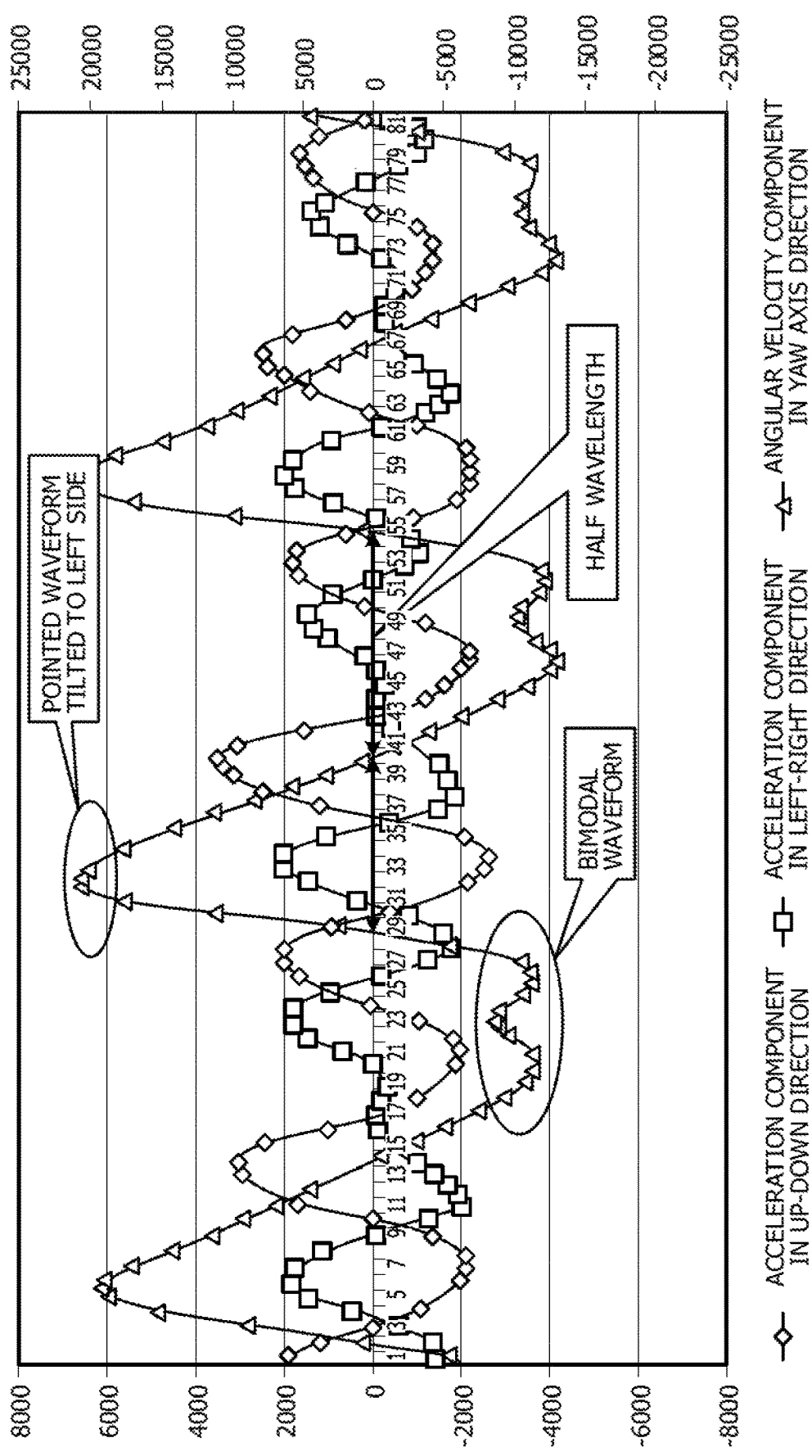
FIG. 22 illustrates a diagram illustrating an example of motion waveforms in a case where lameness occurs.

FIG. 22 illustrates a diagram illustrating an example of the motion waveforms in a case where the lameness occurs. In the example of FIG. 22, when the angular velocity in the yaw axis direction takes a negative value, that is, in a case where the left forelimb is a swing leg, the rotation speed slows down, and a bimodal waveform is generated. The timing of the generation of the bimodal waveform is the intermediate point between the time at which the left forelimb becomes a swing leg and the time at which the right forelimb becomes the swing leg, that is, the timing to move the right hindlimb.

Further, in the example of FIG. 22, the peak waveform in which the angular velocity in the yaw axis direction takes a positive value is a pointed waveform tilted to the left side. This indicates a behavior in which the horse desires to take off the right forelimb quickly and to avoid the pain of right hindlimb since the painful right hindlimb supports the right side. In addition, when paying attention to the half wavelength of the motion waveform of one cycle, the period of the waveform taking a positive value is shorter than the period of the waveform taking a negative value. This also indicates a behavior in which the horse slowly performs a motion of the painful right hindlimb and to avoid the pain of the right hindlimb.

In a case where the bimodal waveform is generated, the problem limb identifying unit 45 identifies the limb that corresponds to the timing of generation of the bimodal waveform as a limb having an abnormality. In the example of FIG. 22, for example, the problem limb identifying unit 45 identifies the right hindlimb as a limb having an abnormality since the bimodal waveform is generated at the intermediate point between the time at which the left forelimb becomes the swing leg and the time at which the right forelimb becomes the swing leg, that is, the timing of moving the right hindlimb.

In addition, in a case where the pointed peak waveform tilted to the left side is generated, the problem limb identifying unit 45 identifies the limb that corresponds to the timing of generation of the peak waveform as the limb having an abnormality. Further, in a case where there is a difference of a predetermined ratio (for example, 85%) or more between the period of a waveform taking a positive value of the motion waveform in one cycle and the period of the waveform taking the negative value, the problem limb identifying unit 45 identifies the limb that corresponds to the period of the waveform as a limb having an abnormality.

Figure 23:
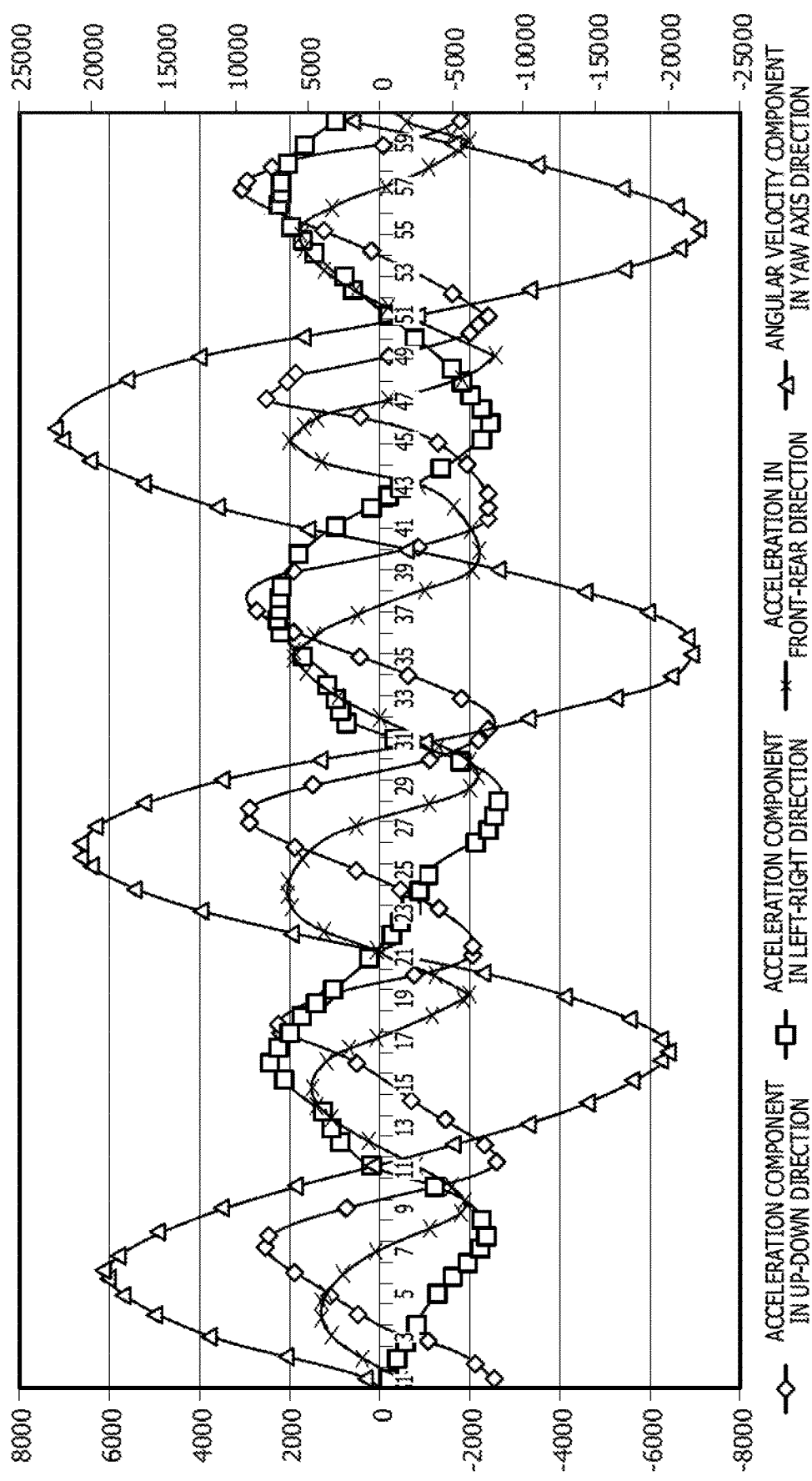
FIG. 23 illustrates a diagram illustrating an example of motion waveforms in a normal state where lameness does not occur.
Figure 24:
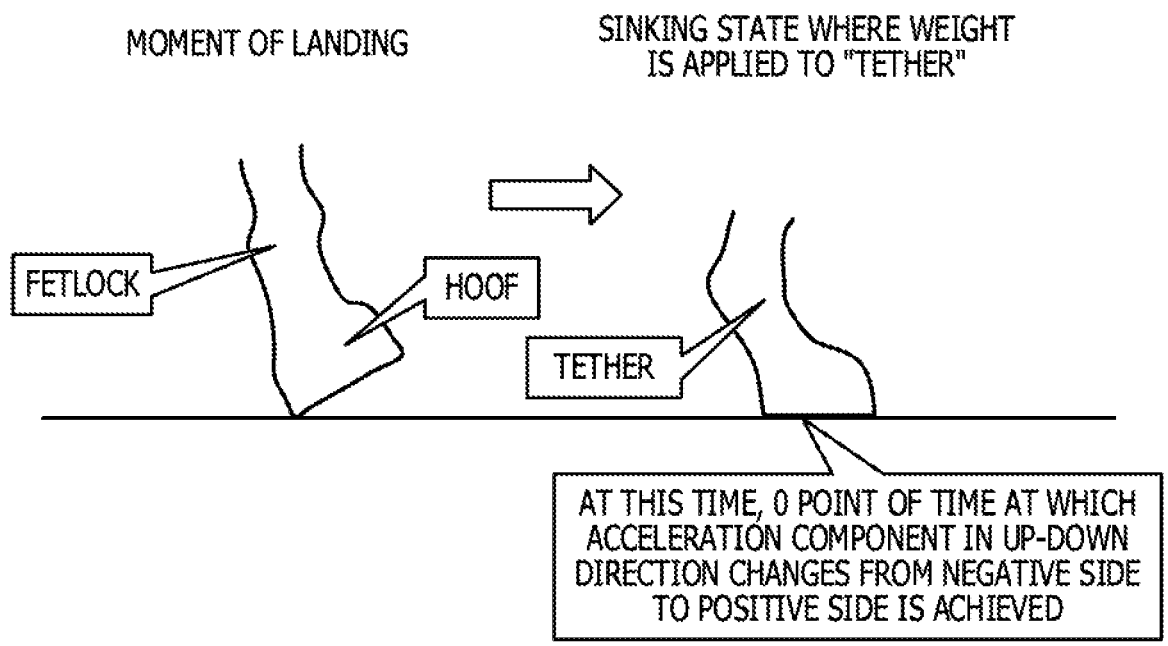
FIG. 24 illustrates a view illustrating a landing flow of the horse while walking.

FIG. 23 illustrates a diagram illustrating an example of the motion waveforms in a normal state where the lameness does not occur. In a case where the lameness does not occur, the acceleration in the front-rear direction has a waveform with the same frequency as the acceleration in the up-down direction. This indicates that the horse goes forward by stretching the body upward and forward starting from the landing of the forelimb. The waveform of the acceleration in the front-rear direction has a phase difference with the waveform of the acceleration in the up-down direction. This is because the point at which the acceleration in the up-down direction changes from the positive side to the negative side, which is the landing timing, exactly indicates the point of sinking by applying the weight to the so-called "tether" of the support legs after the landing. Meanwhile, the acceleration in the front-rear direction is for starting the acceleration in the forward direction interlocking with the movement of the swing limb. FIG. 24 is a view illustrating a landing flow of the horse while walking. As illustrated in FIG. 24, when the horse lands, the horse is in a state of sinking by applying the weight to the so-called "tether". The acceleration in the up-down direction becomes the 0 point of time at which the acceleration changes from the negative side to the positive side. In addition, depending on the timing of limb carrying, there is also a case where the acceleration in the up-down direction and the acceleration in the forward direction start at the same time. The motion waveform in FIG. 23 is an example.

Figure 25:
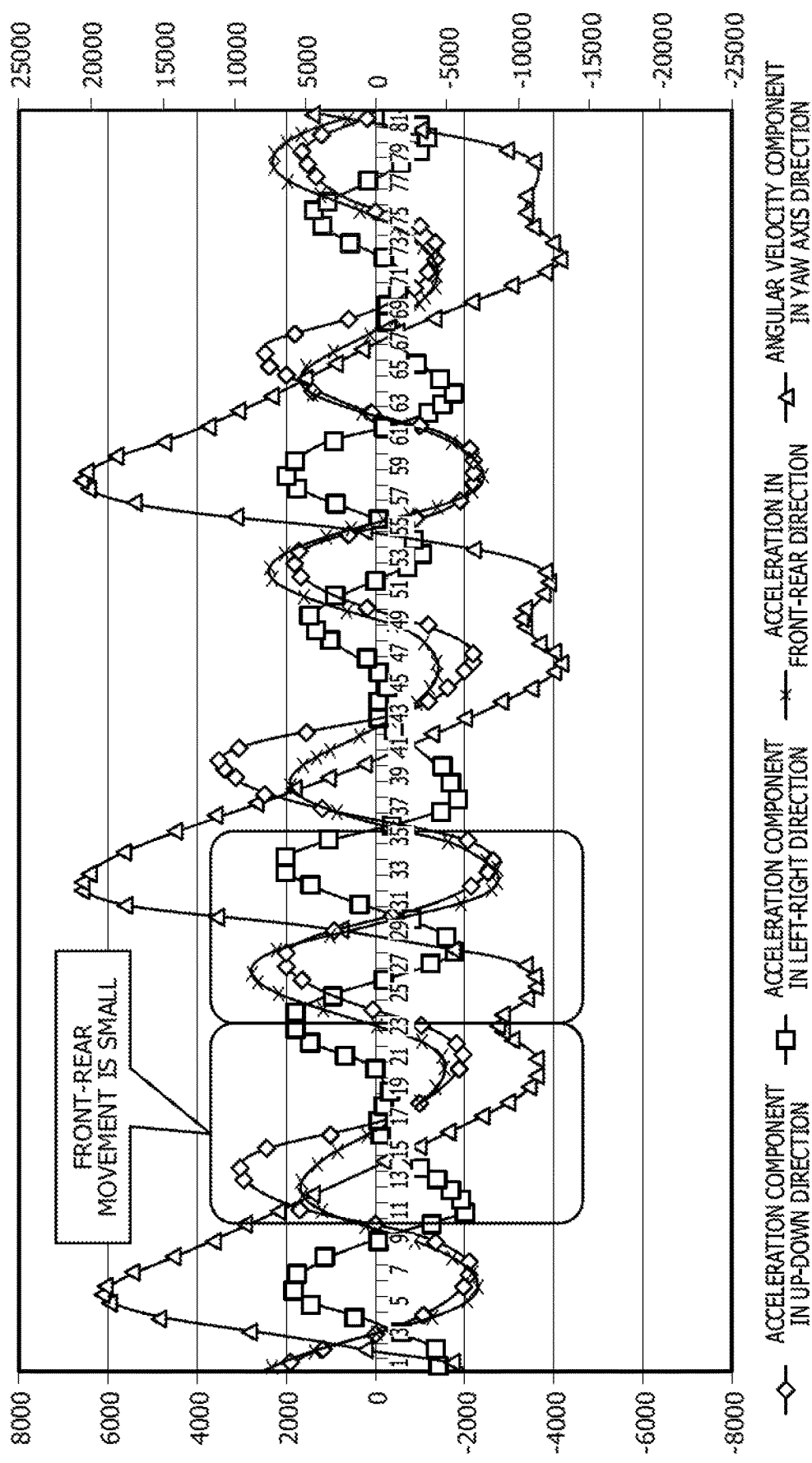
FIG. 25 illustrates a diagram illustrating an example of motion waveforms in a case where lameness occurs.

FIG. 25 illustrates a diagram illustrating an example of the motion waveforms in a case where the lameness occurs. In the example of FIG. 25, the waveform of the acceleration in the front-rear direction is synchronized with the waveform of the acceleration in the up-down direction. In addition, in the example of FIG. 25, when the angular velocity in the yaw axis direction in the landing of the forelimb takes a positive value, that is, in a case where the left forelimb is the support leg, the area of the waveform of the acceleration in the front-rear direction becomes small. This is the result of prioritizing the movement to make the swing leg of the right forelimb land quickly so as to hide the painful right hindlimb, and the waveform of the acceleration in the front-rear direction becomes asymmetric in the left and right periods.

The problem limb identifying unit 45 identifies the limb that corresponds to the period of the waveform of the small area as a limb having a problem in a case where the area of the waveform of the acceleration in the front-rear direction has a difference of a predetermined ratio (for example, 85%) or more.

In addition, the problem limb identifying unit 45 may also identify a limb having a problem from the deviation degree obtained by comparing an ideal waveform with an actual waveform. For example, the problem limb identifying unit 45 may identify a limb having a problem from the deviation degree obtained by comparing the ideal waveform with the actual waveform for the motion waveform in at least one of the left-right direction, the front-rear direction, the up-down direction, and the yaw axis direction.

Figure 26:
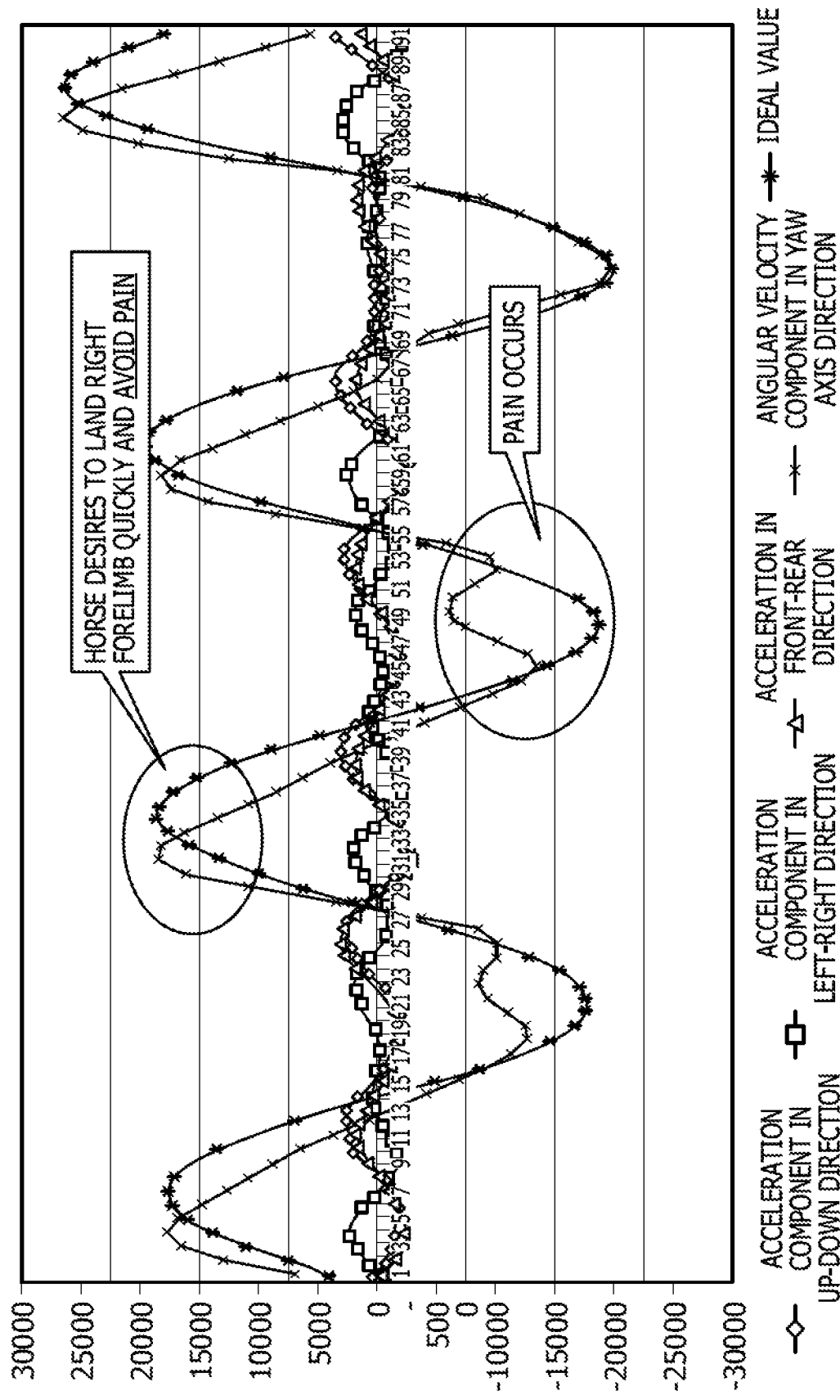
FIG. 26 illustrates a diagram illustrating an example of motion waveforms.

FIG. 26 illustrates a diagram illustrating an example of the motion waveforms. FIG. 26 illustrates an example of a result obtained by overlapping the ideal waveform and the actual waveform of the angular velocity in the yaw axis direction. The ideal waveform is, for example, as follows.

Wavelength=upper half wavelength of actual waveform to be compared+lower half wavelength of actual waveform Amplitude=values with large amplitude on upper side and lower side of actual waveform to be compared Frequency=1/wavelength Elapsed time=elapsed time considering start time of shorter waveform of half wavelength as start point Ideal value=amplitude×sin(2π×frequency×elapsed time)

Since the motion of the painful limb becomes slow, the half wavelength is long. By drawing the ideal waveform from the shorter waveform of the half wavelength that does not hurt, a deviation point from the ideal value can be detected.

The problem limb identifying unit 45 may obtain the ideal waveform and may identify the limb that corresponds to the ground-off and landing timings in the period in which the actual waveform deviates from the ideal waveform by a predetermined ratio (for example, 85%) or more as a limb having a problem. The problem limb identifying unit 45 compares the ideal value with the actual waveform and identifies the deviation point that is separated by a predetermined ratio. In addition, the problem limb identifying unit 45 may identify the point at which the ideal value and the peak value of the actual waveform are separated from each other by a predetermined ratio or more as the deviation point.

Figure 27:
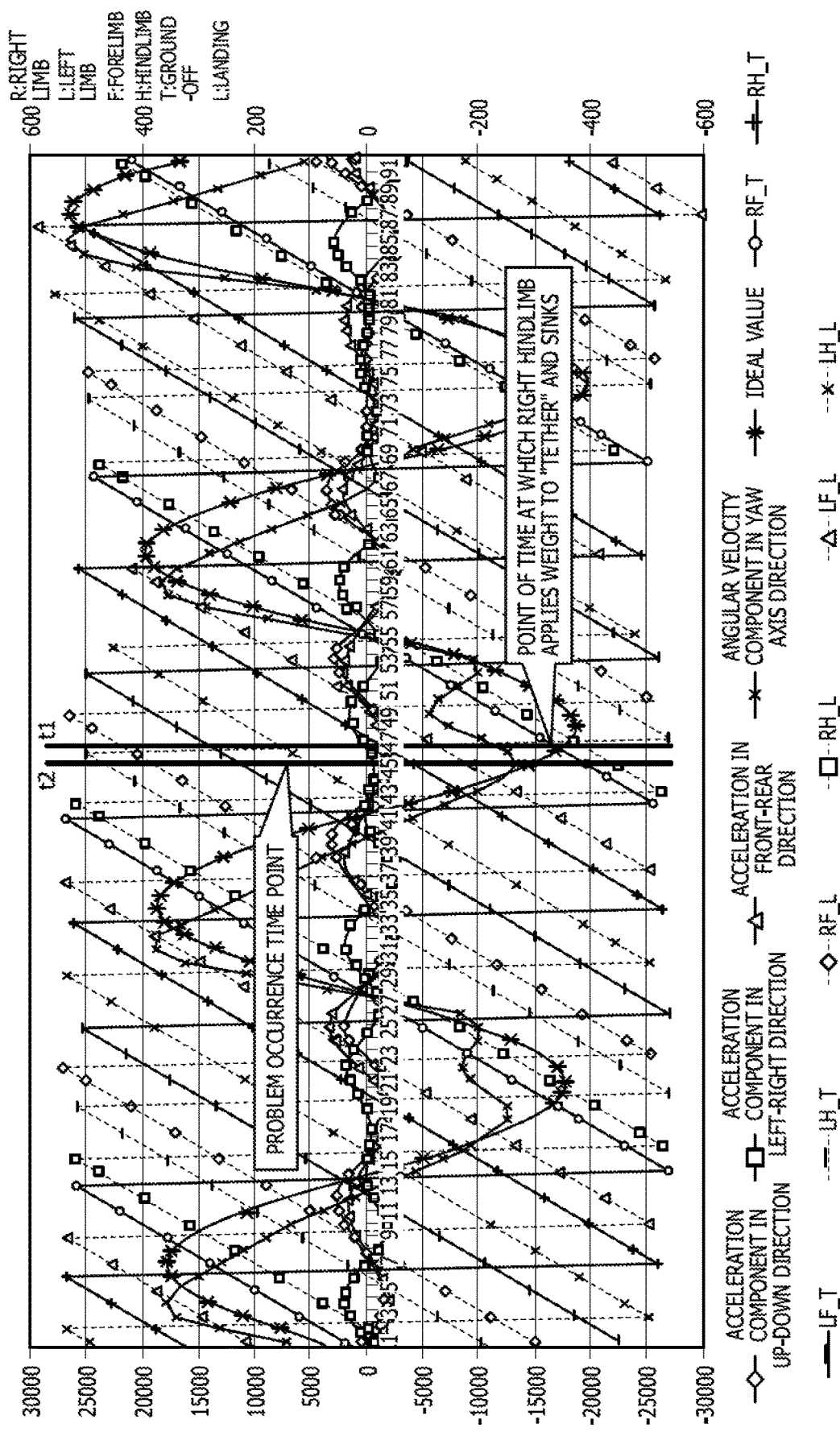
FIG. 27 illustrates a diagram for describing identification of a limb having a problem.

FIG. 27 illustrates a diagram for describing identification of a limb having a problem. In FIG. 27, the motion waveform of the acceleration in the front-rear direction, the motion waveform of the acceleration in the up-down direction, and the motion waveform of the angular velocity in the yaw axis direction are illustrated. In addition, in FIG. 27, an ideal motion waveform of the yaw axis is illustrated. In addition, in FIG. 27, corresponding to each of the four limbs, a time difference between the ground-off and landing points of time of each of the four limbs in a jaggy mountain-shaped waveform is illustrated. A waveform RF_T indicates the time difference from the ground-off timing of the right forelimb. A waveform RH_T indicates the time difference from the ground-off timing of the right hindlimb. A waveform LF_T indicates the time difference from the ground-off timing of the left forelimb. A waveform LH_T indicates the time difference from the ground-off timing of the left hindlimb. A waveform RF_L indicates the time difference from the landing timing of the right forelimb. A waveform RH_L indicates the time difference from the landing timing of the right hindlimb. A waveform LF_L indicates the time difference from the landing timing of the left forelimb. A waveform LH_L indicates the time difference from the landing timing of the left hindlimb. The waveforms RF_T, RH_T, LF_T, and LH_T are the timings at which each of the four limbs is taken off at the point of time when each of the waveforms becomes zero. The waveforms RF_L, RH_L, LF_L, and LH_L are the timings at which each of the four limbs lands at the point of time when each of the waveforms becomes zero. Here, at timing t1 of the landing of the right hindlimb, the deviation occurs between the actual motion waveform of the angular velocity in the yaw axis direction and the ideal motion waveform, and the problem occurs. Immediately before timing t1, timing t2 at which the deviation between the actual motion waveform of the angular velocity in the yaw axis direction and the ideal motion waveform disappears becomes a point of time at which the problem occurs. In the example of FIG. 27, a problem occurrence time point and a point that matches the ground-off and landing timings of the four limbs do not exist. In this case, the problem limb identifying unit 45 identifies the limb that corresponds to the problem occurrence time point as a limb having an abnormality. For example, the problem limb identifying unit 45 identifies which limb is moved and how the limb is moved when the pain occurs, from the time difference between the problem occurrence time point and the deviation time point of the four limbs. In the example of FIG. 27, in the direction in which the difference between the actual motion waveform of the angular velocity in the yaw axis direction and the ideal motion waveform increases, the most possible phenomenon is the ground-off of the right hindlimb. From this, it is presumed that the pain occurs immediately before the phenomenon, that is, at the point of time when the muscles of the limb is moved for lifting up the right hindlimb from the ground surface, and the pain becomes large in accordance with the motion of bending the joint. In this manner, it is possible to identify which limb is moved and how the limb is moved when the pain occurs, from the time difference between the problem occurrence time point and the deviation time point of the four limbs. For example, in a case where the deviation occurs between the actual motion waveform and the ideal motion waveform, the problem limb identifying unit 45 may identify the problem occurrence time point (timing t2) at which the deviation disappears immediately before, and may identify the limb which is taken off or lands at the timing closest to the problem occurrence time point as a limb having a problem. In the example of FIG. 27, since the waveform closest to zero at timing t2 is the waveform RH_T of the ground-off of the right hindlimb, the right hindlimb is identified as a limb having a problem.

The output unit 47 outputs various types of outputs regarding the identification result of a limb having a problem. For example, in a case where the limb having a problem is identified, the output unit 47 outputs a screen that displays the name of the identified limb to the display unit 31. In addition, in a case where the limb having a problem is identified by two options, the output unit 47 outputs the screen that displays the names of the limbs which are two options to the display unit 31. In addition, in a case where the limb having a problem is not identified, the output unit 47 outputs the screen that displays the contents that there is no limb having a problem to the display unit 31.

[Processing Flow]

Figures 1, 28A:
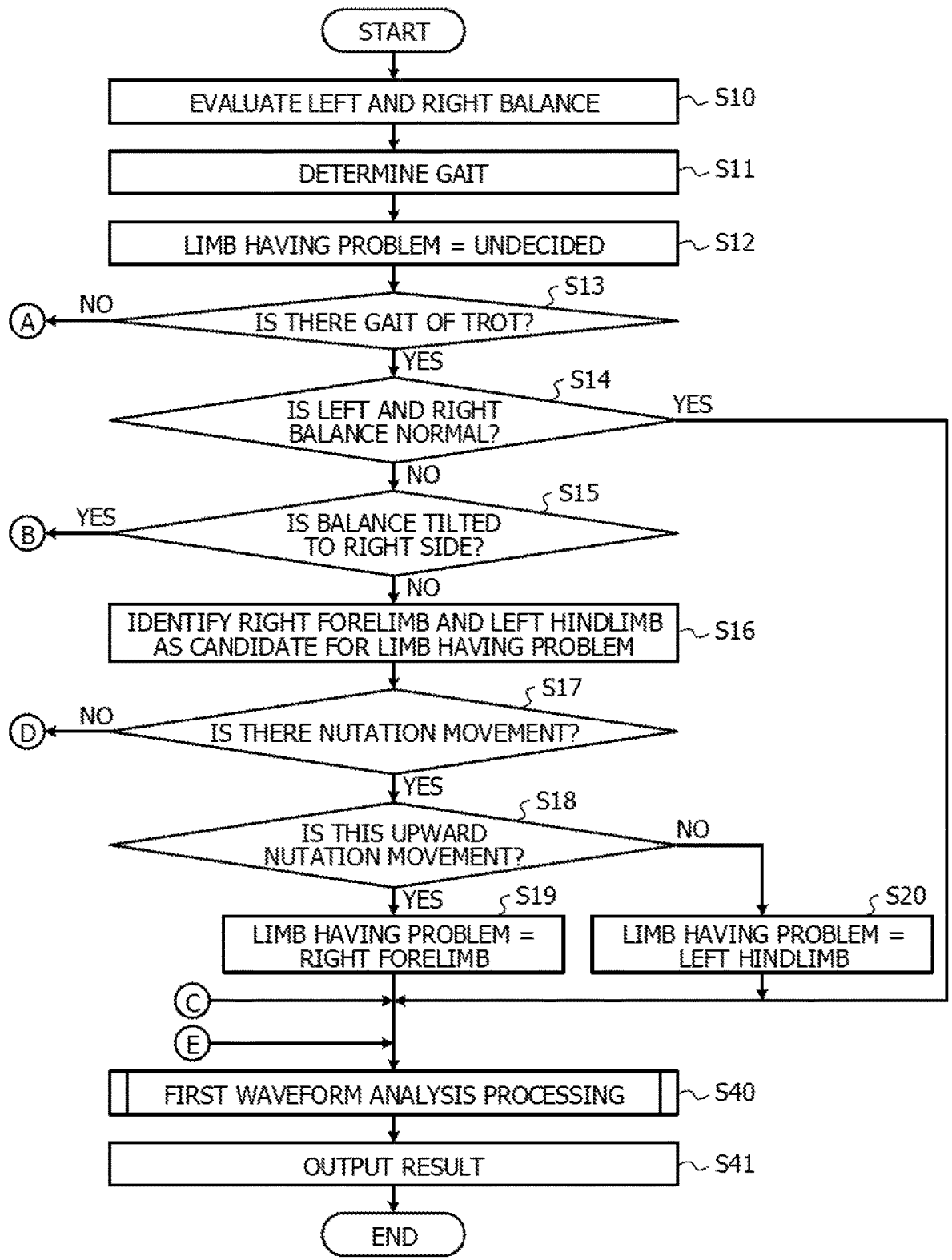
Figures 2, 28A:
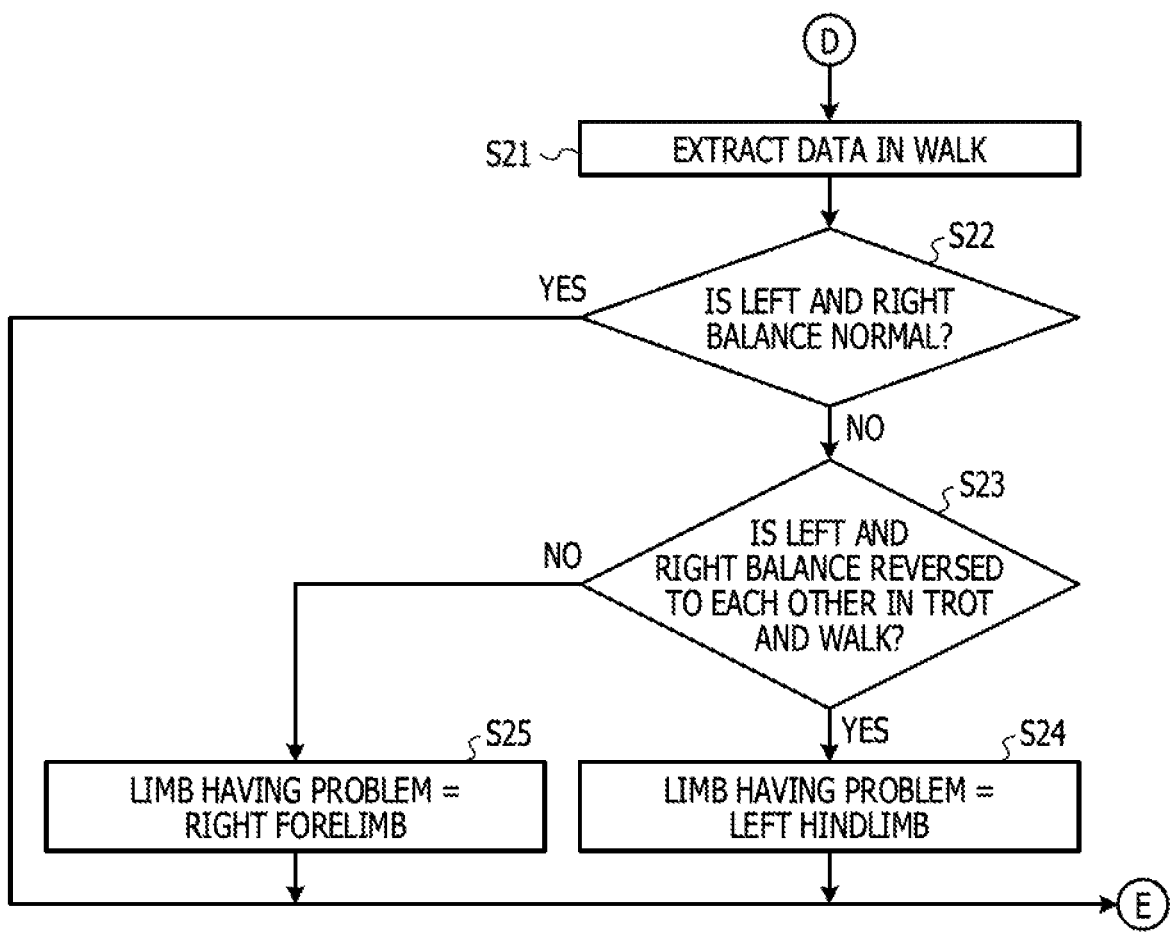

Next, the flow of the estimation processing in which the estimation device 12 according to the example estimates the limb having a problem that causes the lameness will be described. FIG. 28A (i.e. FIGS. 28A-1 and 28A-2) to FIG. 28C (i.e. FIGS. 28C-1 and 28C-2) are flowcharts illustrating an example of a procedure of the estimation processing. The estimation processing is executed at a predetermined timing, for example, at a timing of receiving an instruction to start processing from the input unit 32.

As illustrated in FIG. 28A, the evaluation unit 42 evaluates the left and right balance of the movement of the horse for each walking completion based on the measurement data 35 (S10). For example, the evaluation unit 42 reads out the measurement data 35 and obtains the trajectory of the position in front of the chest of the horse on the plane from the measurement data 35. In addition, the evaluation unit 42 obtains the point P0 which is the maximum point on the left side, the point P1 which is the minimum point on the right side, the point P2 which is the maximum point on the right side, and the point P3 which is the minimum point on the left side, in the trajectory of the position in front of the chest from the trajectory, and evaluates the left and right balance of the trajectory for each walking completion.

For example, the determination unit 43 obtains the value α of the acceleration in the up-down direction and the square β of the absolute value of the acceleration from the measurement data 35, and using α and β, the gait when the horse moves is determined (S11). In addition, the determination unit 43 may determine the gait when the horse moves for each of the plurality of walking completions of the measurement data 35. Further, the determination unit 43 may determine the gait when the horse moves from the data for each of the predetermined periods of the measurement data 35.

The candidate identifying unit 44 initializes the limb having a problem to be undecided (S12). The determination unit 43 determines whether or not there is a trot in the determined gait (S13). In a case where there is no trot in the determined gait (No in S13), the process proceeds to S100 in FIG. 28C which will be described later.

Meanwhile, in a case where there is a trot in the determined gait (Yes in S13), the candidate identifying unit 44 determines whether or not the left and right balance in the trot is normal as a result of evaluating the left and right balance at the time of the movement by the evaluation unit 42 (S14). The candidate identifying unit 44 determines that the left and right balance is normal when there is no tilt in the left and right balance in the trot. In a case where the left and right balance is normal (Yes in S14), the process proceeds to S40 which will be described later.

Meanwhile, in a case where the left and right balance in the trot is not normal (No in S14), the candidate identifying unit 44 determines whether or not the left and right balance is tilted to the right side (S15). In a case where the left and right balance is not tilted to the right side (No in S15), the candidate identifying unit 44 identifies the right forelimb and the left forelimb as the candidates for a limb having a problem (S16).

The problem limb identifying unit 45 determines whether or not the nutation movement has been detected when moving the forelimb and the hindlimb which are considered as the candidates for a limb having a problem from the measurement data 35 (S17). In a case where the nutation movement is detected (Yes in S17), the problem limb identifying unit 45 determines whether or not the upward nutation movement has been detected (S18). In a case where the upward nutation movement is detected (Yes in S18), the problem limb identifying unit 45 identifies the right forelimb as a limb having a problem (S19). Meanwhile, in a case where the upward nutation movement is not detected (No in S18), the problem limb identifying unit 45 identifies the left hindlimb as a limb having a problem (S20). In addition, the process proceeds to S40 which will be described later.

Meanwhile, in a case where the nutation movement is not detected (No in S17), the candidate identifying unit 44 extracts the gait data of walk from the measurement data 35

(S21). The candidate identifying unit 44 determines whether or not the left and right balance in the gait of walk is normal (S22). In a case where the left and right balance is normal (Yes in S22), the process proceeds to S40 which will be described later.

Meanwhile, in a case where the left and right balance is not normal (No in S22), it is determined whether or not the left and right balance is reversed in trot and walk (S23). In a case where the left and right balance is reversed (Yes in S23), the problem limb identifying unit 45 identifies the left hindlimb as a limb having a problem (S24). Meanwhile, in a case where the left and right balance is not reversed (No in S23), the problem limb identifying unit 45 identifies the right forelimb as a limb having a problem (S25). In addition, the process proceeds to S40 which will be described later.

Figure 28B:
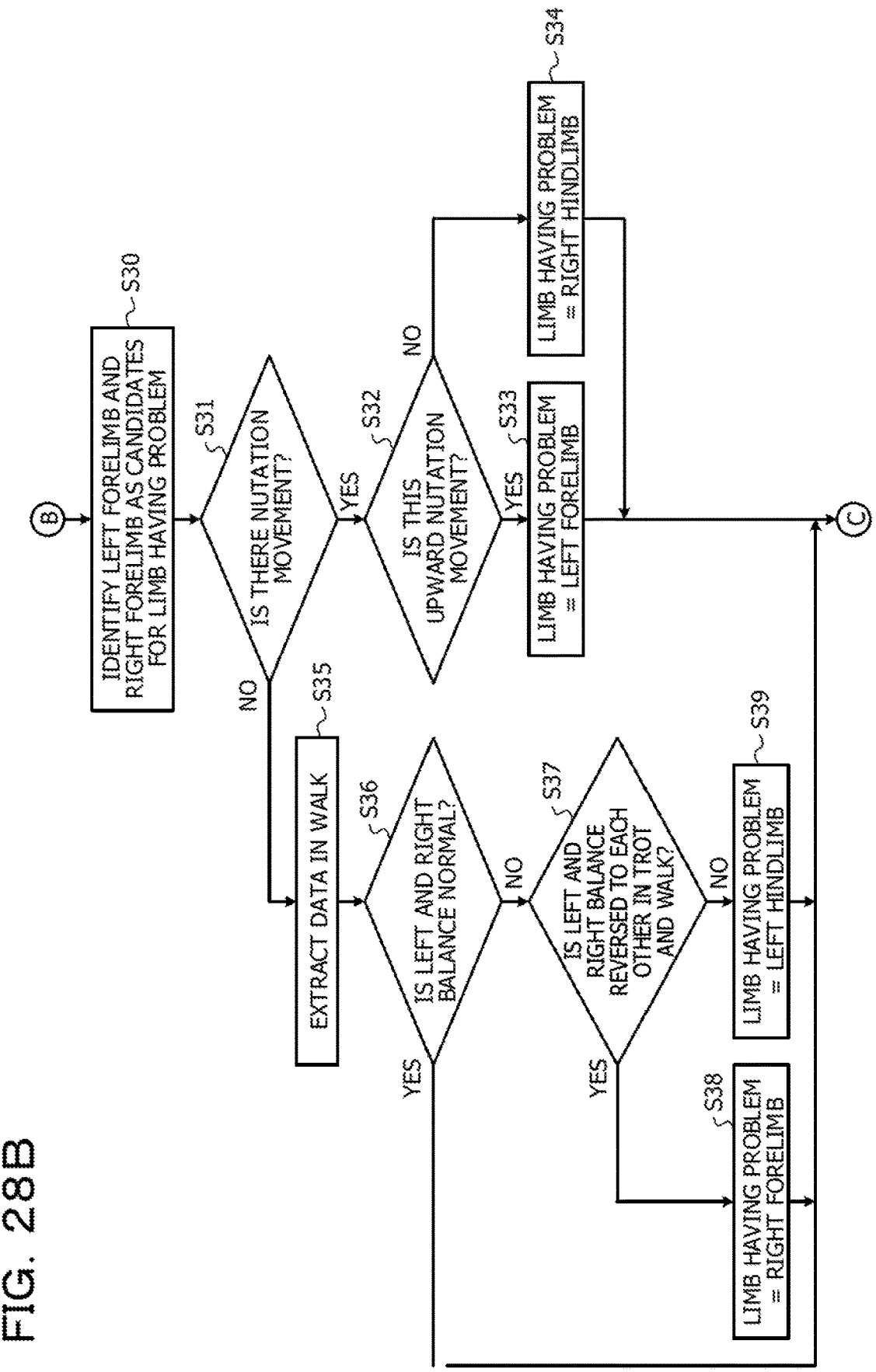
FIG. 28B illustrates a flowchart illustrating an example of a procedure of estimation processing.

Meanwhile, in a case where the left and right balance is tilted to the right side (Yes in S15), as illustrated in FIG. 28B, the candidate identifying unit 44 identifies the left forelimb and the right hindlimb as the candidates for a limb having a problem (S30).

The problem limb identifying unit 45 determines whether or not the nutation movement has been detected when moving the forelimb and the hindlimb which are considered as the candidates for a limb having a problem from the measurement data 35 (S31). In a case where the nutation movement is detected (Yes in S31), the problem limb identifying unit 45 determines whether or not the upward nutation movement has been detected (S32). In a case where the upward nutation movement is detected (Yes in S32), the problem limb identifying unit 45 identifies the left forelimb as a limb having a problem (S33). Meanwhile, in a case where the upward nutation movement is not detected (No in S32), the problem limb identifying unit 45 identifies the right hindlimb as a limb having a problem (S34). In addition, the process proceeds to S40 which will be described later.

Meanwhile, in a case where the nutation movement is not detected (No in S31), the candidate identifying unit 44 extracts the gait data of walk from the measurement data 35 (S35). The candidate identifying unit 44 determines whether or not the left and right balance in the gait of walk is normal (S36). In a case where the left and right balance is normal (Yes in S36), the process proceeds to S40 which will be described later.

Meanwhile, in a case where the left and right balance is not normal (No in S36), it is determined whether or not the left and right balance is reversed in trot and walk (S37). In a case where the left and right balance is reversed (Yes in S37), the problem limb identifying unit 45 identifies the right hindlimb as a limb having a problem (S38). Meanwhile, in a case where the left and right balance is not reversed (No in S37), the problem limb identifying unit 45 identifies the left forelimb as a limb having a problem (S39). In addition, the process proceeds to S40 which will be described later.

As illustrated in FIG. 28A, the problem limb identifying unit 45 executes first waveform analysis processing (S40).

Figure 29:
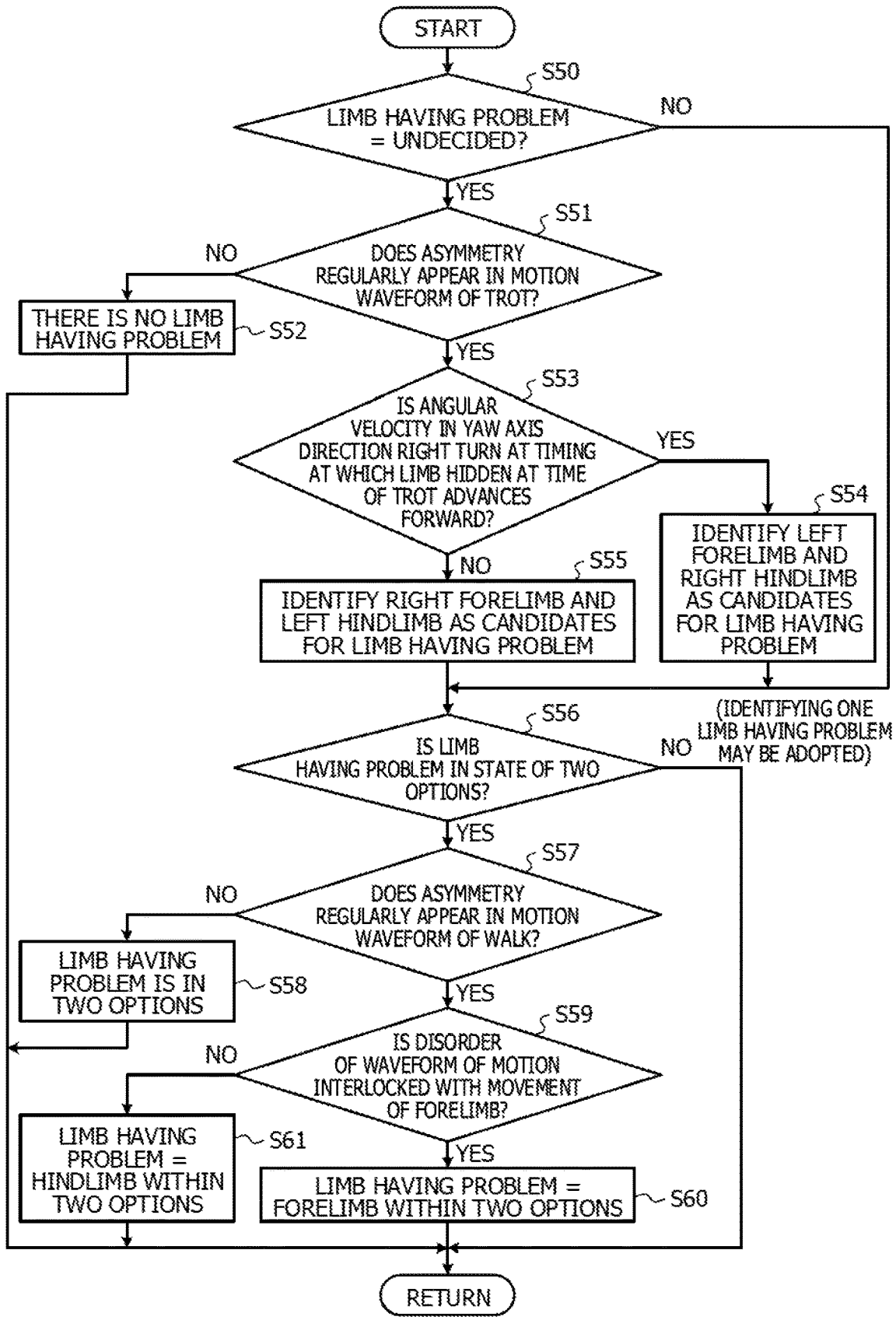
FIG. 29 illustrates a flowchart illustrating an example of a procedure of first waveform analysis processing.

FIG. 29 illustrates a flowchart illustrating an example of a procedure of the first waveform analysis processing. The first waveform analysis processing is executed from S40 of the estimation processing.

As illustrated in FIG. 29, the problem limb identifying unit 45 determines whether or not the limb having a problem is undecided (S50). In a case where the limb having a problem has not yet been identified, it is determined that the limb having a problem is undecided. In a case where the limb having a problem is identified and the limb having a problem is not undecided (No in S50), the process proceeds to S56 which will be described later.

Meanwhile, in a case where the limb having a problem is undecided (Yes in S50), the candidate identifying unit 44 obtains the motion waveforms in any of the up-down direction, the left-right direction, the yaw axis direction, and the front-rear direction when the horse moves in the gait of trot based on the measurement data 35, and determines whether or not asymmetry regularly appears in the motion waveform (S51). In a case where the asymmetry does not regularly appear in the motion waveform (No in S51), the problem limb identifying unit 45 identifies that there is no limb having a problem (S52), and the process proceeds to S41 of the estimation processing.

Meanwhile, in a case where the asymmetry regularly appears in the motion waveform (Yes in S51), the candidate identifying unit 44 determines whether or not the yaw axis turns rightward at the timing of advancing the hidden limb (S53). Here, for example, when the lameness occurs, the horse hides the limb in which the lameness occurs, and thus, the motion waveform of the acceleration in the up-down direction when moving the limb in which the lameness occurs becomes small. For example, the candidate identifying unit 44 determines whether or not the yaw axis turns rightward at the timing when the motion waveform smaller than a predetermined ratio is generated in the up-down direction. In a case where the yaw axis turns rightward (Yes in S53), the candidate identifying unit 44 identifies the left forelimb and the right hindlimb as the candidates for a limb having a problem (S54). Meanwhile, in a case where the yaw axis turns leftward and does not turn rightward (Yes in S53), the candidate identifying unit 44 identifies the right forelimb and the left hindlimb as the candidates for a limb having a problem (S55).

The problem limb identifying unit 45 determines whether or not the limbs having a problem are in a state of two options as the candidates for a limb having a problem (S56). In a case where the limbs having a problem have already been identified and are not in the state of two options (No in S56), the process proceeds to S41 of the estimation processing.

Meanwhile, in a case where the limb having a problem is in the state of two options (Yes in S56), the problem limb identifying unit 45 obtains the motion waveforms in any of the up-down direction, the left-right direction, and the yaw axis direction when the horse moves in the gait of walk, and determines whether or not the asymmetric motion waveform regularly appears in the motion waveform (S57). In a case where the asymmetric motion waveform does not regularly appear (No in S57), the problem limb identifying unit 45 identifies that the limb having a problem is in a state of two options (S58), and the process proceeds to S41 of the estimation processing.

Meanwhile, in a case where the asymmetric motion waveform regularly appears (Yes at S57), the problem limb identifying unit 45 determines whether or not the asymmetric disorder is interlocked with the movement of the forelimb (S59). In a case where the asymmetric disorder is interlocked with the movement of the forelimb (Yes in S59), the problem limb identifying unit 45 identifies the forelimb among the candidates for a limb having a problem as a limb having a problem (S60), and the process proceeds to S41 of the estimation processing.

Meanwhile, in a case where the asymmetric disorder is not interlocked with the movement of the forelimb (Yes in S59), the problem limb identifying unit 45 identifies the hindlimb among the candidates for a limb having a problem as a limb having a problem (S61), and the process proceeds to S41 of the estimation processing.

Returning to FIG. 28A, the output unit 47 outputs the identified limb having a problem (S41) and ends the processing. For example, in a case where the limb having a problem is identified, the output unit 47 outputs a screen that displays the name of the identified limb to the display unit 31. In addition, in a case where the limb having a problem is identified by two options, the output unit 47 outputs the screen that displays the names of the limbs which are two options to the display unit 31. In addition, in a case where the limb having a problem is not identified, the output unit 47 outputs the screen that displays the contents that there is no limb having a problem to the display unit 31.

Figures 1, 28C:
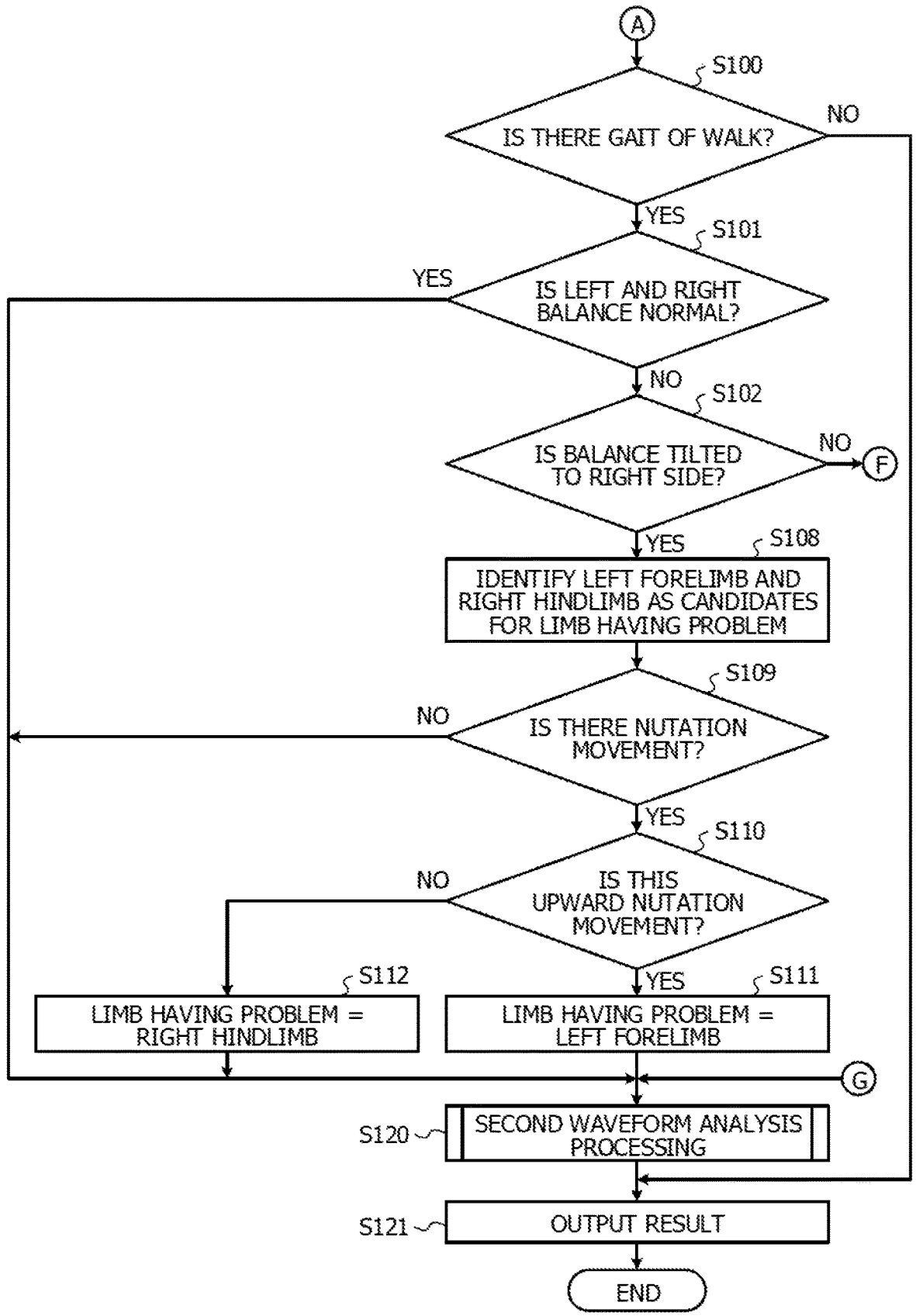
Figures 2, 28C:
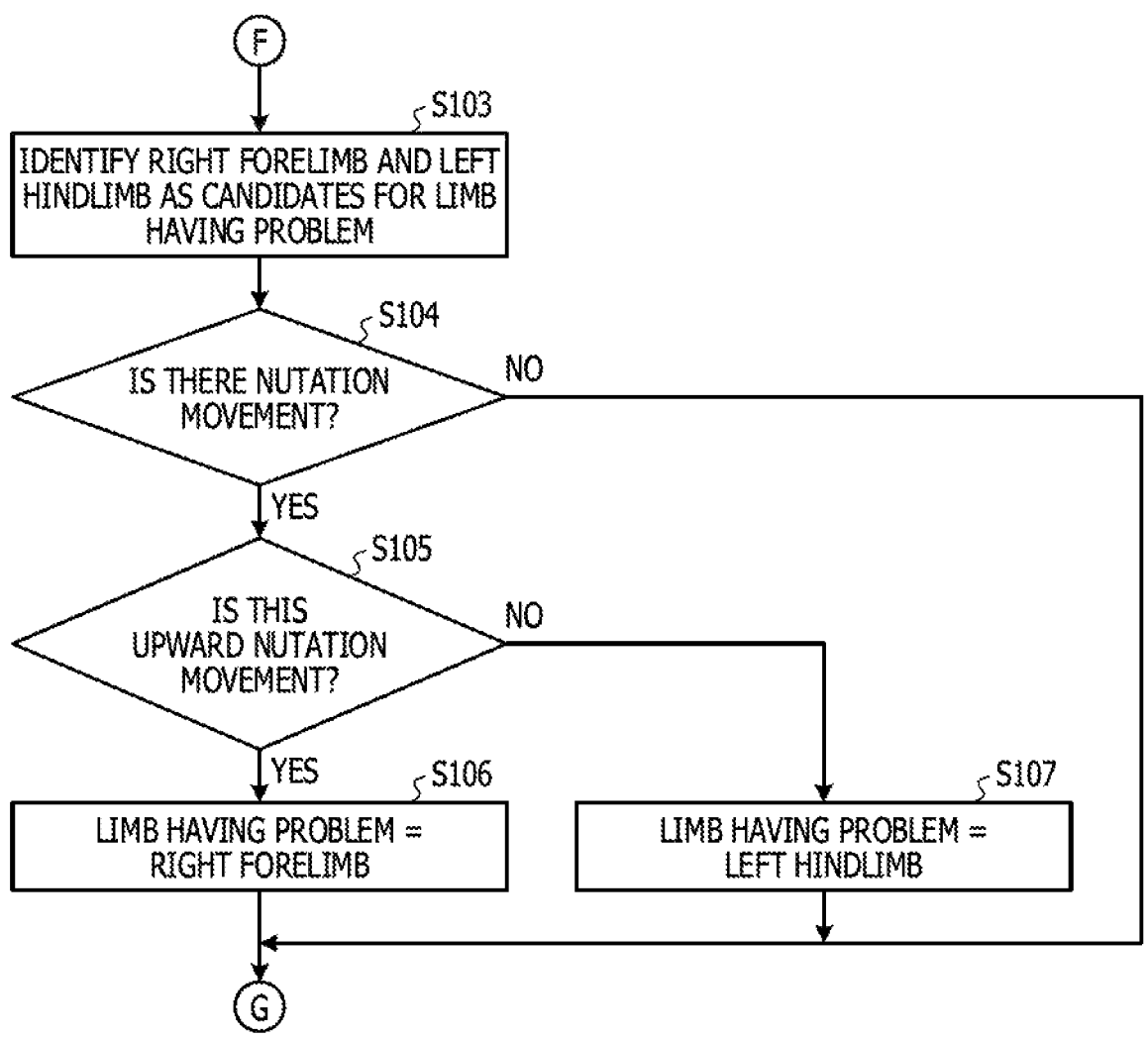

Meanwhile, in a case where there is no trot in the determined gait (No in S13), as illustrated in FIG. 28C, the determination unit 43 determines whether or not there is a walk in the determined gait (S100). In a case where there is no walk in the determined gait (No in S100), the process proceeds to S121 will be described later.

Meanwhile, in a case where there is a walk in the determined gait (Yes in S100), the candidate identifying unit 44 determines whether or not the left and right balance in the walk is normal as a result of evaluating the left and right balance at the time of the movement by the evaluation unit 42 (S101). The candidate identifying unit 44 determines that the left and right balance is normal when there is no tilt in the left and right balance in the walk. In a case where the left and right balance is normal (Yes in S101), the process proceeds to S120 which will be described later.

Meanwhile, in a case where the left and right balance in the walk is not normal (No in S101), the candidate identifying unit 44 determines whether or not the left and right balance is tilted to the right side (S102). In a case where the left and right balance is not tilted to the right side (No in S102), the candidate identifying unit 44 identifies the right forelimb and the left forelimb as the candidates for a limb having a problem (S103).

The problem limb identifying unit 45 determines whether or not the nutation movement has been detected when moving the forelimb and the hindlimb which are considered as the candidates for a limb having a problem from the measurement data 35 (S104). In a case where the nutation movement is detected (Yes in S104), the problem limb identifying unit 45 determines whether or not the upward nutation movement has been detected (S105). In a case where the upward nutation movement is detected (Yes in S105), the problem limb identifying unit 45 identifies the right forelimb as a limb having a problem (S106). Meanwhile, in a case where the upward nutation movement is not detected (No in S105), the problem limb identifying unit 45 identifies the left hindlimb as a limb having a problem (S107). In addition, the process proceeds to S120 which will be described later. Further, in a case where the nutation movement is not detected (No in S104), the process proceeds to S120 will be described later.

Meanwhile, in a case where the left and right balance is tilted to the right side (Yes in S102), the candidate identifying unit 44 identifies the left forelimb and the right hindlimb as the candidates for a limb having a problem (S108).

The problem limb identifying unit 45 determines whether or not the nutation movement has been detected when moving the forelimb and the hindlimb which are considered as the candidates for a limb having a problem from the measurement data 35 (S109). In a case where the nutation movement is detected (Yes in S109), the problem limb identifying unit 45 determines whether or not the upward nutation movement has been detected (S110). In a case where the upward nutation movement is detected (Yes in S110), the problem limb identifying unit 45 identifies the left forelimb as a limb having a problem (S111). Meanwhile, in a case where the upward nutation movement is not detected (No in S110), the problem limb identifying unit 45 identifies the right hindlimb as a limb having a problem (S112). In addition, the process proceeds to S120 which will be described later. Further, in a case where the nutation movement is not detected (No in S109), the process proceeds to S120 will be described later.

The problem limb identifying unit 45 executes second waveform analysis processing (S120).

Figure 30:
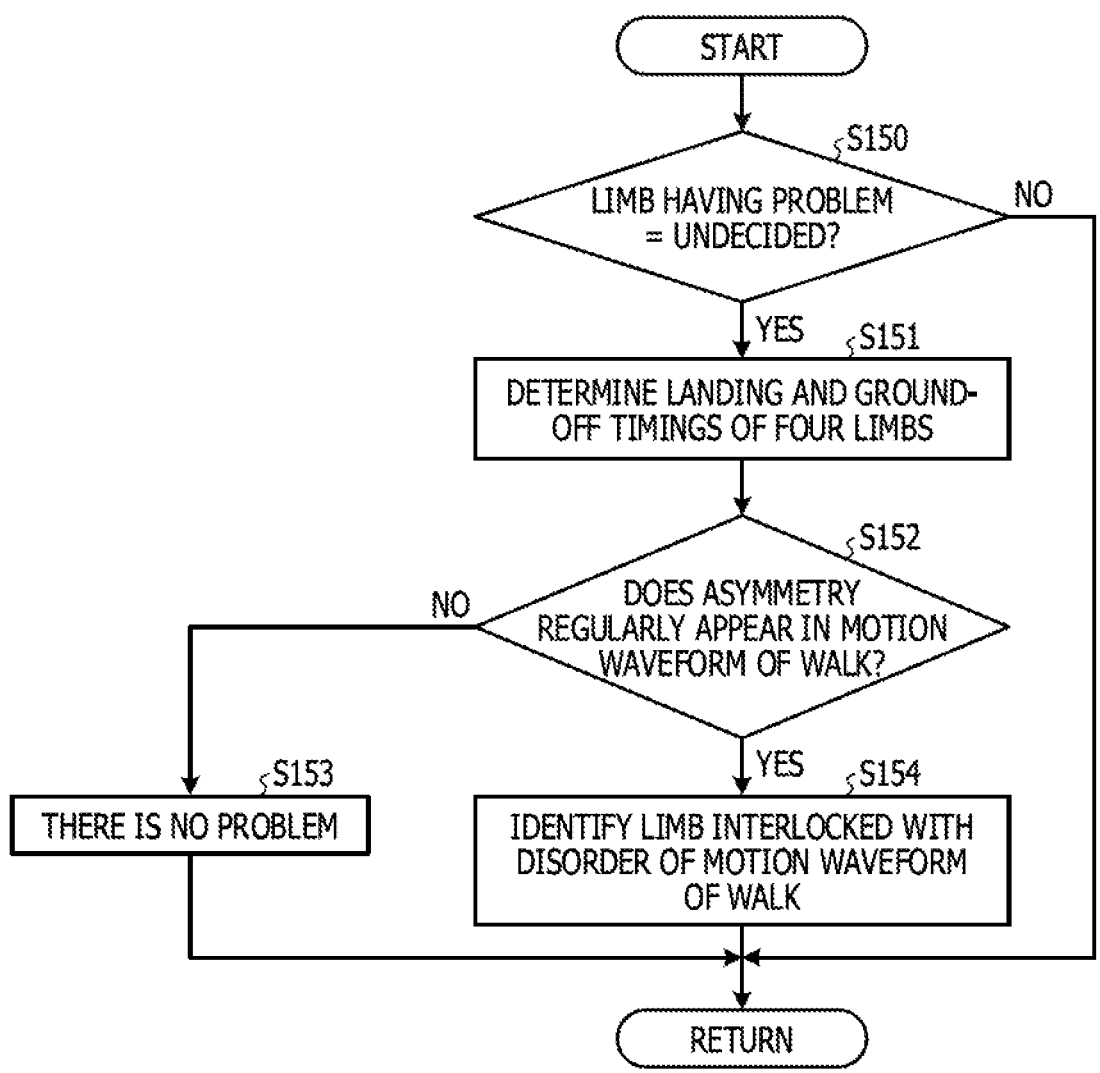
FIG. 30 illustrates a flowchart illustrating an example of a procedure of second waveform analysis processing.

FIG. 30 illustrates a flowchart illustrating an example of a procedure of the second waveform analysis processing. The second waveform analysis processing is executed from S120 of the estimation processing.

As illustrated in FIG. 30, the problem limb identifying unit 45 determines whether or not the limb having a problem is undecided (S150). In a case where the limb having a problem has not yet been identified, it is determined that the limb having a problem is undecided. In a case where the limb having a problem is identified and the limb having a problem is not undecided (No in S150), the process proceeds to S121 of the estimation processing.

Meanwhile, in a case where the limb having a problem is undecided (Yes in S150), the distinguishing unit 46 distinguishes the ground-off and landing timings of each of the four limbs of the horse from the motion waveforms when the horse moves in the gait of walk (S151). For example, the distinguishing unit 46 obtains the motion waveforms in the up-down direction and in the yaw axis direction when the horse moves in the gait of walk, and distinguishes the ground-off and landing timings of each of the four limbs of the horse from the motion waveforms in the up-down direction and in the yaw axis direction.

The candidate identifying unit 44 obtains the motion waveforms in any of the up-down direction, the left-right direction, the yaw axis direction, and the front-rear direction when the horse moves in the gait of trot based on the measurement data 35, and determines whether or not asymmetry regularly appears in the motion waveform (S152). In a case where the asymmetry does not regularly appear in the motion waveform (No in S152), the problem limb identifying unit 45 identifies that there is no limb having a problem (S153), and the process proceeds to S121 of the estimation processing.

Meanwhile, in a case where the asymmetry regularly appears in the motion waveform (Yes at S152), the problem limb identifying unit 45 identifies the limb having a problem which is interlocked with the disorder of the motion waveform based on the ground-off and landing timings of each of the four limbs of the horse distinguished by the distinguishing unit 46 (S154), and the process proceeds to S121 of the estimation processing.

Returning to FIG. 28C, the output unit 47 outputs the identified limb having a problem (S121) and ends the processing. For example, in a case where the limb having a problem is identified, the output unit 47 outputs a screen that displays the name of the identified limb to the display unit 31. In addition, in a case where the limb having a problem is identified by two options, the output unit 47 outputs the screen that displays the names of the limbs which are two options to the display unit 31. In addition, in a case where the limb having a problem is not identified, the output unit 47 outputs the screen that displays the contents that there is no limb having a problem to the display unit 31.

[Effects]

As described above, the estimation device 12 according to the example distinguishes the ground-off and landing timings of each of the four limbs of the horse based on the measurement data 24 of the motion sensor mounted on the horse. The estimation device 12 identifies the limb interlocked with the disorder of the motion waveform based on the ground-off and landing timings of each of the four limbs of the distinguished horse. Accordingly, the estimation device 12 can estimate the limb having a problem which causes the lameness in a state with the burden on the horse is small.

Further, the estimation device 12 according to the example determines the gait of the animal based on the measurement data 24. The estimation device 12 distinguishes the ground-off and landing timings of each of the limbs of the horse from the motion waveform when the horse moves in the gait of walk. Here, the walk is the basis of the exercise of the horse which is introduced at production and breeding ranches. The estimation device 12 can estimate the limb having a problem that causes the lameness from the motion waveform of the walk, and accordingly, the estimation device 12 can estimate the limb having a problem even when the trot in which the lameness is easily found is intentionally incorporated in a training menu. In addition, the exercise of the horses by a walking machine introduced in many ranches is done unattended. The gait at the exercise by the walking machine is only a walk. The estimation device 12 can estimate the limb having a problem that causes the lameness from the motion waveform of the walk, and accordingly, for example, it is possible to detect an abnormal gait during the exercise by the walking machine.

In addition, the estimation device 12 according to the example distinguishes the ground-off and landing timings of each of the four limbs of the horse from the motion waveforms in the up-down direction and in the yaw axis direction when the horse moves in the gait of walk. The estimation device 12 identifies a limb having an abnormality based on the motion waveforms in at least one of the left-right direction, the front-rear direction, the up-down direction, and the yaw axis direction. Accordingly, the estimation device 12 can distinguish the ground-off and landing timings of each of the four limbs of the horse, and can estimate the limb having a problem that causes the lameness with high accuracy.

In addition, the estimation device 12 according to the example distinguishes the point of time at which the positive side and negative side of the acceleration in the yaw axis direction are reversed, as the ground-off timing of the right forelimb in a case where the acceleration in the yaw axis direction increases in the left turn direction from the point of time and the ground-off timing of the left forelimb in a case where the acceleration in the yaw axis direction increases in the right turn direction from the point of time. In addition, the estimation device 12 distinguishes the point of time at which the acceleration in the up-down direction is reversed from the negative side to the positive side, as the landing timing of the right forelimb in a case where the yaw axis direction is the left turn direction at the point of time and the landing timing of the left forelimb in a case where the yaw axis direction is the right turn direction at the point of time. Further, the estimation device 12 distinguishes an intermediate timing between the ground-off timing of the right forelimb and the ground-off timing of the left forelimb as the ground-off timing of the left hindlimb. In addition, the estimation device 12 distinguishes an intermediate timing between the ground-off timing of the left forelimb and the ground-off timing of the right forelimb as the ground-off timing of the right hindlimb. Further, the estimation device 12 distinguishes an intermediate timing between the landing timing of the right forelimb and the landing timing of the left forelimb as the landing timing of the left hindlimb. In addition, the estimation device 12 distinguishes an intermediate timing between the landing timing of the left forelimb and the landing timing of the right forelimb as the landing timing of the right hindlimb. Accordingly, the evaluation device 12 can obtain the ground-off and landing timings of each of the four limbs of the horse.

In addition, the estimation device 12 according to the example identifies a limb having a small motion waveform in the front-rear direction as a limb having an abnormality among the limbs having the ground-off timing and the landing timing in the waveform with a large peak in the motion waveform in the left-right direction. Accordingly, the estimation device 12 can estimate the limb having a problem with high accuracy.

In addition, the estimation device 12 according to the example identifies a limb in which the ground-off and landing timings correspond to a period during which the actual motion waveform deviates from the ideal motion waveform by a predetermined ratio or more, as a limb having a problem. Accordingly, the estimation device 12 can estimate the limb having a problem with high accuracy.

Example 2

Next, Example 2 will be described. In Example 2, a case where the estimation device 12 is a portable terminal device will be described. Since the configurations of the system 10 and the measurement device 11 according to Example 2 is the same as those of Example 1 illustrated in FIGS. 1 and 3, the description thereof will be omitted.

Figure 31:
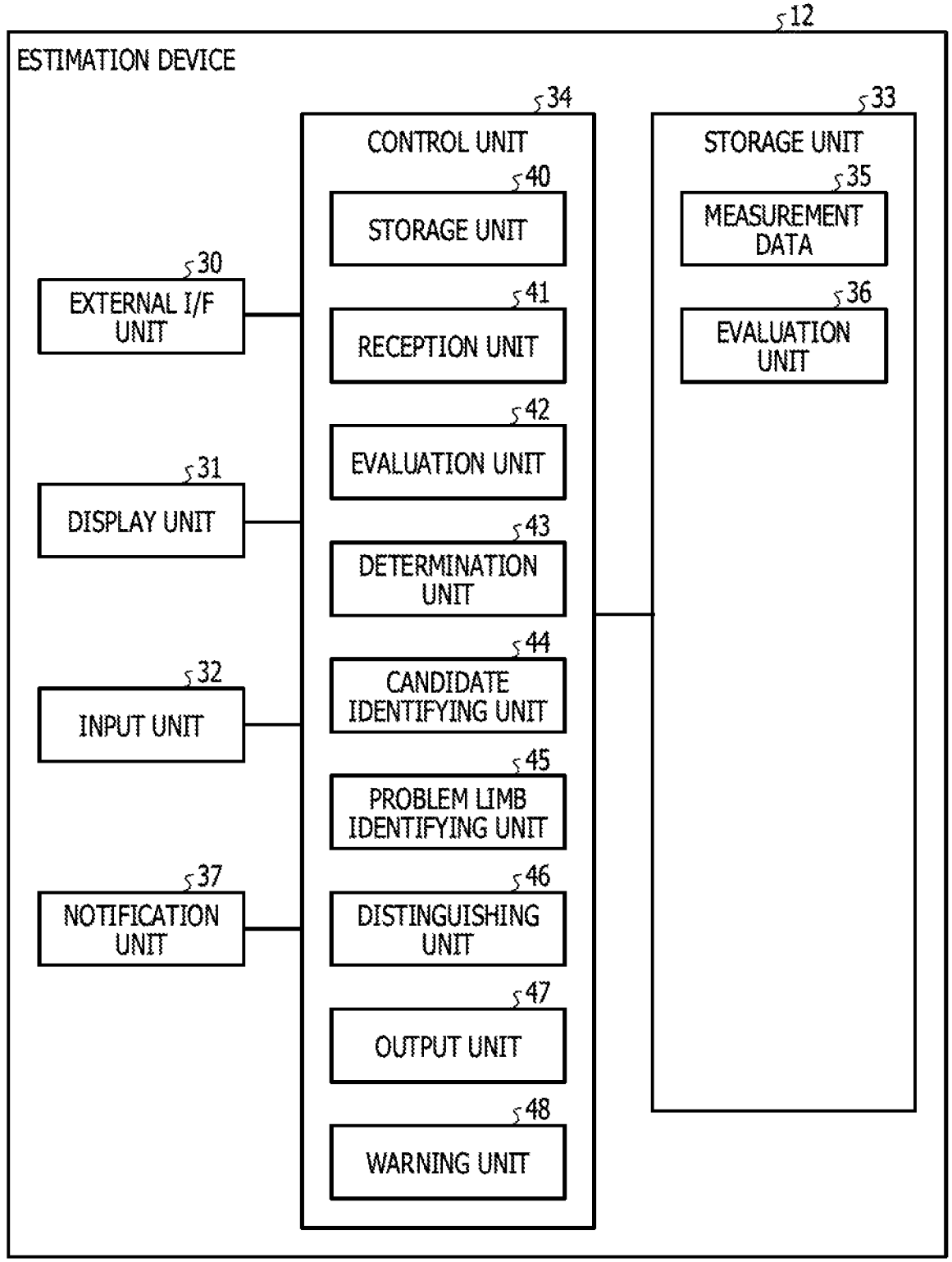
FIG. 31 illustrates a diagram illustrating an example of a functional configuration of an estimation device according to Example 2.

FIG. 31 illustrates a diagram illustrating an example of a functional configuration of the estimation device according to Example 2. Since the configuration of the estimation device 12 according to Example 2 is mostly the same as that of Example 1 illustrated in FIG. 4, the same parts are denoted by the same reference numerals, and different parts will be mainly described.

As illustrated in FIG. 31, the estimation device 12 further includes a notification unit 37.

The notification unit 37 is a device which performs notification. For example, the notification unit 37 is a vibrator for notification by vibration or a speaker for notification by sound.

Further, the control unit 34 further includes a warning unit 48.

The warning unit 48 performs various types of warning. For example, in a case where a state where the left and right balance is deviated to any one side is detected in the evaluation of the plurality of times of walking completions by the evaluation unit 42, the warning unit 48 controls the notification unit 37 and generates a warning. For example, the warning unit 48 generates a warning in a case where the ratio of the left or right side is equal to or greater than a predetermined threshold value (for example, 80%) considered to be deviated toward one side in the evaluation of the latest predetermined period or a predetermined number of walking completions. The threshold value may be externally settable. Further, for example, the warning unit 48 controls the notification unit 37 and generates a warning in a case where the limb having a problem is identified as a specific limb or a state of two options.

Figure 32:
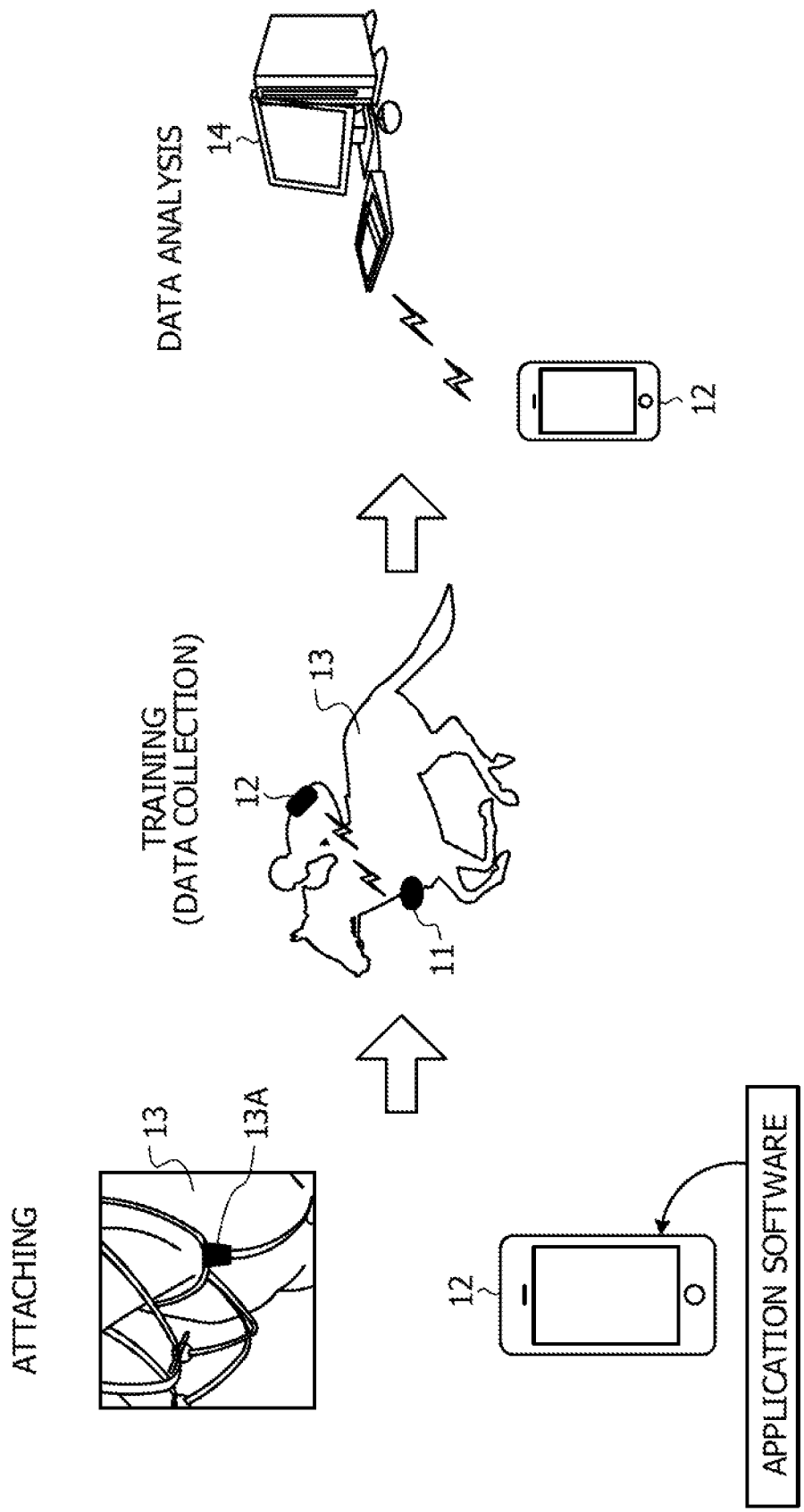
FIG. 32 illustrates a view illustrating an example of a flow of health management of the horse by a system according to Example 2.

FIG. 32 is a view illustrating an example of a flow of health management of the horse by the system according to Example 2. The measurement device 11 is attached in front of the chest of the horse 13 which is a target of the health management. Further, for example, application software is installed on the smartphone to cause the smartphone to function as the estimation device 12.

A person in charge of training the horse 13 possesses the estimation device 12 and trains the horse 13. The estimation device 12 and the measurement device 11 can communicate with each other by short-range wireless communication, such as Bluetooth (registered trademark). The estimation device 12 receives the measurement data 24 from the measurement device 11 at any time and evaluates the left and right balance in real time. As a result of the evaluation, the estimation device 12 generates a warning in a case where a state where the left and right balance is deviated to any one side is detected in the evaluation of the plurality of times of walking completions. In addition, the estimation device 12 generates a warning in a case where the limb having a problem is identified as a specific limb or a state of two options, and displays the limb having a problem and a specific limb or a state of two options. Accordingly, since the estimation device 12 can detect the lameness in real time during the training and generate a warning, the generation of an abnormality can be detected in an early stage. For example, in a case where the lameness is detected during the training, the estimation device 12 can stop the training by generating a warning, and it is possible to suppress deterioration of the abnormality of the limb.

After the training, the estimation device 12 is brought to the management office, and the measurement data 35 or the evaluation data 36 is uploaded to a terminal device 14 via the storage medium or by wired communication or wireless communication. The terminal device 14 manages the uploaded measurement data 35 or the evaluation data 36. In addition, the terminal device 14 may perform more detailed analysis on the health management of the horse 13 using the measurement data 35 or the evaluation data 36.

[Effects]

As described above, in a case where the lameness is detected during the training, the estimation device 12 according to the example generates a warning, and accordingly, it is possible to suppress deterioration of the abnormality in a case where the abnormality of the limb is generated. As described above, the walk is the basis of the exercise of the horse which is introduced at production and breeding ranches. In the training at horse racing and horseback riding, warming-up starts with a walk. Therefore, the estimation device 12 can estimate the limb having a problem that causes the lameness from the motion waveform of the walk, and accordingly, it is possible to estimate the limb having a problem in the warming-up.

Example 3

Although the examples related to the devices disclosed so far have been described, the disclosed technology may be implemented in various different aspects in addition to the above-described examples. Here, another example included in the present invention will be described below.

Figure 33:
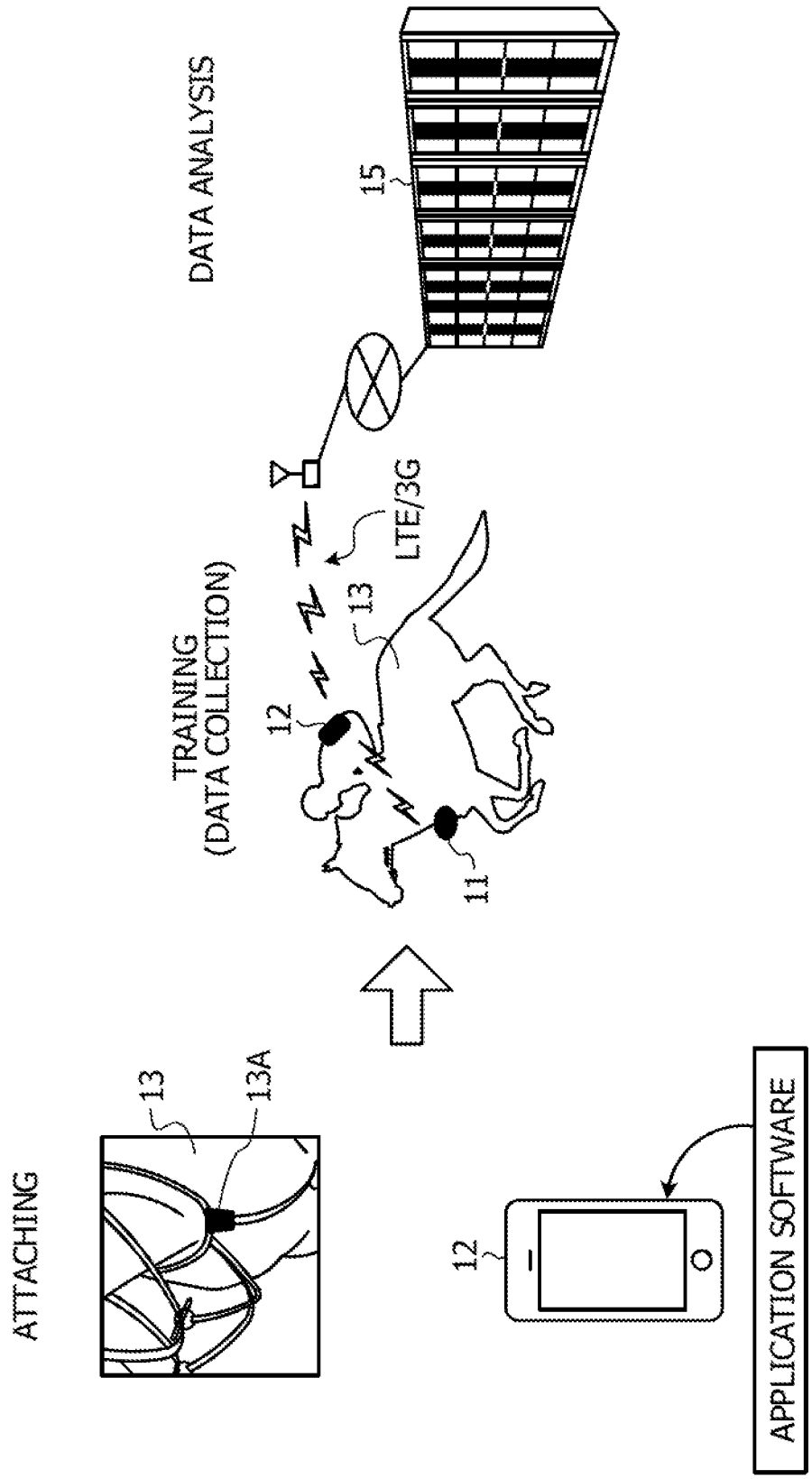
FIG. 33 illustrates a view illustrating an example of a flow of health management of the horse by a system according to Example 3.

For example, in Example 2 described above, a case where the estimation device 12 uploads the measurement data 35 or the evaluation data 36 to the terminal device 14 of the management office was described as an example. However, the present invention is not limited thereto. For example, the estimation device 12 may upload the measurement data 35 or the evaluation data 36 to a server device on the cloud. FIG. 33 is a view illustrating an example of a flow of health management of the horse by the system according to Example 3. For example, the estimation device 12 may upload the measurement data 35 or the evaluation data 36 to a server device 15 on the cloud via a mobile communication network. The server device 15 manages the uploaded measurement data 35 or the evaluation data 36. In addition, the server device 15 may perform more detailed analysis on the health management of the horse 13 using the measurement data 35 or the evaluation data 36. In this manner, by managing or analyzing the measurement data 35 or the evaluation data 36 in the server device 15 on the cloud, the trainer or the like can grasp the health condition of the horse 13 by accessing the server device 15 even when the trainer is out of the office.

Further, in the above-described example, a case applied to detection of lameness of the horse was described as an example. However, the present invention is not limited thereto. In an animal moving on four limbs, when some abnormalities are generated in the four limbs, the lameness occurs by hiding the limb in which the abnormality has generated. Accordingly, the estimation device 12 can be used to detect the lameness of the animal moving on four limbs.

Further, in the above-described example, a case where the limb having a problem is identified from the motion waveform of the walk in a case where the limb having a problem is not identified by performing the evaluation of the left and right balance and the detection of the nutation movement, is described as an example. However, the present invention is not limited thereto. The evaluation device 12 may identify the limb having a problem from the motion waveform of the walk without performing the evaluation of the left and right balance and the detection of the nutation movement.

In addition, each configuration elements of each device illustrated in the drawings is functionally conceptual, and is not necessarily physically configured as similar as the drawing. In other words, a specific state of distribution and integration of each device is not limited to those illustrated in the drawing, and all or a part thereof can be distributed and integrated functionally or physically in any unit according to various loads or usage situations. For example, each of the processing units of the storage unit 40, the reception unit 41, the evaluation unit 42, the determination unit 43, the candidate identifying unit 44, the problem limb identifying unit 45, the distinguishing unit 46, and the output unit 47 may be appropriately integrated with each other. In addition, the processing of each of the processing units may be appropriately separated into processing of a plurality of processing units. Furthermore, all or any part of each processing function performed in each of the processing units is realized by the CPU and a program analyzed and executed by the CPU, or can be realized as hardware by wired logic.

[Estimation Program]

Figure 34:
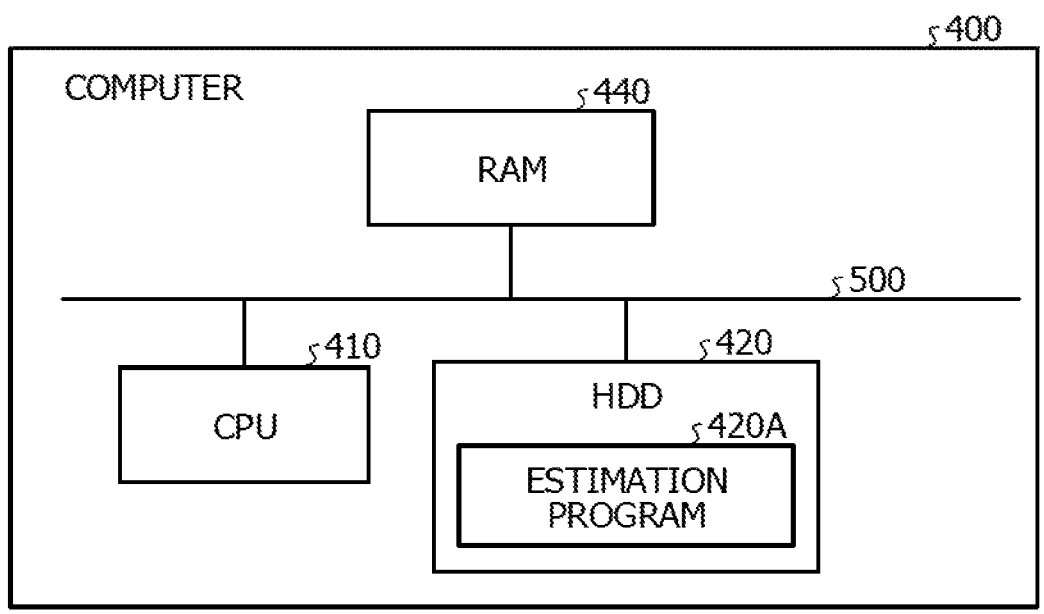
FIG. 34 illustrates a diagram illustrating an example of a configuration of a computer that executes an estimation program.

In addition, various types of processing described in the above-described examples can also be realized by executing a prepared program on a computer system, such as a personal computer or a workstation, in advance. Here, hereinafter, an example of the computer system that executes the program having the same function as those of the above-described examples will be described. FIG. 34 illustrates a diagram illustrating an example of a configuration of a computer that executes the estimation program.

As illustrated in FIG. 34, a computer 400 includes a central processing unit (CPU) 410, a hard disk drive (HDD) 420, and a random access memory (RAM) 440. Each of the units 400 to 440 is connected to each other via a bus 500.

An estimation program 420A which functions similar to the storage unit 40, the reception unit 41, the evaluation unit 42, the determination unit 43, the candidate identifying unit 44, the problem limb identifying unit 45, the distinguishing unit 46, and the output unit 47, is stored in the HDD 420 in advance. In addition, the estimation program 420A may be appropriately separated.

Further, the HDD 420 stores various types of information. For example, the HDD 420 stores various types of data used for determining the OS or the order quantity.

In addition, the CPU 410 reads out and executes the estimation program 420A from the HDD 420, and accordingly, the CPU 410 executes the same operation as that of each of the processing units of the example. In other words, the estimation program 420A executes similar operations as those of the storage unit 40, the reception unit 41, the evaluation unit 42, the determination unit 43, the candidate identifying unit 44, the problem limb identifying unit 45, the distinguishing unit 46, and the output unit 47.

In addition, the above-described estimation program 420A is not necessarily stored in the HDD 420 from the beginning.

For example, the program is stored in "portable physical medium", such as a flexible disk (FD), a CD-ROM, a DVD disk, a magnetooptic disk, or an IC card, inserted into the computer 400. In addition, the computer 400 may read out and execute the program from the mediums.

Furthermore, the program is stored in "another computer (or server)" or the like connected to the computer 400 via a public line, the Internet, a LAN, a WAN, or the like. In addition, the computer 400 may read out and execute the program from the mediums.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present invention have been described in detail, it should be understood that the various changes, substitutions, and alterations could be made hereto without departing from the spirit and scope of the invention.

What is claimed is:

1. An estimation method performed by a computer, the method comprising:
    executing a distinguishing process that includes distinguishing ground-off and landing timings of respective four limbs of an animal based on measurement data acquired by using a motion sensor attached in front of a chest region of the animal which has four limbs used to move in a quadrupedal manner, the measurement data indicating a movement of the chest region of the animal which has been measured by the motion sensor, and
    executing a identifying process that includes identifying a limb which interlocks with a disorder of a motion waveform upon movement of the animal, based on the distinguished ground-off and landing timings of each of the four limbs of the animal.

2. The estimation method according to claim 1, the method further comprising:
    executing a determining process that includes determining a gait of the animal based on the measurement data,
    wherein the distinguishing process is configured to distinguish the ground-off and landing timings of each of the four limbs of the animal from the motion waveform upon the movement of the animal when the gait of the animal is determined as a walk state.

3. The estimation method according to claim 2,
    wherein the distinguishing process is configured to distinguish the ground-off and landing timings of each of the four limbs of the animal from motion waveforms in an up-down direction and in a yaw axis direction when the gait of the animal is determined as the walk state, and
    wherein the identifying process is configured to identify a limb having an abnormality based on the motion waveforms in at least one of a left-right direction, a front-rear direction, the up-down direction, and the yaw axis direction.

4. The estimation method according to claim 2,
    wherein the distinguishing process includes
    distinguishing a first point of time at which a positive side and a negative side of acceleration in a yaw axis direction are reversed to each other as the ground-off timing of a right forelimb when the acceleration in the yaw axis direction increases in a left turn direction from the point of time,
    distinguishing the first point of time as the ground-off timing of a left forelimb when the acceleration in the yaw axis direction increases in a right turn direction from the point of time,
    distinguishing a point of time at which the negative side of acceleration in an up-down direction is reversed into the positive side of acceleration as the landing timing of the right forelimb when the yaw axis direction is the left turn direction at the point of time,
    distinguishing a point of time at which the negative side of acceleration in the up-down direction is reversed into the positive side of acceleration as the landing timing of the left forelimb when the yaw axis direction is the right turn direction at the point of time,
    distinguishing an intermediate timing between the ground-off timing of the right forelimb and the ground-off timing of the left forelimb as the ground-off timing of a left hindlimb,
    distinguishing an intermediate timing between the ground-off timing of the left forelimb and the ground-off timing of the right forelimb as the ground-off timing of the right hindlimb,
    distinguishing an intermediate timing between the landing timing of the right forelimb and the landing timing of the left forelimb as the landing timing of the left hindlimb, and
    distinguishing an intermediate timing between the landing timing of the left forelimb and the landing timing of the right forelimb as the landing timing of the right hindlimb.

5. The estimation method according to claim 1,
    wherein the identifying process is configured to identify a limb having a small motion waveform in a front-rear direction as a limb having an abnormality among the limbs having the ground-off timing and the landing timing in a waveform with a large peak in the motion waveform in a left-right direction.

6. The estimation method according to claim 1,
wherein the identifying process is configured to identify a limb in which the ground-off and landing timings correspond to a period during which an actual motion waveform deviates from an ideal motion waveform by a predetermined ratio or more, as a limb having a problem.

7. An information processing apparatus for estimating a motion of an animal, the apparatus comprising:
a memory; and
a processor coupled to the memory and configured to
execute a distinguishing process that includes distinguishing ground-off and landing timings of respective four limbs of the animal based on measurement data acquired by using a motion sensor attached in front of a chest region of the animal which has four limbs used to move in a quadrupedal manner, the measurement data indicating a movement of the chest region of the animal which has been measured by the motion sensor, and
execute a identifying process that includes identifying a limb which interlocks with a disorder of a motion waveform upon movement of the animal, based on the distinguished ground-off and landing timings of each of the four limbs of the animal.

8. The information processing apparatus according to claim 7,
wherein the processor is configured to execute a determining process that includes determining a gait of the animal based on the measurement data, and
wherein the distinguishing process is configured to distinguish the ground-off and landing timings of each of the four limbs of the animal from the motion waveform upon the movement of the animal when the gait of the animal is determined as a walk state.

9. The information processing apparatus according to claim 8,
wherein the distinguishing process is configured to distinguish the ground-off and landing timings of each of the four limbs of the animal from motion waveforms in an up-down direction and in a yaw axis direction when the gait of the animal is determined as the walk state, and
wherein the identifying process is configured to identify a limb having an abnormality based on the motion waveforms in at least one of a left-right direction, a front-rear direction, the up-down direction, and the yaw axis direction.

10. The information processing apparatus according to claim 8,
wherein the distinguishing process includes
distinguishing a first point of time at which a positive side and a negative side of acceleration in a yaw axis direction are reversed to each other as the ground-off timing of a right forelimb when the acceleration in the yaw axis direction increases in a left turn direction from the point of time,
distinguishing the first point of time as the ground-off timing of a left forelimb when the acceleration in the yaw axis direction increases in a right turn direction from the point of time,
distinguishing a point of time at which the negative side of acceleration in an up-down direction is reversed into the positive side of acceleration as the landing timing of the right forelimb when the yaw axis direction is the left turn direction at the point of time,
distinguishing a point of time at which the negative side of acceleration in the up-down direction is reversed into the positive side of acceleration as the landing timing of the left forelimb when the yaw axis direction is the right turn direction at the point of time,
distinguishing an intermediate timing between the ground-off timing of the right forelimb and the ground-off timing of the left forelimb as the ground-off timing of a left hindlimb,
distinguishing an intermediate timing between the ground-off timing of the left forelimb and the ground-off timing of the right forelimb as the ground-off timing of the right hindlimb,
distinguishing an intermediate timing between the landing timing of the right forelimb and the landing timing of the left forelimb as the landing timing of the left hindlimb, and
distinguishing an intermediate timing between the landing timing of the left forelimb and the landing timing of the right forelimb as the landing timing of the right hindlimb.

11. The information processing apparatus according to claim 7,
wherein the identifying process is configured to identify a limb having a small motion waveform in a front-rear direction as a limb having an abnormality among the limbs having the ground-off timing and the landing timing in a waveform with a large peak in the motion waveform in a left-right direction.

12. The information processing apparatus according to claim 7,
wherein the identifying process is configured to identify a limb in which the ground-off and landing timings correspond to a period during which an actual motion waveform deviates from an ideal motion waveform by a predetermined ratio or more, as a limb having a problem.

13. A non-transitory computer-readable storage medium storing a estimation program that causes a processor to execute a process, the process comprising:
executing a distinguishing process that includes distinguishing ground-off and landing timings of respective four limbs of an animal based on measurement data acquired by using a motion sensor attached in front of a chest region of the animal which has four limbs used to move in a quadrupedal manner, the measurement data indicating a movement of the chest region of the animal which has been measured by the motion sensor, and
executing a identifying process that includes identifying a limb which interlocks with a disorder of a motion waveform upon movement of the animal, based on the distinguished ground-off and landing timings of each of the four limbs of the animal.

14. The non-transitory computer-readable storage medium according to claim 13, the method further comprising:
executing a determining process that includes determining a gait of the animal based on the measurement data,
wherein the distinguishing process is configured to distinguish the ground-off and landing timings of each of the four limbs of the animal from the motion waveform upon the movement of the animal when the gait of the animal is determined as a walk state.

15. The non-transitory computer-readable storage medium according to claim 14,
wherein the distinguishing process is configured to distinguish the ground-off and landing timings of each of the four limbs of the animal from motion waveforms in an up-down direction and in a yaw axis direction when the gait of the animal is determined as the walk state, and
wherein the identifying process is configured to identify a limb having an abnormality based on the motion waveforms in at least one of a left-right direction, a front-rear direction, the up-down direction, and the yaw axis direction.

16. The non-transitory computer-readable storage medium according to claim 14,
wherein the distinguishing process includes
distinguishing a first point of time at which a positive side and a negative side of acceleration in a yaw axis direction are reversed to each other as the ground-off timing of a right forelimb when the acceleration in the yaw axis direction increases in a left turn direction from the point of time,
distinguishing the first point of time as the ground-off timing of a left forelimb when the acceleration in the yaw axis direction increases in a right turn direction from the point of time,
distinguishing a point of time at which the negative side of acceleration in an up-down direction is reversed into the positive side of acceleration as the landing timing of the right forelimb when the yaw axis direction is the left turn direction at the point of time,
distinguishing a point of time at which the negative side of acceleration in the up-down direction is reversed into the positive side of acceleration as the landing timing of the left forelimb when the yaw axis direction is the right turn direction at the point of time,
distinguishing an intermediate timing between the ground-off timing of the right forelimb and the ground-off timing of the left forelimb as the ground-off timing of a left hindlimb,
distinguishing an intermediate timing between the ground-off timing of the left forelimb and the ground-off timing of the right forelimb as the ground-off timing of the right hindlimb,
distinguishing an intermediate timing between the landing timing of the right forelimb and the landing timing of the left forelimb as the landing timing of the left hindlimb, and
distinguishing an intermediate timing between the landing timing of the left forelimb and the landing timing of the right forelimb as the landing timing of the right hindlimb.

17. The non-transitory computer-readable storage medium according to claim 13,
wherein the identifying process is configured to identify a limb having a small motion waveform in a front-rear direction as a limb having an abnormality among the limbs having the ground-off timing and the landing timing in a waveform with a large peak in the motion waveform in a left-right direction.

18. The non-transitory computer-readable storage medium according to claim 13,
wherein the identifying process is configured to identify a limb in which the ground-off and landing timings correspond to a period during which an actual motion waveform deviates from an ideal motion waveform by a predetermined ratio or more, as a limb having a problem.

* * * * *